(12) United States Patent
Yanaba et al.

(10) Patent No.: US 10,428,015 B2
(45) Date of Patent: Oct. 1, 2019

(54) ACID-RESISTANT BASE AND/OR RADICAL GENERATOR, AND CURABLE RESIN COMPOSITION CONTAINING SAID BASE AND/OR RADICAL GENERATOR

(71) Applicant: FUJIFILM Wako Pure Chemical Corporation, Osaka-shi, Osaka (JP)

(72) Inventors: Kosuke Yanaba, Kawagoe (JP); Nobuhiko Sakai, Kawagoe (JP); Shigeaki Imazeki, Kawagoe (JP)

(73) Assignee: FUJIFILM Wako Pure Chemical Corporation, Osaka (JP)

( * ) Notice: Subject to any disclaimer, the term of this patent is extended or adjusted under 35 U.S.C. 154(b) by 100 days.

(21) Appl. No.: 15/747,253

(22) PCT Filed: Jul. 22, 2016

(86) PCT No.: PCT/JP2016/071640
§ 371 (c)(1),
(2) Date: Jan. 24, 2018

(87) PCT Pub. No.: WO2017/018361
PCT Pub. Date: Feb. 2, 2017

(65) Prior Publication Data
US 2019/0002403 A1 Jan. 3, 2019

(30) Foreign Application Priority Data

Jul. 24, 2015 (JP) .................. 2015-146655

(51) Int. Cl.
*C07C 279/26* (2006.01)
*C07C 251/30* (2006.01)
(Continued)

(52) U.S. Cl.
CPC .......... *C07C 279/26* (2013.01); *C07C 251/30* (2013.01); *C07F 5/02* (2013.01); *C07F 9/5463* (2013.01); *C08G 59/4021* (2013.01); *C08G 59/42* (2013.01); *C08G 59/66* (2013.01); *C08G 59/686* (2013.01); *C08G 75/02* (2013.01); *C08K 5/29* (2013.01); *C08K 5/31* (2013.01); *C08L 63/00* (2013.01); *C08L 101/00* (2013.01); *C09K 3/00* (2013.01); *C07C 2601/14* (2017.05); *C08L 2312/06* (2013.01)

(58) Field of Classification Search
CPC . C08K 5/29; C08K 5/31; C08G 59/42; C08G 59/66; C08G 59/686; C08G 59/4021; C08L 101/00; C08L 63/00; C08L 2312/06; C09D 163/00; C09J 163/00; C07F 5/02; C07C 2601/14; C07C 279/26; C07C 251/30
See application file for complete search history.

(56) References Cited

U.S. PATENT DOCUMENTS 2,768,205 A 10/1956 Hechenbleikner et al.
3,261,809 A 7/1966 Sherr
(Continued)

FOREIGN PATENT DOCUMENTS

JP H09278738 10/1997
JP H09292712 11/1997
(Continued)

OTHER PUBLICATIONS

G. Gelbard and F. Vielfaure-Joly, "Polynitrogen Strong Bases : 1—New Syntheses of Biguanides and their Catalytic Properties in Transesterification Reactions," Tetrahedron Letters, vol. 39 (1998), p. 2743-2746.
(Continued)

*Primary Examiner* — Kregg T Brooks
(74) *Attorney, Agent, or Firm* — Hamre, Schumann, Mueller & Larson, P.C.

(57) ABSTRACT

The present invention relates to a compound represented by the general formula (A), a base- and/or radical-generating agent comprising the compound, and so on.

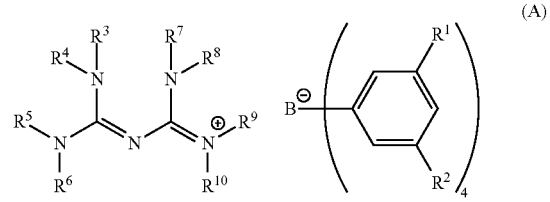

(A)

In the formula, four pieces of $R^1$ each independently represents a hydrogen atom or a fluorine atom; four pieces of $R^2$ each independently represent a fluorine atom or a trifluoromethyl group; $R^3$, $R^6$, $R^7$ and $R^{10}$ each independently represent a hydrogen atom or an alkyl group having 1 to 12 carbon atoms; $R^4$ and $R^5$ each independently represent a hydrogen atom or an alkyl group having 1 to 12 carbon atoms, or $R^4$ and $R^5$ are bonded to each other to represent an alkylene group having 2 to 4 carbon atoms; and $R^8$ and $R^9$ each independently represent a hydrogen atom, an alkyl group having 1 to 12 carbon atoms, or an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group, or $R^8$ and $R^9$ are bonded to each other to represent an alkylene group having 2 to 4 carbon atoms; provided that two or three of the eight groups $R^3$ to $R^{10}$ are each a hydrogen atom, and, in a case where two of the eight groups are each a hydrogen atom, then three to six of the remaining groups are each an alkyl group having 1 to 12 carbon atoms, and, in a case where three of the eight groups are each a hydrogen atom, then four or five of the remaining groups are each an alkyl group having 1 to 12 carbon atoms.

15 Claims, No Drawings

(51) Int. Cl.

| | |
|---|---|
| *C07F 5/02* | (2006.01) |
| *C08G 59/40* | (2006.01) |
| *C08G 59/42* | (2006.01) |
| *C08G 59/66* | (2006.01) |
| *C08G 59/68* | (2006.01) |
| *C08K 5/29* | (2006.01) |
| *C08K 5/31* | (2006.01) |
| *C08L 63/00* | (2006.01) |
| *C08L 101/00* | (2006.01) |
| *C08L 101/06* | (2006.01) |
| *C09K 3/00* | (2006.01) |
| *G03F 7/004* | (2006.01) |
| *C07F 9/54* | (2006.01) |
| *C08G 75/02* | (2016.01) |

(56) References Cited

U.S. PATENT DOCUMENTS

| | | |
|---|---|---|
| 2016/0122292 A1 | 5/2016 | Sakai et al. |
| 2016/0340374 A1 | 11/2016 | Sakai et al. |

FOREIGN PATENT DOCUMENTS

| | | |
|---|---|---|
| JP | 2010138234 | 6/2010 |
| JP | 2011236416 | 11/2011 |
| JP | 2012131936 | 7/2012 |
| JP | 2012250969 | 12/2012 |
| JP | 2014097930 | 5/2014 |
| JP | 2015061823 | 4/2015 |
| WO | 2010095390 | 8/2010 |
| WO | 2014208632 | 12/2014 |
| WO | 2015083331 | 6/2015 |
| WO | 2015111640 | 7/2015 |

OTHER PUBLICATIONS

O. Grinevich et al, "Relative Activity of Possible Initiating Species Produced from Photolysis of Tetraphenyl and Triphenylbutyl Borates as Measured by Fluorescence Probe Techniques," Macromolecules, vol. 32 (1999), p. 328-330.

S. Hassoon et al., "Photochemistry of (Benzophenonylmethyl)-tri-n-butylammonium Triphenylbutylborate: Inter- and Intra-Ion-Pair Electron Transfer Photoreduction," J. Am. Chem. Soc., vol. 117 (1995), p. 11369-11370.

S. Hu et al., "Reactivities of Chromophore-Containing Methyl Tri-n-butylammonium Organoborate Salts as Free Radical Photoinitiators: Dependence on the Chromophore and Borate Counterion," Macromolecules, vol. 31 (1998), p. 6476-6480.

K. Ito et al., "Thermal Crosslinking of Poly (glycidyl methacrylate) Films and Epoxy Resin Films Using Amines Formed by Photolysis of O-acyloximes," Journal of Polymer Science: Part A: Polymer Chemistry, vol. 32 (1994), p. 1793-1796.

J. C. Jochims et al., "Amino-substituted 2-Azaallenium Salts," Chem Ber., vol. 117 (1984), p. 1900-1912.

R. Popielarz et al., "Applicability of Tetraphenylborate Salts as Free Radical Initiators," Macromolecules, vol. 31, No. 4 (1998), p. 951-954.

Y. Shibasaki et al., "Synthesis of Photobase Generators Based on Proazaphosphatrane—Tetraarylborate Complex for i-Line Photopatterning," Journal of Photopolymer Science and Technology, vol. 25, No. 4 (2012), p. 497-499.

X. Sun et al., "Bicyclic Guanidinium Tetraphenylborate: A Photobase Generator and a Photocatalyst for Living Anionic Ring-Opening Polymerization and Cross-Linking of Polymeric Materials Containing Ester and Hydroxy Groups," J. Am. Chem. Soc., vol. 130 (2008), p. 8130-8131.

International Search Report for international appl. No. PCT/JP2016/071640, dated Sep. 13, 2016 (4 pages, including English translation).

ACID-RESISTANT BASE AND/OR RADICAL GENERATOR, AND CURABLE RESIN COMPOSITION CONTAINING SAID BASE AND/OR RADICAL GENERATOR

TECHNICAL FIELD

The present invention relates to a base- and/or radical-generating agent or the like to be used in the field of resists and so on. More specifically, the present invention relates to a borate compound having a property to generate a biguanide as a strong base and having acid resistance, a base- and/or radical-generating agent comprising the borate compound, a curable resin composition comprising the borate compound, and so on.

BACKGROUND ART

Research and development for application of photosensitive compositions containing a base polymerization initiator (a base-generating agent) to photoresist materials, photocurable materials, and so on has been actively conducted in recent years. For example, a method utilizing the phenomenon that a compound having an epoxy group (hereinafter, occasionally abbreviated as "epoxy compounds") cures through undergoing crosslinking reaction caused by the action of a base has been proposed in which a base is generated in a resin composition containing an epoxy compounds through irradiation with light (an active energy ray) and then the epoxy compounds is cured through heating (e.g., Non Patent Literature 1).

For the curing of an epoxy compounds, a strong base such as a tertiary amine, an amidine, and a guanidine is used as a base polymerization initiator (a base-generating agent) which readily functions as a catalyst. Known examples of base polymerization initiators (base-generating agents) to generate such a strong base include aminimide base-generating agent (e.g., Patent Literature 1) which generates a tertiary amine, an amidine such as 1,5-diazabicyclo[4.3.0]-5-nonene (DBN) and 1,8-diazabicyclo[5.4.0]-7-undecene (DBU), an imidazole, or a pyridine, etc., through irradiation with light (an active energy ray), ammonium borate base-generating agents (e.g., Patent Literature 2, Patent Literature 3, Non Patent Literature 2, Non Patent Literature 3, Non Patent Literature 4, Non Patent Literature 5), and carbamate base-generating agents (e.g., Patent Literature 4). In addition, known are, for example, a base-generating agent which consists of a carboxylic acid and an amine and undergoes decarboxylation through irradiation with light (an active energy ray) (e.g., Patent Literature 5), a benzoic acid-based base-generating agent which undergoes cyclic esterification through irradiation with light (an active energy ray) (e.g., Patent Literature 6), and a tetraphenylborate base-generating agent which generates a guanidine such as 1,1,3,3-tetramethylguanidine (TMG), 1,5,7-triazabicyclo[4.4.0]dec-5-ene (TBD), and 7-methyl-1,5,7-triazabicyclo[4.4.0]dec-5-ene (MTBD) through irradiation with light (an active energy ray) (e.g., Non Patent Literature 6). In addition, known examples of base polymerization initiators (base-generating agents) to generate a strong base other than tertiary amines, amidines, and guanidines include a tetraarylborate base-generating agent which generates a proazaphosphatrane such as 2,8,9-triisopropyl-2,5,8,9-tetraaza-1-phosphabicyclo[3.3.3]undecane through irradiation with light (an active energy ray) (e.g., Non Patent Literature 7). In addition, biguanides, which have higher basicity than amidines and guanidines, are known (e.g., Patent Literature 7, Non Patent Literature 8, Non Patent Literature 9), and an example in which a biguanide is used for curing an epoxy compounds (e.g., Patent Literature 8) and an example in which a compound obtained by salt formation of a pyrolytic compound and a biguanide is applied as a heat-curing catalyst (e.g., Patent Literature 9, Patent Literature 10) are known. In addition, the present inventors have reported a base-generating agent consisting of a carboxylic acid with a particular structure and a biguanide (Patent Literature 11).

Moreover, the present inventors have just recently reported a base-generating agent consisting of a borate with a particular structure and a strong base such as a biguanide (e.g., Patent Literature 12). The base-generating agent described in Patent Literature 12 has an anionic portion of a borate, by virtue of which the base-generating agent is characterized in that even after the base-generating agent is stored in a state in which the base-generating agent is mixed in a base-curable resin raw material such as an epoxy compounds for a long period, the base-generating agent does not cause curing of the base-curable resin raw material.

CITATION LIST

Patent Literature

Patent Literature 1: Japanese Patent Application Laid-Open Publication No. 2012-131936
Patent Literature 2: International Publication No. WO 2010/095390
Patent Literature 3: Japanese Patent Application Laid-Open Publication No. 2014-97930
Patent Literature 4: Japanese Patent Application Laid-Open Publication No. 2015-61823
Patent Literature 5: Japanese Patent Application Laid-Open Publication No. 2011-236416
Patent Literature 6: Japanese Patent Application Laid-Open Publication No. 2012-250969
Patent Literature 7: U.S. Pat. No. 2,768,205
Patent Literature 8: U.S. Pat. No. 3,261,809
Patent Literature 9: Japanese Patent Application Laid-Open Publication No. 9-278738
Patent Literature 10: Japanese Patent Application Laid-Open Publication No. 9-292712
Patent Literature 11: International Publication No. WO 2014/208632
Patent Literature 12: International Publication No. WO 2015/111640

Non Patent Literature

Non Patent Literature 1: J. Polym. Sci., Part A: Polym. Chem., 32, 1793 (1994)
Non Patent Literature 2: J. Am. Chem. Soc., 117, 11369-11370 (1995)
Non Patent Literature 3: Macromolecules, 31, 951-954 (1998)
Non Patent Literature 4: Macromolecules, 31, 6476-6480 (1998)
Non Patent Literature 5: Macromolecules, 32, 328-330 (1999)
Non Patent Literature 6: J. Am. Chem. Soc., 130, 8130 (2008)
Non Patent Literature 7: J. Photopolym. Sci. Tech., 25, 497-499 (2012)
Non Patent Literature 8: Tetrahedron Lett., 39, 2743 (1998)
Non Patent Literature 9: Chem. Ber., 117, 1900-1912 (1984)

SUMMARY OF INVENTION

Technical Problem

However, the base-generating agent described in Patent Literature 12 has been found to be unstable against acidic compounds and be easily decomposed by the action of an acid. The specific findings are as follows: when the base-generating agent described in Patent Literature 12 is applied to a resin composition containing an epoxy compounds or the like and a compound having an acidic proton (an acidic compound) such as a multivalent carboxylic acid, a polyhydric phenol, a polythiol, and a multivalent β-keto ester, the borate structure as the anionic portion of the base-generating agent decomposes by the action of an acid derived from the compound having an acidic proton regardless of the presence or absence of irradiation with light (an active energy ray), and a base is generated in association with the decomposition of the borate structure, or the base-generating agent cannot remain latent and exhibits basicity to activate the compound having an acidic proton (an acidic compound); for this reason, when a base-curable resin composition obtained by adding a compound having an acidic proton to a composition containing the base-generating agent described in Patent Literature 12 and a base-curable resin raw material is applied to a photocurable system, an exposed portion (a portion irradiated with light) and an unexposed portion (a portion not irradiated with light) are both cured to result in an insufficient contrast ratio in some cases. In such circumstances, development of a base-generating agent has been desired which can generate a strong base through irradiation with light (an active energy ray) even when being applied to a composition containing an epoxy compounds or the like and an acidic compound such as a compound having an acidic proton in combination, without being easily decomposed nor causing activation of the acidic compound.

The present invention was made in view of the circumstances described above, and an object of the present invention is to provide a borate compound which can generate a biguanide as a strong base through irradiation with light (an active energy ray) or heating even when being applied to a curable resin composition containing an acidic compound, without being easily decomposed nor causing activation of the acidic compound, a base- and/or radical-generating agent comprising the borate compound, and a base- and/or radical-curable resin composition comprising the borate compound and a base-curable resin raw material and/or a radical-reactive compound, and so on.

Solution to Problem

The present invention consists of the following configurations.

(1) A compound represented by the general formula (A) (hereinafter, occasionally abbreviated as "the compound of the present invention"):

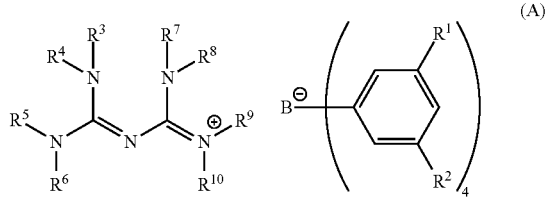

wherein four pieces of $R^1$ each independently represent a hydrogen atom or a fluorine atom; four pieces of $R^2$ each independently represent a fluorine atom or a trifluoromethyl group; $R^3$, $R^6$, $R^7$ and $R^{10}$ each independently represent a hydrogen atom or an alkyl group having 1 to 12 carbon atoms; $R^4$ and $R^5$ each independently represent a hydrogen atom or an alkyl group having 1 to 12 carbon atoms, or $R^4$ and $R^5$ are bonded to each other to represent an alkylene group having 2 to 4 carbon atoms; and $R^8$ and $R^9$ each independently represent a hydrogen atom, an alkyl group having 1 to 12 carbon atoms, or an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group, or $R^8$ and $R^9$ are bonded to each other to represent an alkylene group having 2 to 4 carbon atoms; provided that two or three of the eight groups $R^3$ to $R^{10}$ are each a hydrogen atom, and, in a case where two of the eight groups are each a hydrogen atom, then three to six of the remaining groups are each an alkyl group having 1 to 12 carbon atoms, and, in a case where three of the eight groups are each a hydrogen atom, then four or five of the remaining groups are each an alkyl group having 1 to 12 carbon atoms.

(2) A base- and/or radical-generating agent comprising the compound represented by the general formula (A) (hereinafter, occasionally abbreviated as "the base-generating agent of the present invention" and "the radical-generating agent of the present invention", respectively).

(3) A base-generating agent comprising the compound represented by the general formula (A).

(4) A base- and/or radical-curable resin composition characterized by comprising the compound represented by the general formula (A), and a base-curable resin raw material and/or a radical-reactive compound (hereinafter, occasionally abbreviated as "the base-curable resin composition of the present invention" and "the radical-curable resin composition of the present invention", respectively).

(5) A base-curable resin composition characterized by comprising the compound represented by the general formula (A), and a base-curable resin raw material.

Advantageous Effects of Invention

The compound of the present invention consists of a salt structure of a borate anion with a particular structure and a cation derived from a biguanide as a strong base, and generates a strong base and/or a radical through irradiation of the compound of the present invention with light (an active energy ray) or heating the compound of the present invention. The compound of the present invention has acid resistance and can quickly generate a base and/or a radical through irradiation with light (an active energy ray) or heating because the anionic portion of the compound of the present invention is a borate anion with a particular structure. In addition, the compound of the present invention can cure various resin raw materials through generation of a strong base because the cationic portion is a cation derived from a biguanide. Accordingly, the base- and/or radical-generating agent comprising the compound of the present invention can advantageously generate a biguanide as a strong base and/or a radical through irradiation with light (an active energy ray) or heating while even when being applied to a composition containing an acidic compound, the base- and/or radical-generating agent is not easily decomposed and does not cause activation of the acidic compound.

The curable resin composition of the present invention can be stably stored even in a case where an acidic compound (e.g., a monomer raw material having an acidic proton, a crosslinking agent having an acidic proton) is contained therein because the compound of the present invention contained in the composition has acid resistance. The strong base generated from the base-generating agent of the present invention can quickly initiate curing of an epoxy compounds, and, in addition, an acidic compound or the like can accelerate the curing rate of an epoxy compounds, and hence the curable resin composition of the present invention is advantageously effective particularly for a curing system for an epoxy compounds.

DESCRIPTION OF EMBODIMENTS

In the present invention, active energy rays include not only electromagnetic waves at wavelengths in the visible region (visible rays) but also electromagnetic waves at wavelengths in a non-visible region such as electromagnetic waves at wavelengths in the ultraviolet region (ultraviolet rays), electromagnetic waves at wavelengths in the infrared region (infrared rays), and X-rays, unless specification of a wavelength is made. In the present invention, a base-generating agent susceptible to active energy rays (a base-generating agent which generates a base through irradiation with an active energy ray) is occasionally referred to as a photo-base-generating agent, and a radical-generating agent susceptible to active energy rays (a radical-generating agent which generates a radial through irradiation with an active energy ray) is occasionally referred to as a photo-radical-generating agent. In addition, active energy rays at a wavelength of 365 nm, 405 nm, and 436 nm are occasionally represented as an i-ray, an h-ray, and a g-ray, respectively.
—Compound of the Present Invention—
The compound of the present invention is represented by the general formula (A):

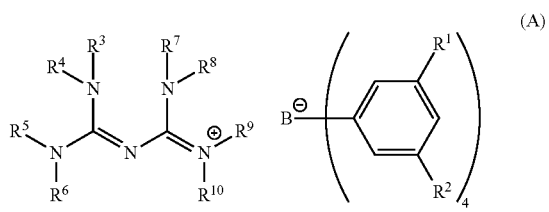

wherein four pieces of $R^1$ each independently represent a hydrogen atom or a fluorine atom; four pieces of $R^2$ each independently represent a fluorine atom or a trifluoromethyl group; $R^3$, $R^6$, $R^7$ and $R^{10}$ each independently represent a hydrogen atom or an alkyl group having 1 to 12 carbon atoms; $R^4$ and $R^5$ each independently represent a hydrogen atom or an alkyl group having 1 to 12 carbon atoms, or $R^4$ and $R^5$ are bonded to each other to represent an alkylene group having 2 to 4 carbon atoms; and $R^8$ and $R^9$ each independently represent a hydrogen atom, an alkyl group having 1 to 12 carbon atoms, or an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group, or $R^8$ and $R^9$ are bonded to each other to represent an alkylene group having 2 to 4 carbon atoms; provided that two or three of the eight groups $R^3$ to $R^{10}$ are each a hydrogen atom, and, in a case where two of the eight groups are each a hydrogen atom, then three to six of the remaining groups are each an alkyl group having 1 to 12 carbon atoms, and, in a case where three of the eight groups are each a hydrogen atom, then four or five of the remaining groups are each an alkyl group having 1 to 12 carbon atoms.

The four pieces of $R^1$ in the general formula (A) may be each independently a hydrogen atom or a fluorine atom. Especially, it is preferable that the four pieces of $R^1$ be each a hydrogen atom or that the four pieces of $R^1$ be each a fluorine atom.

The four pieces of $R^2$ in the general formula (A) may be each independently a fluorine atom or a trifluoromethyl group. Especially, it is preferable that the four pieces of $R^2$ be each a fluorine atom or that the four pieces of $R^2$ be each a trifluoromethyl group.

Regarding the combination of $R^1$ and $R^2$ in the general formula (A), in a case where $R^1$ is a hydrogen atom, then each $R^2$ is preferably a fluorine atom or a trifluoromethyl group, and, in a case where $R^1$ is a fluorine atom, then each $R^2$ is preferably a fluorine atom. That is, the following three combinations 1. to 3. are preferred for each of combinations of the four pieces of $R^1$ and the four pieces of $R^2$.

1. $R^1$: hydrogen atom, $R^2$: fluorine atom
2. $R^1$: hydrogen atom, $R^2$: trifluoromethyl group
3. $R^1$: fluorine atom, $R^2$: fluorine atom In other words, the combination "$R^1$: fluorine atom, $R^2$: trifluoromethyl group" is excluded from the preferred combinations.

Specific examples of the borate anion represented by the general formula (B) below as a partial structure of the compound represented by the general formula (A) include those represented by the formulae (B-1) to (B-15) below. It should be noted that the borate anion represented by the general formula (B) is not limited to the borate anions represented by the formulae (B-1) to (B-15) below.

General formula (B):

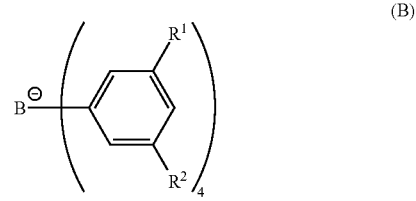

wherein four pieces of $R^1$ and four pieces of $R^2$ are as described above.

Formulae (B-1) to (B-15):

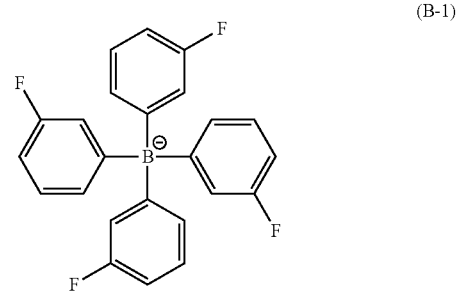

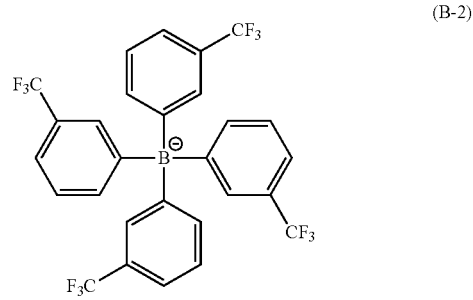

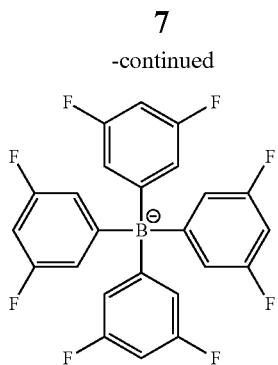
(B-3)
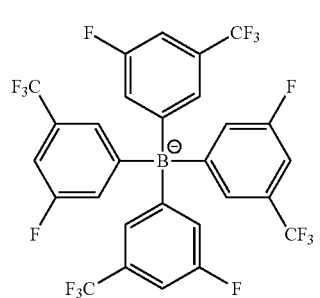
(B-4)
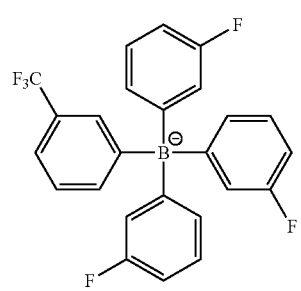
(B-5)
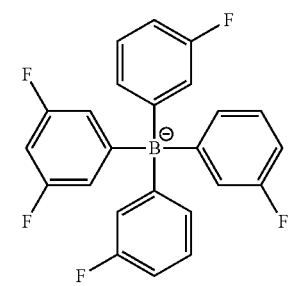
(B-6)
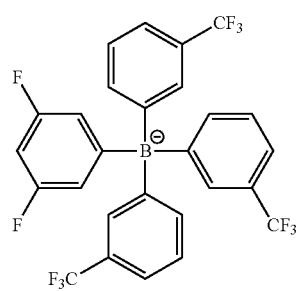
(B-7)
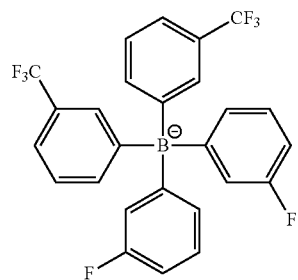
(B-8)
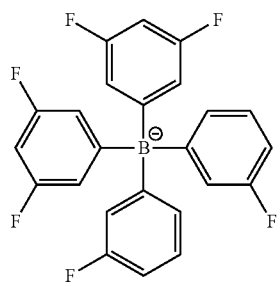
(B-9)
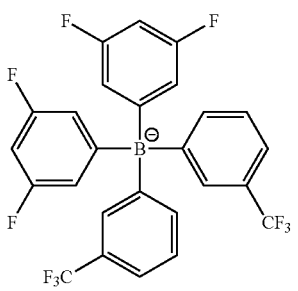
(B-10)
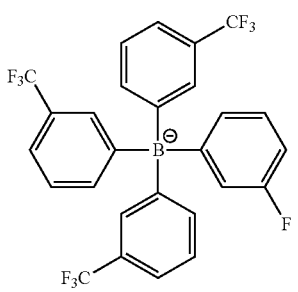
(B-11)
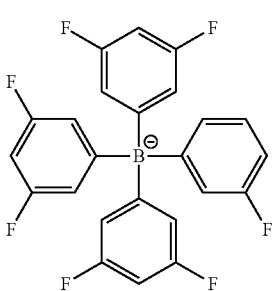
(B-12)

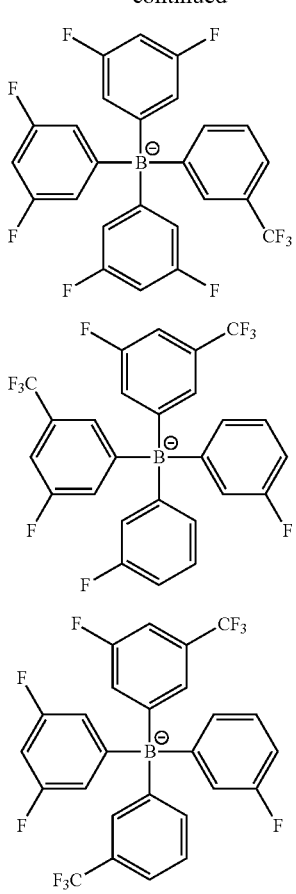

(B-13)

(B-14)

(B-15)

Because the compound of the present invention has the borate anion with the particular structure represented by the general formula (B), the compound of the present invention not only has acid resistance, but also quickly generates a base by a mechanism in which an intermediate having a radical is generated in association with the decomposition of the tetraphenylborate structure through irradiation with light (an active energy ray) or heating and the cationic portion then immediately dissociates from the intermediate.

Among the borate anions represented by the general formula (B), a borate anion represented by the general formula (B') below is preferred.

General Formula (B'):

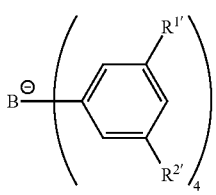

(B')

wherein four pieces of $R^{1'}$ are all identical and each represent a hydrogen atom or a fluorine atom; and four pieces of $R^{2'}$ are all identical and each represent a fluorine atom or a trifluoromethyl group; provided that a combination of $R^{1'}$ being a fluorine atom and $R^{2'}$ being a trifluoromethyl group is excluded.

Examples of combinations of $R^{1'}$ and $R^{2'}$ in the general formula (B') include the following three combinations 1. to 3.

1. $R^{1'}$: hydrogen atom, $R^{2'}$: fluorine atom
2. $R^{1'}$: hydrogen atom, $R^{2'}$: trifluoromethyl group
3. $R^{1'}$: fluorine atom, $R^{2'}$: fluorine atom Specific examples of the borate anion represented by the general formula (B') include those represented by the formulae (B-1) to (B-3).

Among the borate anions, the compound of the present invention having the borate anion represented by the general formula (B') not only has higher acid resistance, but also can generate a base more quickly through irradiation with light (an active energy ray) or heating. Thus, the compound of the present invention having the borate anion represented by the general formula (B') can advantageously provide a higher contrast ratio between an exposed portion (a portion irradiated with light) and an unexposed portion (a portion not irradiated with light) in a curing system for an epoxy compounds.

Specific examples of the compound of the present invention in a case where the borate anion is an anion represented by any of the formulae (B-1) to (B-3) include compounds represented by the general formulae (B-A1) to (B-A3) below.

General Formulae (B-A1) to (B-A3):

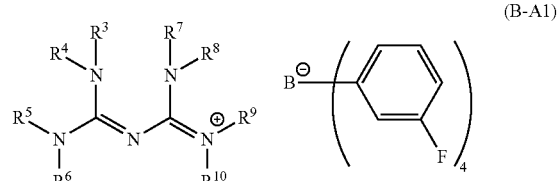

(B-A1)

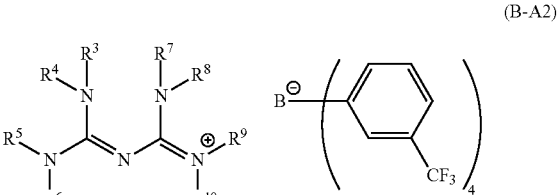

(B-A2)

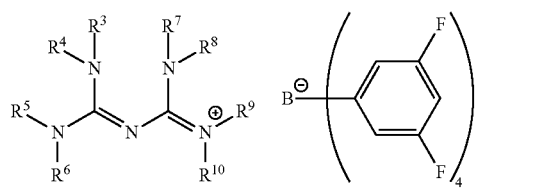

(B-A3)

wherein $R^3$ to $R^{10}$ are as described above.

The alkyl group having 1 to 12 carbon atoms represented as any of $R^3$ to $R^7$ and $R^{10}$ in the general formula (A) may be any of linear, branched, or cyclic, and specific examples of such alkyl groups include a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a n-nonyl group, an isononyl group, a sec-nonyl group, a tert-nonyl group, a neononyl group, a cyclononyl group, a n-decyl group, an isodecyl group, a sec-decyl group, a tert-decyl group, a neodecyl group, a cyclodecyl group, a n-undecyl group, a cycloundecyl group, a n-dodecyl group, a cyclododecyl group, a norbornyl group (bornan-χ-yl group), a bornyl group (bornan-χ-yl group), a menthyl group (menth-χ-yl group), an adamantyl group, and a decahydronaphthyl group. Among these alkyl groups, the linear, branched, or cyclic alkyl groups having 1 to 6 carbon atoms are preferred, and the linear, branched, or cyclic alkyl groups having 1 to 4 carbon atoms are more preferred, and the methyl group, which is an alkyl group having 1 carbon atom, is particularly preferred.

In a case where "$R^4$ and $R^5$ are bonded to each other to represent an alkylene group having 2 to 4 carbon atoms" in the general formula (A), the alkylene group having 2 to 4 carbon atoms may be any of linear or branched, and specific examples of such alkylene groups include a dimethylene group (an ethylene group), a trimethylene group, a propylene group, a tetramethylene group, a 1-methyltrimethylene group, a 2-methyltrimethylene group, a 1,2-dimethyldimethylene group (a 1,2-dimethylethylene group), a 1,1-dimethyldimethylene group (a 1,1-dimethylethylene group), and an ethyldimethylene group (an ethylethylene group). Among these alkylene groups having 2 to 4 carbon atoms, the dimethylene group (the ethylene group), which is a liner alkylene group having 2 carbon atoms, is preferred.

In a case where "$R^4$ and $R^5$ are bonded to each other to represent an alkylene group having 2 to 4 carbon atoms" in the general formula (A), the alkylene group and a —N—C—N— group bonding to the alkylene group form a 5- to 7-membered cyclic structure.

Specific examples of the cyclic structure include an imidazolidine ring, a hexahydropyrimidine ring, a 4-methylimidazolidine ring, a 5-methylimidazolidine ring, a 1,3-diazacycloheptane ring, a 4-methylhexahydropyrimidine ring, a 5-methylhexahydropyrimidine ring, a 6-methylhexahydropyrimidine ring, a 4-ethylimidazolidine ring, a 5-ethylimidazolidine ring, a 4,4-dimethylimidazolidine ring, a 4,5-dimethylimidazolidine ring, and a 5,5-dimethylimidazolidine ring. Among these cyclic structures, the imidazolidine ring is preferred.

Alkyl group having 1 to 12 carbon atoms is preferred for $R^3$ to $R^6$ in the general formula (A), and it is more preferred that all of $R^3$ to $R^6$ be an alkyl group having 1 to 12 carbon atoms.

A hydrogen atom is preferred for $R^7$ and $R^{10}$ in the general formula (A), and it is more preferred that $R^7$ and $R^{10}$ be each a hydrogen atom.

The alkyl group having 1 to 12 carbon atoms represented as any of $R^8$ and $R^9$ in the general formula (A) may be any of linear, branched, or cyclic, and specific examples of such alkyl groups include those exemplified for the alkyl group having 1 to 12 carbon atoms represented as any of $R^3$ to $R^7$ and $R^{10}$ in the general formula (A). Among these alkyl groups, the linear, branched, or cyclic alkyl groups having 2 to 8 carbon atoms are preferred, and the linear, branched, or cyclic alkyl groups having 3 to 6 carbon atoms are more preferred, and the branched or cyclic alkyl groups having 3 to 6 carbon atoms are even more preferred.

The concept of the expression "aryl group having 6 to 14 carbon atoms and optionally having a substituent" in the phrase "an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented as any of $R^8$ and $R^9$ in the general formula (A) is intended to encompass both an aryl group having 6 to 14 carbon atoms and having no substituent, and an aryl group having 6 to 14 carbon atoms and having a substituent.

The aryl group having 6 to 14 carbon atoms in the phrase "an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented as any of $R^8$ and $R^9$ in the general formula (A) may be any of monocyclic or condensed polycyclic, and specific examples of such aryl groups include a phenyl group, a naphthyl group, and an anthracenyl group. Among these aryl groups, the phenyl group, which is an aryl group having 6 carbon atoms, is preferred. It should be noted that the number of carbon atoms in an aryl group here refers to the number of carbon atoms constituting the aryl group, and the number of carbon atoms constituting a substituent is not included in the number of carbon atoms represented by the expression "6 to 14 carbon atoms" in the phrase "an aryl group having 6 to 14 carbon atoms".

The alkyl group having 1 to 6 carbon atoms in the phrase "an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented as any of $R^8$ and $R^9$ in the general formula (A) may be any of linear, branched, or cyclic, and specific examples of such alkyl groups include a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, and a cyclohexyl group. Among these alkyl groups, the linear or branched alkyl groups having 1 to 3 carbon atoms are preferred.

The alkoxy group having 1 to 6 carbon atoms in the phrase "an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented as any of $R^8$ and $R^9$ in the general formula (A) may be any of linear, branched, or cyclic, and specific examples of such alkoxy groups include a methoxy group, an ethoxy group, a n-propoxy group, an isopropoxy group, a n-butoxy group, an isobutoxy group, a sec-butoxy group, a tert-butoxy group, a cyclobutoxy group, a n-pentyloxy group, an isopentyloxy group, a sec-pentyloxy group, a tert-pentyloxy group, a neopentyloxy group, a 2-methylbutoxy group, a 1,2-dimethylpropoxy group, a 1-ethylpropoxy group, a cyclopentyloxy group, a n-hexyloxy group, an isohexyloxy group, a sec-hexyloxy group, a tert-hexyloxy group, a neohexyloxy group, a 2-methylpentyloxy group, a 1,2-dimethylbutoxy group, a 2,3-dimethylbutoxy group, a 1-ethylbutoxy group, and a cyclohexyloxy group. Among these alkoxy groups, the linear or branched alkoxy groups having 1 to 3 carbon atoms are preferred.

The alkylthio group having 1 to 6 carbon atoms in the phrase "an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented as any of $R^8$ and $R^9$ in the general formula (A) may be any of linear, branched, or cyclic, and specific examples of such alkylthio groups include a methylthio group, an ethylthio group, a n-propylthio group, an isopropylthio group, a n-butylthio group, an isobutylthio group, a sec-butylthio group, a tert-butylthio group, a cyclobutylthio group, a n-pentylthio group, an isopentylthio group, a sec-pentylthio group, a tert-pentylthio group, a neopentylthio group, a 2-methylbutylthio group, a 1,2-dimethylpropylthio group, a 1-ethylpropylthio group, a cyclopentylthio group, a n-hexylthio group, an isohexylthio group, a sec-hexylthio group, a tert-hexylthio group, a neohexylthio group, a 2-methylpentylthio group, a 1,2-dimethylbutylthio group, a 2,3-dimethylbutylthio group, a 1-ethylbutylthio group, and a cyclohexylthio group. Among these alkylthio groups, the linear or branched alkylthio groups having 1 to 3 carbon atoms are preferred.

The dialkylamino group having 2 to 12 carbon atoms in the phrase "an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented as any of $R^8$ and $R^9$ in the general formula (A) may be any of linear, branched, or cyclic, and specific examples of such dialkylamino groups include an N,N-dimethylamino group, an N,N-diethylamino group, an N,N-di-n-propylamino group, an N,N-diisopropylamino group, an N,N-di-n-butylamino group, an N,N-diisobutylamino group, an N,N-di-sec-butylamino group, an N,N-di-tert-butylamino group, an N,N-dicyclobutylamino group, an N,N-di-n-pentylamino group, an N,N-diisopentylamino group, an N,N-di-sec-pentylamino group, an N,N-di-tert-pentylamino group, an N,N-dineopentylamino group, an N,N-di(2-methylbutyl)amino group, an N,N-bis(1,2-dimethylpropyl)amino group, an N,N-di(1-ethylpropyl)amino group, an N,N-dicyclopentylamino group, an N,N-di-n-hexylamino group, an N,N-diisohexylamino group, an N,N-di-sec-hexylamino group, an N,N-di-tert-hexylamino group, an N,N-dineohexylamino group, an N,N-di(2-methylpentyl)amino group, an N,N-bis(1,2-dimethylbutyl)amino group, an N,N-bis(2,3-dimethylbutyl)amino group, an N,N-di(1-ethylbutyl)amino group, an N,N-dicyclohexylamino group, an N,N-ethylmethylamino group, an N,N-methyl-n-propylamino group, an N,N-methylisopropylamino group, an N,N-n-butylmethylamino group, an N,N-isobutylmethylamino group, an N,N-sec-butylmethylamino group, an N,N-tert-butylmethylamino group, an N,N-cyclobutylmethylamino group, an N,N-methyl-n-pentylamino group, an N,N-n-hexylmethylamino group, an N,N-n-heptylmethylamino group, an N,N-methyl-n-octylamino group, an N,N-methyl-n-nonylamino group, an N,N-n-decylmethylamino group, an N,N-methyl-n-undecylamino group, an N,N-ethyl-n-propylamino group, an N,N-ethylisopropylamino group, an N,N-n-butylethylamino group, an N,N-isobutylethylamino group, an N,N-sec-butylethylamino group, an N,N-tert-butylethylamino group, an N,N-cyclobutylethylamino group, an N,N-ethyl-n-pentylamino group, an N,N-ethyl-n-hexylamino group, an N,N-ethyl-n-heptylamino group, an N,N-ethyl-n-octylamino group, an N,N-ethyl-n-nonylamino group, an N,N-ethyl-n-decylamino group, an N,N-n-propylisopropylamino group, an N,N-n-butyl-n-propylamino group, an N,N-isobutyl-n-propylamino group, an N,N-sec-butyl-n-propylamino group, an N,N-tert-butyl-n-propylamino group, an N,N-cyclobutyl-n-propylamino group, an N,N-n-pentyl-n-propylamino group, an N,N-n-hexyl-n-propylamino group, an N,N-n-heptyl-n-propylamino group, an N,N-n-octyl-n-propylamino group, an N,N-n-nonyl-n-propylamino group, an N,N-n-butylisopropylamino group, an N,N-isobutylisopropylamino group, an N,N-sec-butylisopropylamino group, an N,N-tert-butylisopropylamino group, an N,N-cyclobutylisopropylamino group, an N,N-n-pentylisopropylamino group, an N,N-n-hexylisopropylamino group, an N,N-n-heptylisopropylamino group, an N,N-n-octylisopropylamino group, an N,N-n-nonylisopropylamino group, an N,N-n-butylisobutylamino group, an N,N-n-butyl-sec-butylamino group, an N,N-n-butyl-tert-butylamino group, an N,N-n-butylcyclobutylamino group, an N,N-n-butyl-n-pentylamino group, an N,N-n-butyl-n-hexylamino group, an N,N-n-butyl-n-heptylamino group, an N,N-n-butyl-n-octylamino group, an N,N-isobutyl-sec-butylamino group, an N,N-isobutyl-tert-butylamino group, an N,N-isobutylcyclobutylamino group, an N,N-isobutyl-n-pentylamino group, an N,N-isobutyl-n-hexylamino group, an N,N-isobutyl-n-heptylamino group, an N,N-isobutyl-n-octylamino group, an N,N-sec-butyl-tert-butylamino group, an N,N-sec-butylcyclobutylamino group, an N,N-sec-butyl-n-pentylamino group, an N,N-sec-butyl-n-hexylamino group, an N,N-sec-butyl-n-heptylamino group, an N,N-sec-butyl-n-octylamino group, an N,N-tert-butylcyclobutylamino group, an N,N-tert-butyl-n-pentylamino group, an N,N-tert-butyl-n-hexylamino group, an N,N-tert-butyl-n-heptylamino group, an N,N-tert-butyl-n-octylamino group, an N,N-cyclobutyl-n-pentylamino group, an N,N-cyclobutyl-n-hexylamino group, an N,N-cyclobutyl-n-heptylamino group, an N,N-cyclobutyl-n-octylamino group, an N,N-n-hexyl-n-pentylamino group, and an N,N-n-heptyl-n-pentylamino group. Among these dialkylamino groups, the linear, branched, or cyclic dialkylamino groups having 2 to 6 carbon atoms are preferred.

Examples of the halogen atom in the phrase "an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented as any of $R^8$ and $R^9$ in the general formula (A) include a fluorine atom, a chlorine atom, a bromine atom, and an iodine atom. Among them, the fluorine atom and the chlorine atom are preferred.

The "substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" in any of $R^8$ and $R^9$ in the general formula (A) is preferably the alkyl group having 1 to 6 carbon atoms, the alkoxy group having 1 to 6 carbon atoms, the halogen atom, and the nitro group; more preferably the alkyl group having 1 to 6 carbon atoms and the alkoxy group having 1 to 6 carbon atoms; and even more preferably the alkyl group having 1 to 6 carbon atoms.

Examples of the number of substituents on the aryl group having 6 to 14 carbon atoms in the phrase "an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented as any of $R^8$ and $R^9$ in the general formula (A) include integers of 0 (no substituent) to 9. Among them, the integers of 0 (no substituent) to 5 are preferred, and the integers of 0 (no substituent) to 2 are more preferred.

The position of a substituent on the aryl group having 6 to 14 carbon atoms in the phrase "an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented as any of $R^8$ and $R^9$ in the general formula (A) depends on the aryl group and differs among the phenyl group, the naphthyl group, and the anthracenyl group, and the preferred position of a substituent also differs thereamong.

In a case where the aryl group having 6 to 14 carbon atoms in the phrase "an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented as any of $R^8$ and $R^9$ in the general formula (A) is the phenyl group, the position of a substituent on the phenyl group may be any of position 2 to position 6. Among them, the position 2, position 4, and position 6 are preferred, and the position 2 and position 6 are more preferred.

In a case where the aryl group having 6 to 14 carbon atoms in the phrase "an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented as any of $R^8$ and $R^9$ in the general formula (A) is the naphthyl group, the position of a nitrogen atom bonding to $R^8$ or $R^9$ on the naphthyl group may be position 1 or position 2.

For the naphthyl group, the position of a substituent on the naphthyl group may be any of position 1 to position 8. Among them, the position 1 to position 4 are preferred. Here, the position of a substituent does not overlap with the position of a nitrogen atom bonding to $R^8$ or $R^9$.

In a case where the aryl group having 6 to 14 carbon atoms in the phrase "an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented as any of $R^8$ and $R^9$ in the general formula (A) is the anthracenyl group, the position of a nitrogen atom bonding to $R^8$ or $R^9$ on the anthracenyl group may be position 1, position 2, or position 9. Among them, the position 9 is preferred.

For the anthracenyl group, in a case where the position of a nitrogen atom bonding to $R^8$ or $R^9$ on the anthracenyl group is position 1 or position 2, the position of a substituent on the anthracenyl group may be any of position 1 to position 10. Among them, the position 1 to position 4 are preferred. Here, the position of a substituent does not overlap with the position of a nitrogen atom bonding to $R^8$ or $R^9$.

For the anthracenyl group, in a case where the position of a nitrogen atom bonding to $R^8$ or $R^9$ on the anthracenyl group is position 9, the position of a substituent on the anthracenyl group may be any of position 1 to position 8 or position 10. Among them, the position 10 is preferred.

Specific examples of the "aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented as any of $R^8$ and $R^9$ in the general formula (A) include aryl groups having 6 to 14 carbon atoms without a substituent (unsubstituted aryl groups) such as a phenyl group, a naphthyl group, and an anthracenyl group; aryl groups having 6 to 14 carbon atoms and substituted with an alkyl group having 1 to 6 carbon atoms (aryl groups having an alkyl group having 1 to 6 carbon atoms) such as a 2-methylphenyl group, a 3-methylphenyl group, a 4-methylphenyl group, a 2,4-dimethylphenyl group, a 2,6-dimethylphenyl group, a 2,4,6-trimethylphenyl group, a 2,6-diethylphenyl group, a 2,6-di-n-propylphenyl group, a 2,6-diisopropylphenyl group, a 1-(2-methyl)naphthyl group, a 2-(1-methyl)naphthyl group, and a 9-(10-methyl)anthracenyl group; aryl groups having 6 to 14 carbon atoms and substituted with an alkoxy group having 1 to 6 carbon atoms (aryl groups having an alkoxy group having 1 to 6 carbon atoms) such as a 2-methoxyphenyl group, a 3-methoxyphenyl group, a 4-methoxyphenyl group, a 2,4-dimethoxyphenyl group, a 2,6-dimethoxyphenyl group, a 2,4,6-trimethoxyphenyl group, a 2,6-diethoxyphenyl group, a 2,6-di-n-propoxyphenyl group, a 2,6-diisopropoxyphenyl group, a 1-(2-methoxy)naphthyl group, a 2-(1-methoxy)naphthyl group, and a 9-(10-methoxy)anthracenyl group; aryl groups having 6 to 14 carbon atoms and substituted with an alkylthio group having 1 to 6 carbon atoms (aryl groups having an alkylthio group having 1 to 6 carbon atoms) such as a 2-methylthiophenyl group, a 3-methylthiophenyl group, a 4-methylthiophenyl group, a 2,4-dimethylthiophenyl group, a 2,6-dimethylthiophenyl group, a 2,4,6-trimethylthiophenyl group, a 2,6-diethylthiophenyl group, a 2,6-di-n-propylthiophenyl group, a 2,6-diisopropylthiophenyl group, a 1-(2-methylthio)naphthyl group, a 2-(1-methylthio)naphthyl group, and a 9-(10-methylthio)anthracenyl group; aryl groups having 6 to 14 carbon atoms and substituted with a dialkylamino group having 2 to 12 carbon atoms (aryl groups having a dialkylamino group having 2 to 12 carbon atoms) such as a 2-(N,N-dimethylamino)phenyl group, a 3-(N,N-dimethylamino)phenyl group, a 4-(N,N-dimethylamino)phenyl group, a 2,4-bis(N,N-dimethylamino)phenyl group, a 2,6-bis(N,N-dimethylamino)phenyl group, a 2,4,6-tris(N,N-dimethylamino)phenyl group, a 2,6-bis(N,N-diethylamino)phenyl group, a 2,6-bis(N,N-di-n-propylamino)phenyl group, a 2,6-bis(N,N-diisopropylamino)phenyl group, a 1-[2-(N,N-dimethylamino)]naphthyl group, a 2-[1-(N,N-dimethylamino)]naphthyl group, and a 9-[10-(N,N-dimethylamino)]anthracenyl group; aryl groups having 6 to 14 carbon atoms and substituted with a halogen atom (aryl groups having a halogen atom) such as a 2-fluorophenyl group, a 3-fluorophenyl group, a 4-fluorophenyl group, a 2,4-difluorophenyl group, a 2,6-difluorophenyl group, a 2,4, 6-trifluorophenyl group, a 2,6-dichlorophenyl group, a 2,6-dibromophenyl group, a 2,6-diiodophenyl group, a 1-(2-fluoro)naphthyl group, a 2-(1-fluoro)naphthyl group, and a 9-(10-fluoro)anthracenyl group; and aryl groups having 6 to 14 carbon atoms and substituted with a nitro group (aryl groups having a nitro group) such as a 2-nitrophenyl group, a 3-nitrophenyl group, a 4-nitrophenyl group, a 2,4-dinitrophenyl group, a 2,6-dinitrophenyl group, a 2,4,6-trinitrophenyl group, a 1-(2-nitro)naphthyl group, a 2-(1-nitro)naphthyl group, and a 9-(10-nitro)anthracenyl group. Among these aryl groups having 6 to 14 carbon atoms, the aryl groups having 6 to 14 carbon atoms without a substituent (unsubstituted aryl groups); the aryl groups having 6 to 14 carbon atoms and substituted with an alkyl group having 1 to 6 carbon atoms (aryl groups having an alkyl group having 1 to 6 carbon atoms); the aryl groups having 6 to 14 carbon atoms and substituted with an alkoxy group having 1 to 6 carbon atoms (aryl groups having an alkoxy group having 1 to 6 carbon atoms); the aryl groups having 6 to 14 carbon atoms and substituted with a halogen atom (aryl groups having a halogen atom); and the aryl groups having 6 to 14 carbon atoms and substituted with a nitro group (aryl groups having a nitro group) are preferred. Among them, the aryl groups having 6 to 14 carbon atoms without a substituent (unsubstituted aryl groups); the aryl groups having 6 to 14 carbon atoms and substituted with an alkyl group having 1 to 6 carbon atoms (aryl groups having an alkyl group having 1 to 6 carbon atoms); and the aryl groups having 6 to 14 carbon atoms and substituted with an alkoxy group having 1 to 6 carbon atoms (aryl groups having an alkoxy group having 1 to 6 carbon atoms) are more preferred, and the aryl groups having 6 to 14 carbon atoms without a substituent (unsubstituted aryl groups); and the aryl groups having 6 to 14 carbon atoms and substituted with an alkyl group having 1 to 6 carbon atoms (aryl groups having an alkyl group having 1 to 6 carbon atoms) are even more preferred.

The alkylene group having 2 to 4 carbon atoms in a case where "$R^8$ and $R^9$ are bonded to each other to represent an alkylene group having 2 to 4 carbon atoms" in the general formula (A) may be any of linear or branched, and specific examples of such alkylene groups include those exemplified for the alkylene group represented as any of $R^4$ and $R^5$ in the general formula (A), and the same applies preferred specific examples thereof.

In a case where "$R^8$ and $R^9$ are bonded to each other to represent an alkylene group having 2 to 4 carbon atoms" in the general formula (A), the alkylene group and a —N—C=N— group bonding to the alkylene group form a 5- to 7-membered cyclic structure.

Specific examples of the cyclic structure include an imidazoline ring, a 1,4,5,6-tetrahydropyrimidine ring, a 4-methylimidazoline ring, a 5-methylimidazoline ring, a 1,3-diaza-2-cycloheptene ring, a 4-methyl-1,4,5,6-tetrahydropyrimidine ring, a 5-methyl-1,4,5,6-tetrahydropyrimidine ring, a 6-methyl-1,4,5,6-tetrahydropyrimidine ring, a 4-ethylimidazoline ring, a 5-ethylimidazoline ring, a 4,4-dimethylimidazoline ring, a 4,5-dimethylimidazoline ring, and a 5,5-dimethylimidazoline ring. Among these cyclic structures, the imidazoline ring is preferred.

Each of $R^8$ and $R^9$ in the general formula (A) is preferably an alkyl group having 1 to 12 carbon atoms, and an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group; and more preferably an alkyl group having 1 to 12 carbon atoms.

Two or three of the eight groups represented as $R^3$ to $R^{10}$ in the general formula (A) are each a hydrogen atom, and, in a case where two of the eight groups are each a hydrogen atom, then three to six of the remaining groups are each an alkyl group having 1 to 12 carbon atoms, and, in a case where three of the eight groups are each a hydrogen atom, then four or five of the remaining groups are each an alkyl group having 1 to 12 carbon atoms. In other words, the number of alkyl groups among the eight groups represented as $R^3$ to $R^{10}$ must be larger than the number of hydrogen atoms thereamong. More specifically, in a case where two of the eight groups are each a hydrogen atom, then the number of alkyl groups must be three or more, and, in a case where three of the eight groups are each a hydrogen atom, then the number of alkyl groups must be four or more. This is because compounds having a cation derived from a biguanide in which the number of hydrogen atoms is equal to or larger than the number of alkyl groups do not exhibit sufficient basicity, and a base generated from such a compound cannot cure a base-curable resin composition, for example, containing an epoxy compounds and a polythiol.

It is preferred that two of the eight groups represented as $R^3$ to $R^{10}$ in the general formula (A) be each a hydrogen atom and four to six of the remaining groups be each an alkyl group having 1 to 12 carbon atoms. It is more preferred that the two groups $R^7$ and $R^{10}$ be each a hydrogen atom, and the four groups $R^3$ to $R^6$ be each an alkyl group having 1 to 12 carbon atoms.

Specific examples of the biguanidinium cation represented by the general formula (C) below as a partial structure of the compound represented by the general formula (A) include those represented by the formulae (C-1) to (C-19) below. It should be noted that the biguanidinium cation represented by the general formula (C) is not limited to the biguanidinium cations represented by the formulae (C-1) to (C-19) below.

General Formula (C):

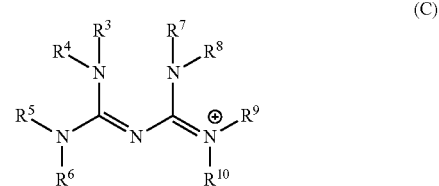

(C)

wherein $R^3$ to $R^{10}$ are as described above.

Formulae (C-1) to (C-10):

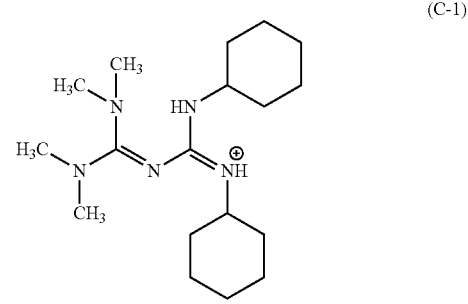

(C-1)

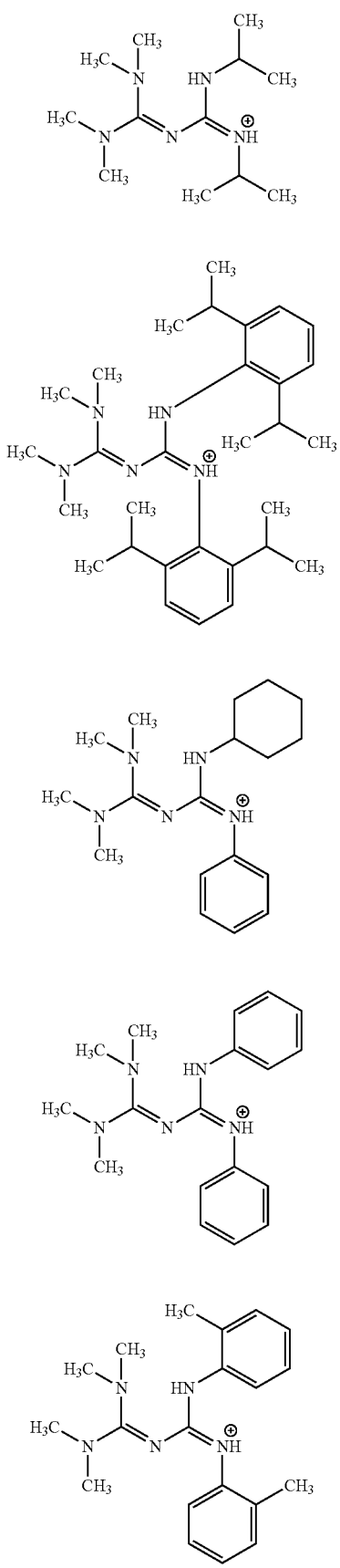
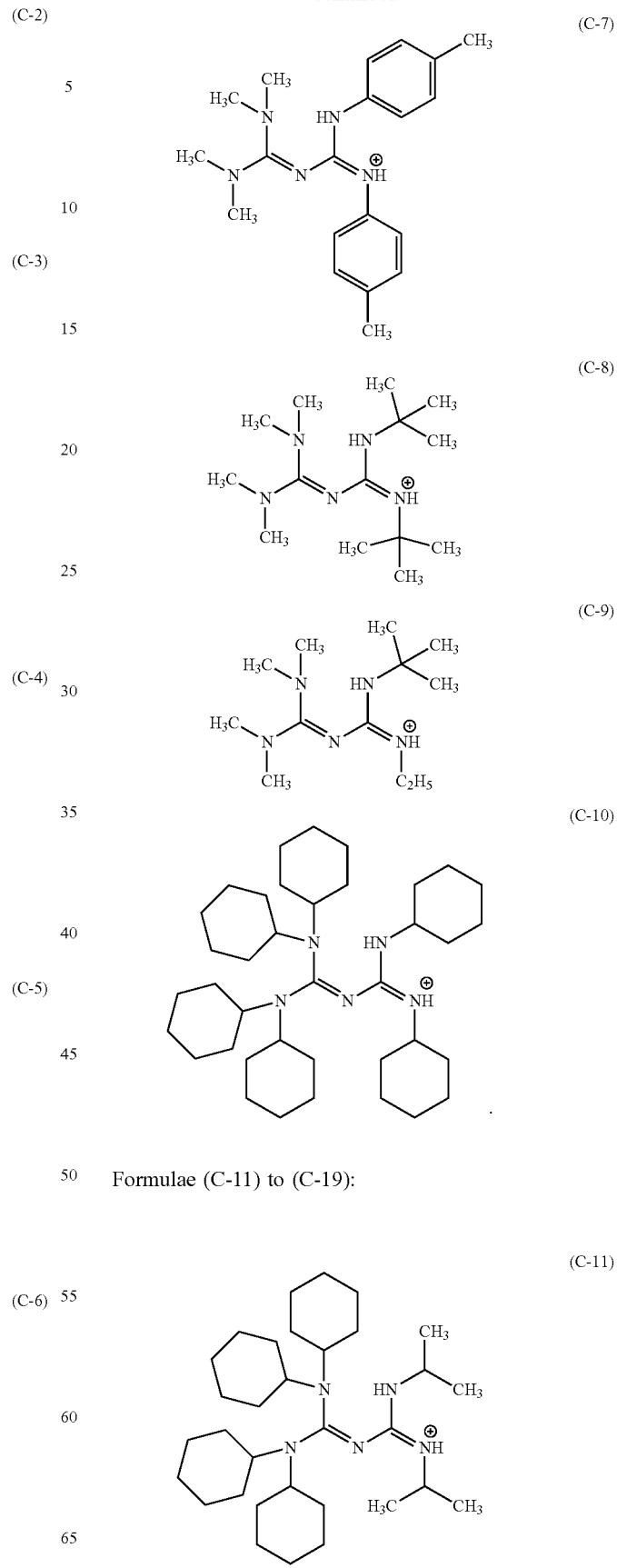
Formulae (C-11) to (C-19):

(C-12)
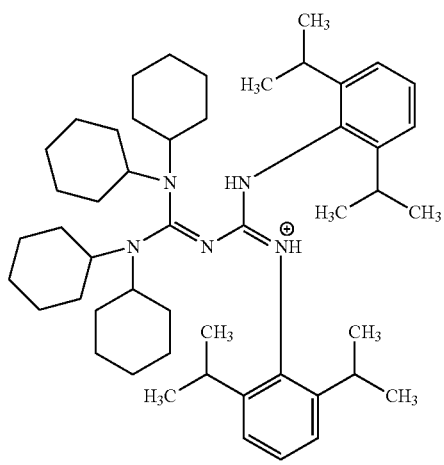

(C-13)
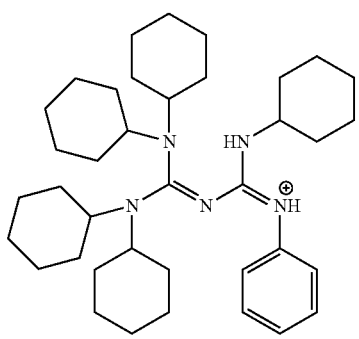

(C-14)
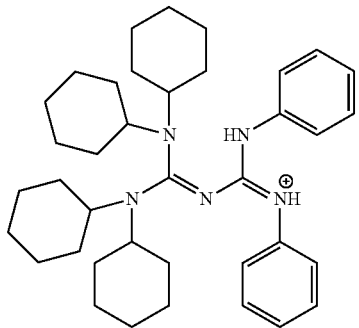

(C-15)
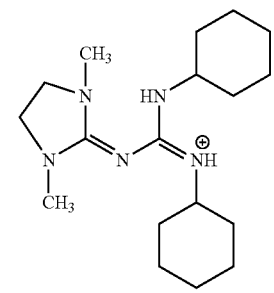

(C-16)
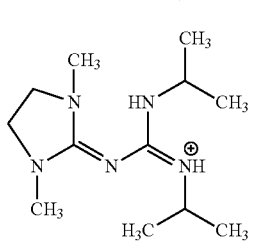

(C-17)
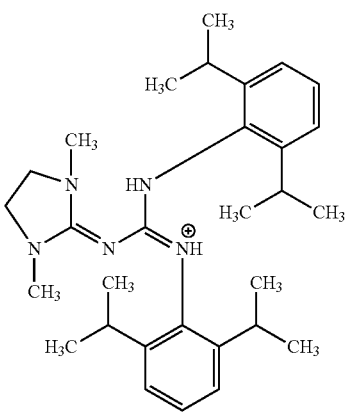

(C-18)
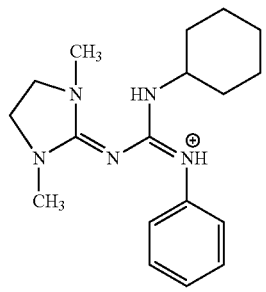

(C-19)
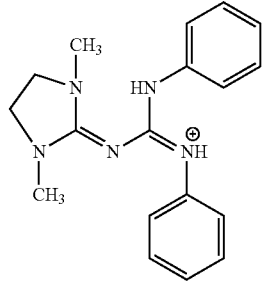

The compound of the present invention having the biguanidinium cation represented by the general formula (C) generates a strong base (a biguanide) derived from the biguanidinium cation represented by the general formula (C) through irradiation with light (an active energy ray) or heating, and hence is advantageously applicable to a curing system for an epoxy compounds, for which application of common base generators has been difficult.

Among the biguanidinium cations represented by the general formula (C), a biguanidinium cation represented by the general formula (C') below is preferred.

General Formula (C'):

(C')
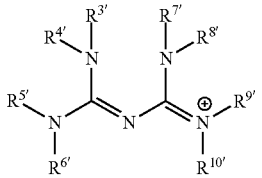

wherein $R^{3'}$ to $R^{7'}$ and $R^{10'}$ each independently represent a hydrogen atom or an alkyl group having 1 to 6 carbon atoms;

and $R^{8'}$ and $R^{9'}$ each independently represent an alkyl group having 2 to 8 carbon atoms, or a phenyl group optionally having a substituent selected from the group consisting of an alkyl group having 1 to 3 carbon atoms, an alkoxy group having 1 to 3 carbon atoms, a halogen atom, and a nitro group; provided that two or three of the eight groups $R^{3'}$ to $R^{10'}$ are each a hydrogen atom, and, in a case where two of the eight groups are each a hydrogen atom, then three to six of the remaining groups are each an alkyl group, and, in a case where three of the eight groups are each a hydrogen atom, then four or five of the remaining groups are each an alkyl group.

The alkyl group having 1 to 6 carbon atoms represented as any of $R^{3'}$ to $R^{7'}$ and $R^{10'}$ in the general formula (C') may be any of linear, branched, or cyclic, and specific examples of such alkyl groups include those exemplified for the alkyl group having 1 to 6 carbon atoms represented as any of $R^3$ to $R^7$ and $R^{10}$ in the general formula (A). Among these alkyl groups, the linear, branched, or cyclic alkyl groups having 1 to 4 carbon atoms are preferred, and the methyl group, which is an alkyl group having 1 carbon atom, is more preferred.

Alkyl groups having 1 to 6 carbon atoms are preferred for $R^{3'}$ to $R^{6'}$ in the general formula (C'), and it is more preferred that all of $R^{3'}$ to $R^{6'}$ be an alkyl group having 1 to 6 carbon atoms.

A hydrogen atom is preferred for $R^{7'}$ and $R^{10'}$ in the general formula (C'), and it is more preferred that $R^{7'}$ and $R^{10'}$ be each a hydrogen atom.

The alkyl group having 2 to 8 carbon atoms represented as any of $R^{8'}$ and $R^{9'}$ in the general formula (C') may be any of linear, branched, or cyclic, and specific examples of such alkyl groups include the alkyl groups having 2 to 8 carbon atoms exemplified as preferred specific examples of the alkyl group having 1 to 12 carbon atoms represented as any of $R^8$ and $R^9$ in the general formula (A). Among these alkyl groups, the linear, branched, or cyclic alkyl groups having 3 to 6 carbon atoms are preferred, and the branched or cyclic alkyl groups having 3 to 6 carbon atoms are more preferred.

The concept of the expression "phenyl group optionally having a substituent" in the phrase "a phenyl group optionally having a substituent selected from the group consisting of an alkyl group having 1 to 3 carbon atoms, an alkoxy group having 1 to 3 carbon atoms, a halogen atom, and a nitro group" represented as any of $R^{8'}$ and $R^{9'}$ in the general formula (C') is intended to encompass both a phenyl group having no substituent and a phenyl group having a substituent.

The alkyl group having 1 to 3 carbon atoms in the phrase "a phenyl group optionally having a substituent selected from the group consisting of an alkyl group having 1 to 3 carbon atoms, an alkoxy group having 1 to 3 carbon atoms, a halogen atom, and a nitro group" represented as any of $R^{8'}$ and $R^{9'}$ in the general formula (C') may be any of linear or branched, and specific examples of such alkyl groups include the alkyl groups having 1 to 3 carbon atoms exemplified as preferred specific examples of the alkyl group having 1 to 6 carbon atoms in the phrase "an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented as any of $R^8$ and $R^9$ in the general formula (A).

The alkoxy group having 1 to 3 carbon atoms in the phrase "a phenyl group optionally having a substituent selected from the group consisting of an alkyl group having 1 to 3 carbon atoms, an alkoxy group having 1 to 3 carbon atoms, a halogen atom, and a nitro group" represented as any of $R^{8'}$ and $R^{9'}$ in the general formula (C') may be any of linear or branched, and specific examples of such alkoxy groups include the alkoxy groups having 1 to 3 carbon atoms exemplified as preferred specific examples of the alkoxy group having 1 to 6 carbon atoms in the phrase "an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented as any of $R^8$ and $R^9$ in the general formula (A).

Specific examples of the halogen atom in the phrase "a phenyl group optionally having a substituent selected from the group consisting of an alkyl group having 1 to 3 carbon atoms, an alkoxy group having 1 to 3 carbon atoms, a halogen atom, and a nitro group" represented as any of $R^{8'}$ and $R^{9'}$ in the general formula (C') include those exemplified for the halogen atoms in the phrase "an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented as any of $R^8$ and $R^9$ in the general formula (A), and the same applies to preferred specific examples thereof.

The "substituent selected from the group consisting of an alkyl group having 1 to 3 carbon atoms, an alkoxy group having 1 to 3 carbon atoms, a halogen atom, and a nitro group" in any of $R^{8'}$ and $R^{9'}$ in the general formula (C') is preferably the alkyl group having 1 to 3 carbon atoms and the alkoxy group having 1 to 3 carbon atoms; and more preferably the alkyl group having 1 to 3 carbon atoms.

Examples of the number of substituents on the phenyl group in the phrase "a phenyl group optionally having a substituent selected from the group consisting of an alkyl group having 1 to 3 carbon atoms, an alkoxy group having 1 to 3 carbon atoms, a halogen atom, and a nitro group" represented as any of $R^{8'}$ and $R^{9'}$ in the general formula (C') include integers of 0 (no substituent) to 5. Among them, the integers of 0 (no substituent) to 2 are preferred.

The position of a substituent on the phenyl group in the phrase "a phenyl group optionally having a substituent selected from the group consisting of an alkyl group having 1 to 3 carbon atoms, an alkoxy group having 1 to 3 carbon atoms, a halogen atom, and a nitro group" represented as any of $R^{8'}$ and $R^{9'}$ in the general formula (C') may be any of position 2 to position 6. Among them, the position 2, position 4, and position 6 are preferred, and the position 2 and position 6 are more preferred.

Specific examples of the "phenyl group optionally having a substituent selected from the group consisting of an alkyl group having 1 to 3 carbon atoms, an alkoxy group having 1 to 3 carbon atoms, a halogen atom, and a nitro group" represented as any of $R^{8'}$ and $R^{9'}$ in the general formula (C') include a phenyl group without a substituent (unsubstituted phenyl group) such as a phenyl group; phenyl groups substituted with an alkyl group having 1 to 3 carbon atoms (phenyl groups having an alkyl group having 1 to 3 carbon atoms) such as a 2-methylphenyl group, a 3-methylphenyl group, a 4-methylphenyl group, a 2,4-dimethylphenyl group, a 2,6-dimethylphenyl group, a 2,4,6-trimethylphenyl group, a 2,6-diethylphenyl group, a 2,6-di-n-propylphenyl group, and a 2,6-diisopropylphenyl group; phenyl groups substituted with an alkoxy group having 1 to 3 carbon atoms (phenyl groups having an alkoxy group having 1 to 3 carbon atoms) such as a 2-methoxyphenyl group, a 3-methoxyphenyl group, a 4-methoxyphenyl group, a 2,4-dimethoxyphenyl group, a 2,6-dimethoxyphenyl group, a 2,4,6-trimethoxyphenyl group, a 2,6-diethoxyphenyl group, a 2,6-di-n-propoxyphenyl group, and a 2,6-diisopropoxyphenyl group; phenyl groups substituted with a halogen atom (phenyl groups having a halogen atom) such as a 2-fluorophenyl group, a 3-fluorophenyl group, a 4-fluorophenyl group, a 2,4-difluorophenyl group, a 2,6-difluorophenyl group, a 2,4,6-trifluorophenyl group, a 2,6-dichlorophenyl group, a 2,6-dibromophenyl group, and a 2,6-diiodophenyl group; and phenyl groups substituted with a nitro group (phenyl groups having a nitro group) such as a 2-nitrophenyl group, a 3-nitrophenyl group, a 4-nitrophenyl group, a 2,4-dinitrophenyl group, a 2,6-dinitrophenyl group, and a 2,4,6-trinitrophenyl group. Among these phenyl groups, the phenyl group without a substituent (unsubstituted phenyl group); the phenyl groups substituted with an alkyl group having 1 to 3 carbon atoms (phenyl groups having an alkyl group having 1 to 3 carbon atoms); and the phenyl groups substituted with an alkoxy group having 1 to 3 carbon atoms (phenyl groups having an alkoxy group having 1 to 3 carbon atoms) are preferred. Among them, the phenyl group without a substituent (unsubstituted phenyl group); and the phenyl groups substituted with an alkyl group having 1 to 3 carbon atoms (phenyl groups having an alkyl group having 1 to 3 carbon atoms) are more preferred.

Each of $R^{8'}$ and $R^{9'}$ in the general formula (C') is preferably an alkyl group having 2 to 8 carbon atoms.

Two or three of the eight groups represented as $R^{3'}$ to $R^{10'}$ in the general formula (C') are each a hydrogen atom, and, in a case where two of the eight groups are each a hydrogen atom, then three to six of the remaining groups are each an alkyl group, and, in a case where three of the eight groups are each a hydrogen atom, then four or five of the remaining groups are each an alkyl group. In other words, the number of alkyl groups among the eight groups represented as $R^{3'}$ to $R^{10'}$ must be larger than the number of hydrogen atoms thereamong. More specifically, in a case where two of the eight groups are each a hydrogen atom, then the number of alkyl groups must be three or more, and, in a case where three of the eight groups are each a hydrogen atom, then the number of alkyl groups must be four or more. This is because compounds having a cation derived from a biguanide in which the number of hydrogen atoms is equal to or larger than the number of alkyl groups do not exhibit sufficient basicity, and a base generated from such a compound cannot cure a base-curable resin composition, for example, containing an epoxy compounds and a polythiol.

It is preferred that two of the eight groups represented as $R^{3'}$ to $R^{10'}$ in the general formula (C') be each a hydrogen atom and four to six of the remaining groups be each an alkyl group. It is more preferred that the two groups $R^{7'}$ and $R^{10'}$ be each a hydrogen atom, and the four groups $R^{3'}$ to $R^{6'}$ be each an alkyl group having 1 to 6 carbon atoms.

Specific examples of the biguanidinium cation represented by the general formula (C') include those represented by the formulae (C-1) to (C-14).

Among the biguanidinium cations, the compound of the present invention having the biguanidinium cation represented by the general formula (C') can generate a biguanide with higher basicity through irradiation with light (an active energy ray) or heating. Thus, the compound of the present invention having the biguanidinium cation represented by the general formula (C') can advantageously provide a higher contrast ratio between an exposed portion (a portion irradiated with light) and an unexposed portion (a portion not irradiated with light) in a curing system for an epoxy compounds.

It should be noted that the compound of the present invention having the biguanidinium cation represented by the general formula (C') can be represented by the general formula (A') below.

General Formula (A'):

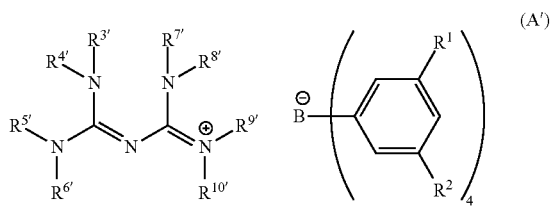

wherein four pieces of $R^1$, four pieces of $R^2$, and $R^{3'}$ to $R^{10'}$ are as described above.

In addition, specific examples of the compound of the present invention in a case where the biguanidinium cation is a cation represented by any of the formulae (C-1) to (C-3) include compounds represented by the general formulae (C-A1) to (C-A3) below.

General Formulae (C-A1) to (C-A3):

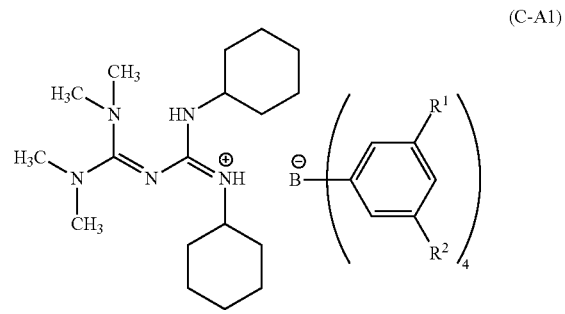

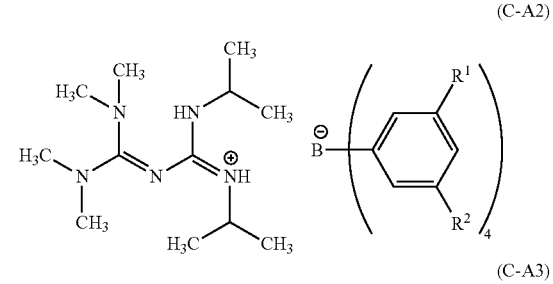

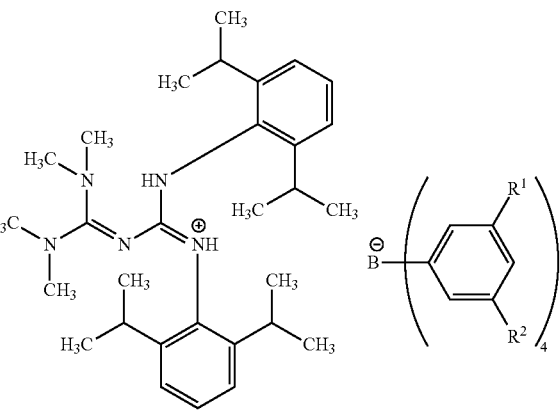

wherein four pieces of $R^1$ and four pieces of $R^2$ are as described above.

An example of compounds of the present invention of a combination of a preferred borate anion and a preferred biguanidinium cation among the compounds of the present invention is the compound represented by the general formula (A″) below.

General Formula (A″):

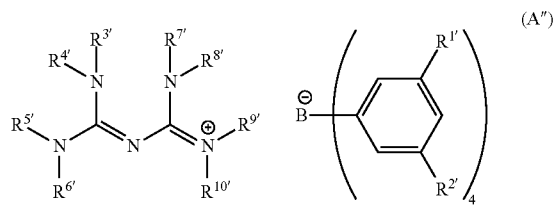

wherein four pieces of $R^1$, four pieces of $R^{2'}$ and $R^{3'}$ to $R^{10'}$ are as described above.

Specific examples of the compound represented by the general formula (A″) include those represented by the formulae (1) to (5) below. It should be noted that the compound represented by the general formula (A″) is not limited to the formulae (1) to (5) below.

Formulae (1) to (5):

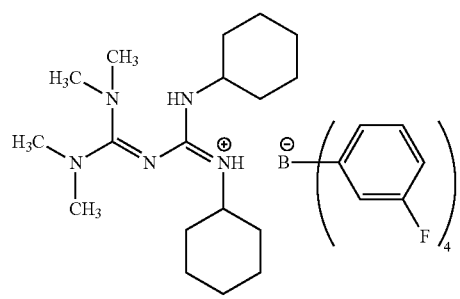

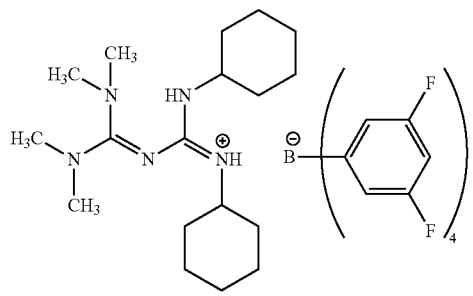

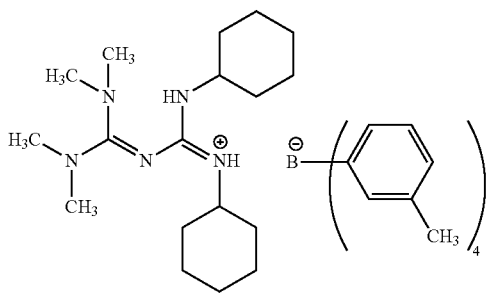

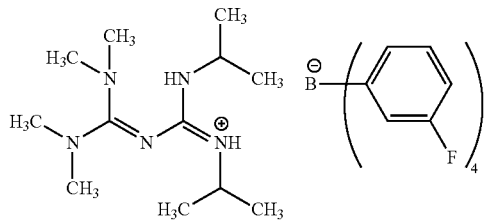

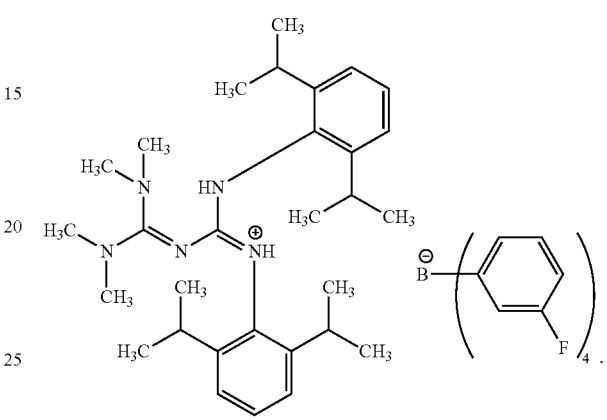

Among the compounds of the present invention, the compound represented by the general formula (A″) has even higher acid resistance, and can more quickly generate a strong base (a biguanide with high basicity) through irradiation with light (an active energy ray) or heating. Thus, even when an acidic compound such as a multivalent carboxylic acid, a polyhydric phenol, a polythiol, and a multivalent β-keto ester coexists in a curing system for an epoxy compounds, the compound represented by the general formula (A″) is less likely to cause decomposition due to the acidic compound, and, in addition, less likely to activate the acidic compound. Accordingly, a resin having a high contrast ratio can be obtained more quickly by using the compound represented by the general formula (A″) in a curing system for an epoxy compounds.

—Method for Producing Compound of the Present Invention—

The compound of the present invention can be produced, for example, by using a method as a scheme represented by [S-1] below. Specifically, the compound represented by the general formula (A) can be produced by reacting, for example, trifluoroborane represented by the formula [I] below and a Grignard reagent represented by the general formula [II] below to obtain a magnesium salt of tetraphenylborate represented by the general formula [III] below and then reacting the magnesium salt and a biguanidinium salt represented by the general formula [IV] below for salt exchange reaction. It should be noted that the biguanidinium salt represented by the general formula [IV] below can be produced not only by using a method described later, but also by reaction of a biguanidinium salt represented by the general formula [V] and a hydrogen halide represented by the general formula [IX] below.

Scheme [S-1]:

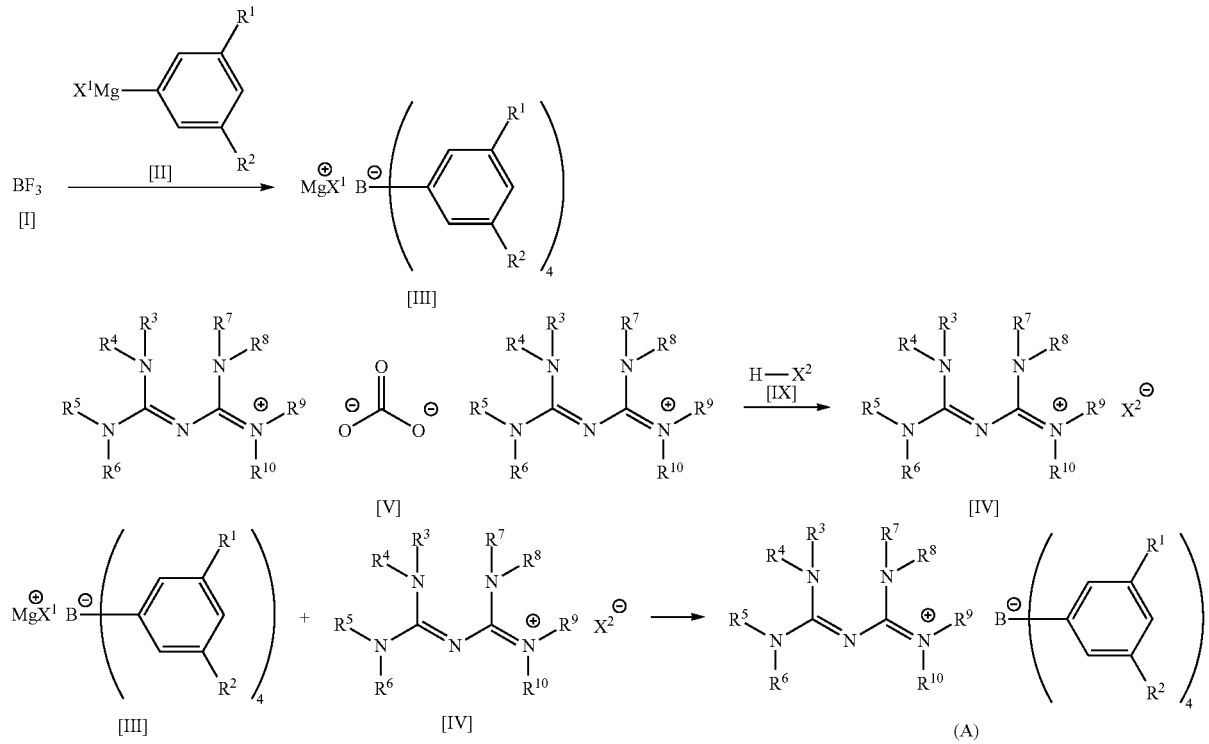

wherein $X^1$ and $X^2$ each independently represent a halogen atom, $X^{2-}$ represents a halide ion, and $R^1$ to $R^{10}$ are as described above.

Examples of the halogen atom represented as $X^1$ in the general formulae [11] and [III] include a chlorine atom, a bromine atom, and an iodine atom. Among them, the bromine atom and the iodine atom are preferred, and the bromine atom is more preferred.

Examples of the halogen atom represented as $X^2$ in the general formula [IX] include a chlorine atom, a bromine atom, and an iodine atom. Among them, the chlorine atom is preferred.

Examples of the halide ion represented as $X^{2-}$ in the general formula [IV] include a chloride ion, a bromide ion, and an iodide ion. Among them, the chloride ion is preferred.

A commercially available product can be suitably used for trifluoroborane represented by the formula [I] in the method for producing the compound of the present invention. Examples of commercially available trifluoroborane include trifluoroborane-diethyl ether complex.

A commercially available product or a product appropriately synthesized by using a known method can be suitably used for the Grignard reagent represented by the general formula [II] in the method for producing the compound of the present invention. Specific examples of the Grignard reagent represented by the general formula [II] include 3-fluorophenylmagnesium chloride, 3-fluorophenylmagnesium bromide, 3-fluorophenylmagnesium iodide, 3-trifluoromethylphenylmagnesium chloride, 3-trifluoromethylphenylmagnesium bromide, 3-trifluoromethylphenylmagnesium iodide, 3,5-difluorophenylmagnesium chloride, 3,5-difluorophenylmagnesium bromide, 3,5-difluorophenylmagnesium iodide, 3-fluoro-5-trifluoromethylphenylmagnesium chloride, 3-fluoro-5-trifluoromethylphenylmagnesium bromide, and 3-fluoro-5-trifluoromethylphenylmagnesium iodide.

A commercially available product or a product appropriately synthesized by using a method described later can be suitably used for the biguanidinium salt represented by the general formula [IV] in the method for producing the compound of the present invention. Specific examples of the biguanidinium salt represented by the general formula [IV] include salts of any of the biguanidinium cations represented by the formulae (C-1) to (C-19) and a chloride ion, salts of any of the biguanidinium cations represented by the formulae (C-1) to (C-19) and a bromide ion, and salts of any of the biguanidinium cations represented by the formulae (C-1) to (C-19) and an iodide ion.

A commercially available product or a product appropriately synthesized by using a method described later can be suitably used for the biguanidinium salt represented by the general formula [V] in the method for producing the compound of the present invention. Specific examples of the biguanidinium salt represented by the general formula [V] include salts of any of the biguanidinium cations represented by the formulae (C-1) to (C-19) and a carbonate ion.

A commercially available aqueous solution of a hydrogen halide or a product obtained by appropriately diluting a commercially available aqueous solution of a hydrogen halide can be suitably used for the hydrogen halide represented by the general formula [IX] in the method for producing the compound of the present invention. Specific examples of the hydrogen halide include hydrogen chloride, hydrogen bromide, and hydrogen iodide. Among them, the hydrogen chloride is preferred. Specific examples of commercially available aqueous solutions of the hydrogen halide include hydrochloric acid, hydrobromic acid, and hydroiodic acid.

The quantity of the Grignard reagent represented by the general formula [II] to be used in the method for producing the compound of the present invention may be, without any limitation, any quantity typically employed in the field, and, for example, the quantity is typically 3.5 to 20 equivalents, preferably 3.8 to 10 equivalents, and more preferably 4 to 6 equivalents, with respect to the number of moles of trifluoroborane represented by the formula [I]. If the quantity of the Grignard reagent used is extremely small, the yield of the magnesium salt of tetraphenylborate represented by the general formula [III] may be lower. If the quantity of the Grignard reagent used is very large, on the other hand, problems arise, such as the possibility of the occurrence of a side reaction and deterioration of the economic efficiency.

The quantity of the biguanidinium salt represented by the general formula [IV] to be used in the method for producing the compound of the present invention may be, without any limitation, any quantity typically employed in the field, and, for example, the quantity is typically 0.8 to 10 equivalents, preferably 0.9 to 5 equivalents, and more preferably 1 to 2 equivalents, with respect to the number of moles of the magnesium salt of tetraphenylborate represented by the general formula [III]. If the quantity of the biguanidinium salt used is extremely small, the yield of the compound of the present invention (the compound represented by the general formula (A)) may be lower. If the quantity of the biguanidinium salt used is very large, on the other hand, problems arise, such as the possibility of the occurrence of a side reaction and deterioration of the economic efficiency.

The quantity of the hydrogen halide represented by the general formula [IX] to be used in the method for producing the compound of the present invention may be, without any limitation, any quantity typically employed in the field, and, for example, the quantity is typically 1 to 20 equivalents, preferably 1.6 to 10 equivalents, and more preferably 2 to 4 equivalents, with respect to the number of moles of the biguanidinium salt represented by the general formula [V]. If the quantity of the hydrogen halide used is extremely small, the yield of the compound of the present invention (the compound represented by the general formula (A)) may be lower. If the quantity of the hydrogen halide used is very large, on the other hand, problems arise, such as the possibility of the occurrence of a side reaction and deterioration of the economic efficiency.

It is desirable to perform a series of the reactions represented by the scheme [S-1] in an organic solvent. The organic solvent may be, without any limitation, any organic solvent which does not react with any of trifluoroborane represented by the formula [I], the Grignard reagent represented by the general formula [II], the magnesium salt of tetraphenylborate represented by the general formula [III], the biguanidinium salt represented by the general formula [IV], the biguanidinium salt represented by the general formula [V], and the hydrogen halide represented by the general formula [IX], and specific examples of the organic solvent include aliphatic hydrocarbon solvents such as hexane, heptane, and octane; aromatic hydrocarbon solvents such as benzene, toluene, ethynyltoluene, and xylene; halogen-containing solvents such as dichloromethane, trichloromethane (chloroform), and tetrachloromethane (carbon tetrachloride); ether solvents such as diethyl ether, diisopropyl ether, tert-butyl methyl ether, cyclopentyl methyl ether, tetrahydrofuran, 2-methyltetrahydrofuran, and 1,4-dioxane; and glycol ether solvents such as ethylene glycol dimethyl ether, propylene glycol dimethyl ether, ethylene glycol diethyl ether, propylene glycol diethyl ether, diethylene glycol dimethyl ether, dipropylene glycol dimethyl ether, and dipropylene glycol diethyl ether. The organic solvents may be used singly or in combinations of two or more. It should be noted that a commercially available product can be suitably used for the organic solvent.

The quantity of the organic solvent to be used may be, without any limitation, any quantity typically employed in the field, and, for example, the quantity is typically 0.01 to 500 L, and preferably 0.1 to 100 L, with respect to 1 mol of trifluoroborane represented by the formula [I] or 1 mol of the magnesium salt of tetraphenylborate represented by the general formula [III].

It is desirable to perform a series of the reactions represented by the scheme [S-1] under conditions (reaction temperature, pressure, reaction time) as shown below.

It is desirable to set the temperature (reaction temperature) in the reaction of trifluoroborane represented by the formula [I] and the Grignard reagent represented by the general formula [II] to a temperature such that trifluoroborane and the Grignard reagent efficiently react together and the magnesium salt of tetraphenylborate represented by the general formula [III] can be obtained in a favorable yield. Specifically, the temperature is, for example, typically 0 to 120° C., and preferably 20 to 100° C.

It is desirable to set the temperature (reaction temperature) in the reaction of the magnesium salt of tetraphenylborate represented by the general formula [III] and the biguanidinium salt represented by the general formula [IV] to a temperature such that the magnesium salt of tetraphenylborate and the biguanidinium salt efficiently react together and the compound of the present invention (the compound represented by the general formula (A)) can be obtained in a favorable yield. Specifically, the temperature is, for example, typically −20 to 120° C., and preferably 0 to 80° C.

It is desirable to set the temperature (reaction temperature) in the reaction of the biguanidinium salt represented by the general formula [V] and the hydrogen halide represented by the general formula [IX] to a temperature such that the biguanidinium salt represented by the general formula [V] and the hydrogen halide efficiently react together and the biguanidinium salt represented by the general formula [IV] can be obtained in a favorable yield. Specifically, the temperature is, for example, typically −20 to 120° C., and preferably 0 to 80° C.

The pressure in a series of the reactions represented by the scheme [S-1] may be, without any limitation, any pressure allowing smooth progression of a series of the reactions, and, for example, a series of the reactions can be suitably performed under normal pressure.

The reaction time in a series of the reactions represented by the scheme [S-1] may be affected by the kinds of the Grignard reagent and the biguanidinium salt, the quantities of the reagent and the salt to be used, the presence or absence of the organic solvent and the kind thereof, the reaction temperature, the pressure in reaction, and so on. Although desirable reaction time thus depends on the situation, the reaction time is, for example, typically 1 minute to 24 hours, and preferably 3 minutes to 12 hours.

The magnesium salt of tetraphenylborate represented by the general formula [μl] may be temporarily taken out as a state of solution, or may be subjected to the reaction with the biguanidinium salt represented by the general formula [IV] in the next step without being taken out.

The compound of the present invention (the compound represented by the general formula (A)) can be isolated by using a post-treatment operation and purification operation typically performed in the field. Specific examples of the isolation method include a method in which an organic solvent such as ethyl acetate is added to the reaction solution after the completion of the reactions, the reaction solution is extracted, and the organic layer after the extraction is concentrated. In addition, as necessary, the reaction solution after the completion of the reactions may be filtered, or the organic layer after the extraction may be washed with water or the like, or the residue obtained by the concentration of the organic layer may be subjected to recrystallization, distillation, column chromatography, etc., to isolate the product.

The biguanidinium salt represented by the general formula [IV] in the method for producing the compound of the present invention (the compound represented by the general formula (A)) can be produced, for example, by using a method as a scheme represented by [S-2] below. Specifically, the biguanidinium salt represented by the general formula [IV] can be produced by using any of the following three methods 1. to 3.

1. A compound represented by the general formula [IV] where $R^7$ and $R^{10}$ are each a hydrogen atom, and $R^8$ and $R^9$ are not forming an alkylene group having 2 to 4 carbon atoms (a compound represented by the general formula [IV$_a$] below): a method in which a guanidine derivative or imidazolidine derivative represented by the general formula [VI] below is reacted with a carbodiimide derivative represented by the general formula [VII] below to obtain a compound represented by the general formula [VIII] below, and then the compound represented by the general formula [VIII] and a hydrogen halide represented by the general formula [IX] below are reacted together.

2. A compound represented by the general formula [IV] where any one of $R^7$ and $R^{10}$ is not a hydrogen atom and the other is a hydrogen atom, and $R^8$ and $R^9$ are not forming an alkylene group having 2 to 4 carbon atoms (a compound represented by the general formula [IV$_b$] below): a method in which a guanidine derivative or imidazolidine derivative represented by the general formula [VI] below is reacted with a carbodiimide derivative represented by the general formula [VII] below to obtain a compound represented by the general formula [VIII] below, and then the compound represented by the general formula [VIII] is reacted with an alkyl halide represented by the general formula [X] below in the presence of a base to obtain a compound represented by the general formula [XI] below, and thereafter the compound represented by the general formula [XI] and a hydrogen halide represented by the general formula [IX] below are reacted together.

3. A compound represented by the general formula [IV] where $R^7$ and $R^{10}$ are each not a hydrogen atom, or where $R^8$ and $R^9$ are forming an alkylene group having 2 to 4 carbon atoms (a compound represented by the general formula [IV$_c$] below): a method in which a guanidine derivative or imidazolidine derivative represented by the general formula [VI] below and a compound represented by the general formula [XII] below are reacted together.

Scheme [S-2]:

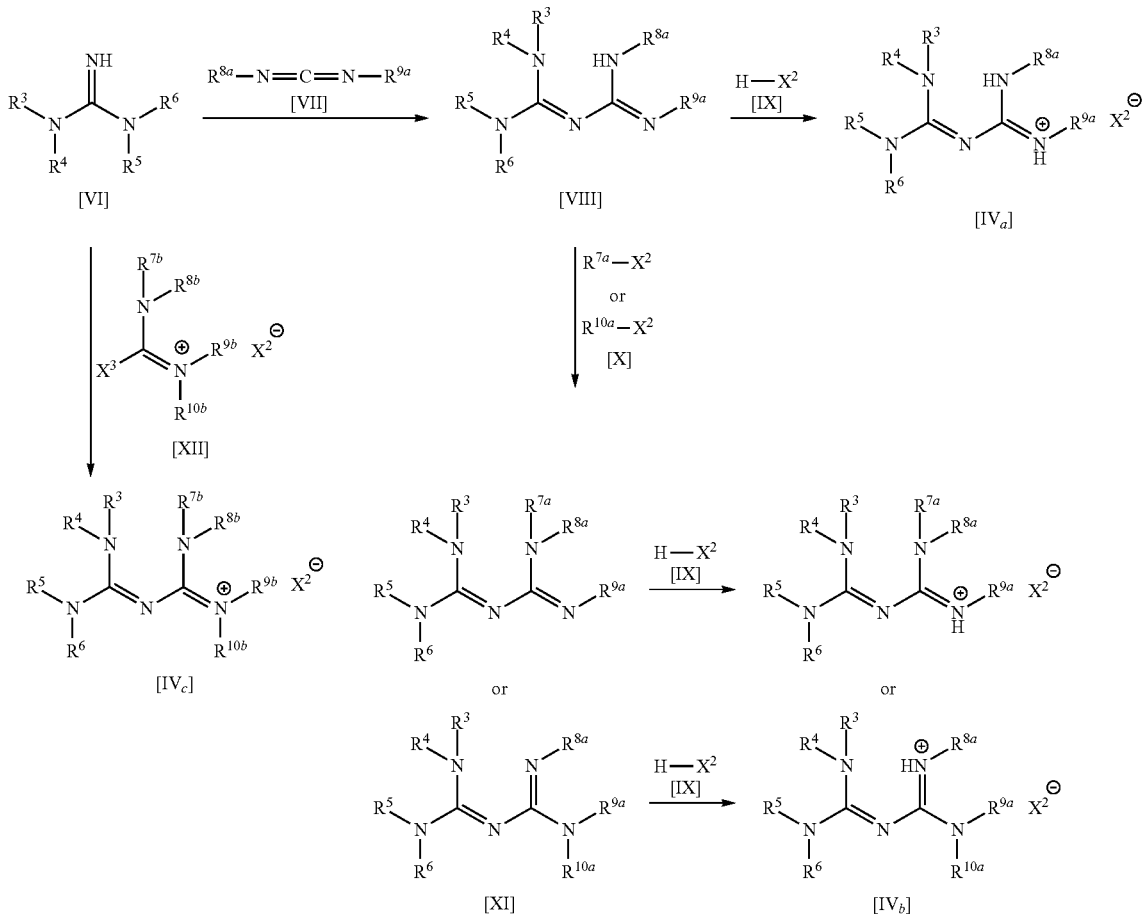

wherein $R^{7a}$ and $R^{10a}$ each independently represent an alkyl group having 1 to 12 carbon atoms; $R^{8a}$ and $R^{9a}$ each independently represent a hydrogen atom, an alkyl group having 1 to 12 carbon atoms, or an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group; (i) $R^{7b}$ and $R^{10b}$ each independently represent an alkyl group having 1 to 12 carbon atoms; and $R^{8b}$ and $R^{9b}$ each independently represent a hydrogen atom, an alkyl group having 1 to 12 carbon atoms, or an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group; or (ii) $R^{7b}$ and $R^{10b}$ each independently represent a hydrogen atom or an alkyl group having 1 to 12 carbon atoms, and $R^{8b}$ and $R^{9b}$ are bonded together to represent an alkylene group having 2 to 4 carbon atoms; and $R^3$ to $R^6$, $X^2$, and $X^{2-}$ are as described above; provided that none or one of the six groups $R^3$ to $R^6$, $R^{8a}$, and $R^{9a}$ in the general formula [$IV_a$] is a hydrogen atom, and, in a case where the six groups are each not a hydrogen atom (in a case where none of the six groups is a hydrogen atom), then three to six of the six groups are each an alkyl group having 1 to 12 carbon atoms, and, in a case where one of the six groups is a hydrogen atom, then four or five of the remaining groups are each an alkyl group having 1 to 12 carbon atoms; provided that one or two of the seven groups $R^3$ to $R^6$ and $R^{7a}$ to $R^{9a}$ or $R^{8a}$ to $R^{10a}$ are each a hydrogen atom in the general formula [$IV_b$], and, in a case where one of the seven groups is a hydrogen atom, then three to six of the remaining groups are each an alkyl group having 1 to 12 carbon atoms, and, in a case where two of the seven groups are each a hydrogen atom, then four or five of the remaining groups are each an alkyl group having 1 to 12 carbon atoms; and provided that two or three of the eight groups $R^3$ to $R^6$ and $R^{7b}$ to $R^{10b}$ are each a hydrogen atom in the general formula [$IV_c$], and, in a case where two of the eight groups are each a hydrogen atom, then three to six of the remaining groups are each an alkyl group having 1 to 12 carbon atoms, and, in a case where three of the eight groups are each a hydrogen atom, then four or five of the remaining groups are each an alkyl group having 1 to 12 carbon atoms.

Specific examples of each of the functional groups (the alkyl group having 1 to 12 carbon atoms, the alkyl group having 1 to 6 carbon atoms, the alkoxy group having 1 to 6 carbon atoms, the alkylthio group having 1 to 6 carbon atoms, the dialkylamino group having 2 to 12 carbon atoms, the halogen atom, the aryl group having 6 to 14 carbon atoms, the alkylene group having 2 to 4 carbon atoms) represented as $R^{7a}$, $R^{8a}$, $R^{9a}$, $R^{10a}$, $R^{7b}R^{8b}$, $R^{9b}$, and $R^{10b}$ in the general formulae [VII], [VIII], [X], [XI], [XII], [$IV_a$], [$IV_b$], and [$IV_c$] include those exemplified for the functional groups represented as $R^7$, $R^8$, $R^9$, and $R^{10}$ in the general formula (A). The same applies to preferred specific examples thereof.

None or one of the six groups represented as $R^3$ to $R^6$, $R^{8a}$, and $R^{9a}$ in the general formula [$IV_a$] is a hydrogen atom, and, in a case where the six groups are each not a hydrogen atom (in a case where none of the six groups is a hydrogen atom), then three to six of the six groups are each an alkyl group having 1 to 12 carbon atoms, and, in a case where one of the six groups is a hydrogen atom, then four or five of the remaining groups are each an alkyl group having 1 to 12 carbon atoms. In other words, the number of alkyl groups bonding to nitrogen atoms must be larger than the number of hydrogen atoms bonding to nitrogen atoms in the general formula [$IV_a$]. More specifically, in a case where one of the six groups represented as $R^3$ to $R^6$, $R^{8a}$, and $R^{9a}$ is a hydrogen atom, then the number of alkyl groups must be four or more, and, in a case where the six groups are each not a hydrogen atom (in a case where none of the six groups is a hydrogen atom), then the number of alkyl groups must be three or more, since two hydrogen atoms are bonding to nitrogen atoms in the general formula [$IV_a$].

It is preferred that the six groups represented as $R^3$ to $R^6$, $R^{8a}$, and $R^{9a}$ in the general formula [$IV_a$] be each not a hydrogen atom and four to six of the six groups be each an alkyl group having 1 to 12 carbon atoms. It is more preferred that the two groups $R^{8a}$ and $R^{9a}$ be each an alkyl group having 1 to 12 carbon atoms, or an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group; and the four groups $R^3$ to $R^6$ be each an alkyl group having 1 to 12 carbon atoms.

One or two of seven groups of $R^3$ to $R^6$ and $R^{7a}$ to $R^{9a}$ or $R^{8a}$ to $R^{10a}$ in the general formula [$IV_b$] are each a hydrogen atom, and, in a case where one of the seven groups is a hydrogen atom, then three to six of the remaining groups are each an alkyl group having 1 to 12 carbon atoms, and, in a case where two of the seven groups are each a hydrogen atom, then four or five of the remaining groups are each an alkyl group having 1 to 12 carbon atoms. In other words, the number of alkyl groups bonding to nitrogen atoms must be larger than the number of hydrogen atoms bonding to nitrogen atoms in the general formula [$IV_b$]. More specifically, in a case where one of seven groups of $R^3$ to $R^6$ and $R^{7a}$ to $R^{9a}$ or $R^{8a}$ to $R^{10a}$ is a hydrogen atom, then the number of alkyl groups must be three or more, and, in a case where two of the seven groups are each a hydrogen atom, then the number of alkyl groups must be four or more, since one hydrogen atom is bonding to a nitrogen atom in the general formula [$IV_b$].

It is preferred that one of seven groups represented as $R^3$ to $R^6$ and $R^{7a}$ to $R^{9a}$ or $R^{8a}$ to $R^{10a}$ in the general formula [$IV_b$] be a hydrogen atom and four to six of the remaining groups be each an alkyl group having 1 to 12 carbon atoms. It is more preferred that one of the two groups $R^{8a}$ and $R^{9a}$ be a hydrogen atom, and the four groups $R^3$ to $R^6$ be each an alkyl group having 1 to 12 carbon atoms.

Two or three of the eight groups represented as $R^3$ to $R^6$ and $R^{7b}$ to $R^{10b}$ in the general formula [$IV_c$] are each a hydrogen atom, and, in a case where two of the eight groups are each a hydrogen atom, then three to six of the remaining groups are each an alkyl group having 1 to 12 carbon atoms, and, in a case where three of the eight groups are each a hydrogen atom, then four or five of the remaining groups are each an alkyl group having 1 to 12 carbon atoms. In other words, the number of alkyl groups among the eight groups represented as $R^3$ to $R^6$ and $R^{7b}$ to $R^{10b}$ in the general formula [$IV_c$] must be larger than the number of hydrogen atoms thereamong. More specifically, in a case where two of the eight groups are each a hydrogen atom, then the number of alkyl groups must be three or more, and, in a case where three of the eight groups are each a hydrogen atom, then the number of alkyl groups must be four or more.

It is preferred that two of the eight groups represented as $R^3$ to $R^6$ and $R^{7b}$ to $R^{10b}$ in the general formula [IV$_c$] be each a hydrogen atom and four to six of the remaining groups be each an alkyl group having 1 to 12 carbon atoms. It is more preferred that the two groups $R^{7b}$ and $R^{10b}$ be each a hydrogen atom; or the two groups $R^{8b}$ and $R^{9b}$ be each a hydrogen atom, and the four groups $R^3$ to $R^6$ be each an alkyl group having 1 to 12 carbon atoms.

A commercially available product or a product appropriately synthesized by using a known method can be suitably used for the guanidine derivative or imidazolidine derivative represented by the general formula [VI] in the method for producing the biguanidinium salt represented by the general formula [IV]. Specific examples of the guanidine derivative or imidazolidine derivative represented by the general formula [VI] include 1,1,3,3-tetramethylguanidine (TMG), 1,1,3,3-tetraethylguanidine, 1,1,3,3-tetra-n-propylguanidine, 1,1,3,3-tetraisopropylguanidine, 1,1,3,3-tetra-n-butylguanidine, 1,1,3,3-tetraisobutylguanidine, 1,1,3,3-tetra-sec-butylguanidine, 1,1,3,3-tetra-tert-butylguanidine, 1,1,3,3-tetracyclobutylguanidine, 1,1,3,3-tetra-n-pentylguanidine, 1,1,3,3-tetraisopentylguanidine, 1,1,3,3-tetra-sec-pentylguanidine, 1,1,3,3-tetra-tert-pentylguanidine, 1,1,3,3-tetraneopentylguanidine, 1,1,3,3-tetracyclopentylguanidine, 1,1,3,3-tetra-n-hexylguanidine, 1,1,3,3-tetraisohexylguanidine, 1,1,3,3-tetra-sec-hexylguanidine, 1,1,3,3-tetra-tert-hexylguanidine, 1,1,3,3-tetraneohexylguanidine, 1,1,3,3-tetracyclohexylguanidine, 1,1,3,3-tetra-n-heptylguanidine, 1,1,3,3-tetraisoheptylguanidine, 1,1,3,3-tetra-sec-heptylguanidine, 1,1,3,3-tetra-tert-heptylguanidine, 1,1,3,3-tetraneoheptylguanidine, 1,1,3,3-tetracycloheptylguanidine, 1,1,3,3-tetra-n-octylguanidine, 1,1,3,3-tetraisooctylguanidine, 1,1,3,3-tetra-sec-octylguanidine, 1,1,3,3-tetra-tert-octylguanidine, 1,1,3,3-tetraneooctylguanidine, 1,1,3,3-tetracyclooctylguanidine, 1,1,3,3-tetra-n-nonylguanidine, 1,1,3,3-tetraisononylguanidine, 1,1,3,3-tetra-sec-nonylguanidine, 1,1,3,3-tetra-tert-nonylguanidine, 1,1,3,3-tetraneononylguanidine, 1,1,3,3-tetracyclononylguanidine, 1,1,3,3-tetra-n-decylguanidine, 1,1,3,3-tetraisodecylguanidine, 1,1,3,3-tetra-sec-decylguanidine, 1,1,3,3-tetra-tert-decylguanidine, 1,1,3,3-tetraneodecylguanidine, 1,1,3,3-tetracyclodecylguanidine, 1,1,3,3-tetra-n-undecylguanidine, 1,1,3,3-tetracycloundecylguanidine, 1,1,3,3-tetra-n-dodecylguanidine, 1,1,3,3-tetracyclododecylguanidine, 1,1,3,3-tetranorbornylguanidine, 1,1,3,3-tetrabornylguanidine, 1,1,3,3-tetramenthylguanidine, 1,1,3,3-tetraadamantylguanidine, 1,1,3,3-tetra(decahydronaphthyl)guanidine, and 1,3-dimethyl-2-iminoimidazolidine.

A commercially available product or a product appropriately synthesized by using a known method described in, for example, Tetrahedron Lett., 51, 1019-1021 (2010) can be suitably used for the carbodiimide derivative represented by the general formula [VII] in the method for producing the biguanidinium salt represented by the general formula [IV]. Examples of the carbodiimide derivative represented by the general formula [VII] include N,N'-dialkylcarbodiimides, N,N'-diarylcarbodiimides optionally having a substituent on the aryl group, and N-alkyl-N'-arylcarbodiimides optionally having a substituent on the aryl group.

Specific examples of the N,N'-dialkylcarbodiimides include N,N'-dimethylcarbodiimide, N,N'-diethylcarbodiimide, N,N'-di(n-propyl)carbodiimide, N,N'-diisopropylcarbodiimide, N-tert-butyl-N'-ethylcarbodiimide, N,N'-di(n-butyl)carbodiimide, N,N'-diisobutylcarbodiimide, N,N'-di(sec-butyl)carbodiimide, N,N'-di(tert-butyl)carbodiimide, N,N'-dicyclobutylcarbodiimide, N,N'-di(n-pentyl)carbodiimide, N,N'-diisopentylcarbodiimide, N,N'-di(sec-pentyl)carbodiimide, N,N'-di(tert-pentyl)carbodiimide, N,N'-dineopentylcarbodiimide, N,N'-di(2-methylbutyl)carbodiimide, N,N'-di(1,2-dimethylpropyl)carbodiimide, N,N'-di(1-ethylpropyl)carbodiimide, N,N'-dicyclopentylcarbodiimide, N,N'-di(n-hexyl)carbodiimide, N,N'-diisohexylcarbodiimide, N,N'-di(sec-hexyl)carbodiimide, N,N'-di(tert-hexyl)carbodiimide, N,N'-dineohexylcarbodiimide, N,N'-di(2-methylpentyl)carbodiimide, N,N'-di(1,2-dimethylbutyl)carbodiimide, N,N'-di(2,3-dimethylbutyl)carbodiimide, N,N'-di(1-ethylbutyl)carbodiimide, and N,N'-dicyclohexylcarbodiimide.

Specific examples of the N,N'-diarylcarbodiimides optionally having a substituent on the aryl group include N,N'-diphenylcarbodiimide, N,N'-bis(2-methylphenyl)carbodiimide, N,N'-bis(3-methylphenyl)carbodiimide, N,N'-bis(4-methylphenyl)carbodiimide, N,N'-bis(4-ethylphenyl)carbodiimide, N,N'-bis(4-n-propylphenyl)carbodiimide, N,N'-bis(4-isopropylphenyl)carbodiimide, N,N'-bis(4-n-butylphenyl)carbodiimide, N,N'-bis(4-n-pentylphenyl)carbodiimide, N,N'-bis(4-n-hexylphenyl)carbodiimide, N,N'-bis(2,3-dimethylphenyl)carbodiimide, N,N'-bis(3,4-dimethylphenyl)carbodiimide, N,N'-bis(2,4-dimethylphenyl)carbodiimide, N,N'-bis(2,6-dimethylphenyl)carbodiimide, N,N'-bis(2,4,6-trimethylphenyl)carbodiimide, N,N'-bis(2,3-diethylphenyl)carbodiimide, N,N'-bis(3,4-diethylphenyl)carbodiimide, N,N'-bis(2,4-diethylphenyl)carbodiimide, N,N'-bis(2,6-diethylphenyl)carbodiimide, N,N'-bis(2,4,6-triethylphenyl)carbodiimide, N,N'-bis{2,3-di(n-propyl)phenyl}carbodiimide, N,N'-bis{2,4-di(n-propyl)phenyl}carbodiimide, N,N'-bis{3,4-di(n-propyl)phenyl}carbodiimide, N,N'-bis{2,6-di(n-propyl)phenyl}carbodiimide, N,N'-bis{2,4,6-tri(n-propyl)phenyl}carbodiimide, N,N'-bis(2,3-diisopropylphenyl)carbodiimide, N,N'-bis(3,4-diisopropylphenyl)carbodiimide, N,N'-bis(2,4-diisopropylphenyl)carbodiimide, N,N'-bis(2,6-diisopropylphenyl)carbodiimide, N,N'-bis(2,4,6-triisopropylphenyl)carbodiimide, N,N'-bis{2,3-di(n-butyl)phenyl}carbodiimide, N,N'-bis{2,4-di(n-butyl)phenyl}carbodiimide, N,N'-bis{3,4-di(n-butyl)phenyl}carbodiimide, N,N'-bis{2,6-di(n-butyl)phenyl}carbodiimide, N,N'-bis{2,4,6-tri(n-butyl)phenyl}carbodiimide, N,N'-bis(2,3-diisobutylphenyl)carbodiimide, N,N'-bis(3,4-diisobutylphenyl)carbodiimide, N,N'-bis(2,4-diisobutylphenyl)carbodiimide, N,N'-bis(2,6-diisobutylphenyl)carbodiimide, N,N'-bis(2,4,6-triisobutylphenyl)carbodiimide, N,N'-bis{2,3-di(sec-butyl)phenyl}carbodiimide, N,N'-bis{2,4-di(sec-butyl)phenyl}carbodiimide, N,N'-bis{3,4-di(sec-butyl)phenyl}carbodiimide, N,N'-bis{2,6-di(sec-butyl)phenyl}carbodiimide, N,N'-bis{2,4,6-tri(sec-butyl)phenyl}carbodiimide, N,N'-bis{2,3-di(tert-butyl)phenyl}carbodiimide, N,N'-bis{2,4-di(tert-butyl)phenyl}carbodiimide, N,N'-bis{3,4-di(tert-butyl)phenyl}carbodiimide, N,N'-bis{2,6-di(tert-butyl)phenyl}carbodiimide, N,N'-bis{2,4,6-tri(tert-butyl)phenyl}carbodiimide, N,N'-bis(2,3-dicyclobutylphenyl)carbodiimide, N,N'-bis(3,4-dicyclobutylphenyl)carbodiimide, N,N'-bis(2,4-dicyclobutylphenyl)carbodiimide, N,N'-bis(2,6-dicyclobutylphenyl)carbodiimide, N,N'-bis(2,4,6-tricyclobutylphenyl)carbodiimide, N,N'-bis(4-methoxyphenyl)carbodiimide, N,N'-bis(4-methylthiophenyl)carbodiimide, N,N'-bis{4-(N,N'-dimethylamino)phenyl}carbodiimide, N,N'-bis(4-fluorophenyl)carbodiimide, N,N'-bis(4-chlorophenyl)carbodiimide, N,N'-bis(4-bromophenyl)carbodiimide, N,N'-bis(4-iodophenyl)carbodiimide, N,N'-bis(2-nitrophenyl)carbodiimide, N,N'-bis(3-nitrophenyl)carbodiimide, N,N'- bis(4-nitrophenyl)carbodiimide, N,N'-bis(2,4-dinitrophenyl)carbodiimide, N,N'-bis(2,6-dinitrophenyl)carbodiimide, and N,N'-bis(2,4,6-trinitrophenyl)carbodiimide.

Specific examples of the N-alkyl-N'-arylcarbodiimides optionally having a substituent on the aryl group include N-hexyl-N'-phenylcarbodiimide, N-hexyl-N'-(2-nitrophenyl)carbodiimide, N-hexyl-N'-(3-nitrophenyl)carbodiimide, N-methyl-N'-(4-nitrophenyl)carbodiimide, N-ethyl-N'-(4-nitrophenyl)carbodiimide, N-propyl-N'-(4-nitrophenyl)carbodiimide, N-butyl-N'-(4-nitrophenyl)carbodiimide, N-pentyl-N'-(4-nitrophenyl)carbodiimide, N-hexyl-N'-(4-nitrophenyl)carbodiimide, N-hexyl-N'-(2,4-dinitrophenyl)carbodiimide, N-hexyl-N'-(2,6-dinitrophenyl)carbodiimide, N-hexyl-N'-(2,4,6-trinitrophenyl)carbodiimide, N-hexyl-N'-(2-methylphenyl)carbodiimide, N-hexyl-N'-(3-methylphenyl)carbodiimide, N-methyl-N'-(4-methylphenyl)carbodiimide, N-ethyl-N'-(4-methylphenyl)carbodiimide, N-propyl-N'-(4-methylphenyl)carbodiimide, N-butyl-N'-(4-methylphenyl)carbodiimide, N-pentyl-N'-(4-methylphenyl)carbodiimide, N-hexyl-N'-(4-methylphenyl)carbodiimide, N-hexyl-N'-(4-ethylphenyl)carbodiimide, N-hexyl-N'-(4-propylphenyl)carbodiimide, N-hexyl-N'-(4-butylphenyl)carbodiimide, N-hexyl-N'-(4-pentylphenyl)carbodiimide, N-hexyl-N'-(4-hexylphenyl)carbodiimide, N-hexyl-N'-(2,3-dipropylphenyl)carbodiimide, N-hexyl-N'-(2,4-dipropylphenyl)carbodiimide, N-hexyl-N'-(3,4-dipropylphenyl)carbodiimide, N-hexyl-N'-(2,6-dipropylphenyl)carbodiimide, N-hexyl-N'-(2,4,6-tripropylphenyl)carbodiimide, N-hexyl-N'-(4-methoxyphenyl)carbodiimide, N-hexyl-N'-(4-methylthiophenyl)carbodiimide, N-hexyl-N'-{4-(N,N'-dimethylamino)phenyl}carbodiimide, N-hexyl-N'-(4-fluorophenyl)carbodiimide, N-hexyl-N'-(4-chlorophenyl)carbodiimide, N-hexyl-N'-(4-bromophenyl)carbodiimide, N-hexyl-N'-(4-iodophenyl)carbodiimide, and N-cyclohexyl-N'-phenylcarbodiimide. It should be noted that, in the specific examples, each of the alkyl group in the N-alkyl-N'-arylcarbodiimides, and the alkyl group, alkoxy group, alkylthio group, or dialkylamino group as the substituent on the aryl group in the N-alkyl-N'-arylcarbodiimides are not limited to the normal-form, and the branched forms including the sec-form, the tert-form, the iso-form, and the neo-form, or the cyclic forms including the cyclo-form are also included in the specific examples.

Examples of the hydrogen halide represented by the general formula [IX] in the method for producing the biguanidinium salt represented by the general formula [IV] include those exemplified for the hydrogen halide represented by the general formula [IX] in the scheme [S-1].

A commercially available product or a product appropriately synthesized by using a known method can be suitably used for the alkyl halide represented by the general formula [X] in the method for producing the biguanidinium salt represented by the general formula [IV]. Specific examples of the alkyl halide represented by the general formula [X] include methyl chloride, methyl bromide, methyl iodide, ethyl chloride, ethyl bromide, ethyl iodide, propyl chloride, propyl bromide, propyl iodide, butyl chloride, butyl bromide, butyl iodide, pentyl chloride, pentyl bromide, pentyl iodide, hexyl chloride, hexyl bromide, hexyl iodide, heptyl chloride, heptyl bromide, heptyl iodide, octyl chloride, octyl bromide, octyl iodide, nonyl chloride, nonyl bromide, nonyl iodide, decyl chloride, decyl bromide, decyl iodide, undecyl chloride, undecyl bromide, undecyl iodide, dodecyl chloride, dodecyl bromide, dodecyl iodide, norbornyl chloride, norbornyl bromide, norbornyl iodide, bornyl chloride, bornyl bromide, bornyl iodide, menthyl chloride, menthyl bromide, menthyl iodide, adamantyl chloride, adamantyl bromide, adamantyl iodide, decahydronaphthyl chloride, decahydronaphthyl bromide, and decahydronaphthyl iodide. It should be noted that, in the specific examples, the alkyl group in the alkyl halide is not limited to the normal-form, and the branched forms including the sec-form, the tert-form, the iso-form, and the neo-form, or the cyclic forms including the cyclo-form are also included in the specific examples.

A commercially available product or a product appropriately synthesized by using a known method can be suitably used for the compound represented by the general formula [XII] in the method for producing the biguanidinium salt represented by the general formula [IV]. Specific examples of the compound represented by the general formula [XII] include 1-chloro-N,N,N',N'-tetramethylaminoimine chloride, 1-chloro-N,N,N',N'-tetraethylaminoimine chloride, 1-chloro-N,N,N',N'-tetra-n-propylaminoimine chloride, 1-chloro-N,N'-diisopropyl-N,N'-dimethylaminoimine chloride, 1-chloro-N,N'-diethyl-N,N'-diisopropylaminoimine chloride, 1-chloro-N,N,N',N'-tetraisopropylaminoimine chloride, 1-chloro-N,N'-di-tert-butyl-N,N'-dimethylaminoimine chloride, 1-chloro-N,N'-diethyl-N,N'-di-tert-butylaminoimine chloride, 1-chloro-N,N,N',N'-tetra-n-butylaminoimine chloride, 1-chloro-N,N'-dicyclohexyl-N,N'-dimethylaminoimine chloride, 1-chloro-N,N'-diethyl-N,N'-dicyclohexylaminoimine chloride, 2-chloro-1,3-dimethylimidazolinium chloride, 2-chloro-1,3-diethylimidazolinium chloride, 2-chloro-1,3-di-n-propylimidazolinium chloride, 2-chloro-1,3-diisopropylimidazolinium chloride, 2-chloro-1,3-di-n-butylimidazolinium chloride, 2-chloro-1,3-dimethyl-4,5,6-trihydropyrimidinium chloride, and 2-chloro-1,3-dimethyl(1,3-diaza-1-cycloheptene) chloride.

Specific examples of the base to be used in the reaction of the compound represented by the general formula [VIII] and the alkyl halide represented by the general formula [X] to obtain the compound represented by the general formula [XI] include alkali metal hydrides such as sodium hydride and potassium hydride; alkali metal alkoxides such as sodium methoxide, potassium methoxide, sodium ethoxide, potassium ethoxide, lithium-tert-butoxide, sodium-tert-butoxide, and potassium-tert-butoxide; organic lithium compounds such as n-butyllithium, sec-butyllithium, tert-butyllithium, and n-hexyllithium; alkali metal hydroxides such as sodium hydroxide and potassium hydroxide; alkali metal carbonates such as sodium carbonate, potassium carbonate, and cesium carbonate; tertiary amines such as triethylamine, pyridine, 1,5-diazabicyclo[4.3.0]-5-nonene (DBN), and 1,8-diazabicyclo[5.4.0]-7-undecene (DBU); and metal amides such as lithium diisopropylamide (LDA), lithium hexamethyldisilazane (LHMDS), sodium hexamethyldisilazane (NaHMDS), and potassium hexamethyldisilazane (KHMDS). Among them, the alkali metal hydrides such as sodium hydride and potassium hydride are preferred. The bases may be used singly or in combinations of two or more. It should be noted that a commercially available product can be suitably used for the base.

The quantity of the carbodiimide derivative represented by the general formula [VII] to be used in the method for producing the biguanidinium salt represented by the general formula [IV] may be, without any limitation, any quantity typically employed in the field, and, for example, the quantity is typically 0.8 to 10 equivalents, preferably 0.9 to 5 equivalents, and more preferably 1 to 2 equivalents, with respect to the number of moles of the guanidine derivative or imidazolidine derivative represented by the general formula [VI]. If the quantity of the carbodiimide derivative used is extremely small, the yield of the compound represented by the general formula [VIII] may be lower. If the quantity of the carbodiimide derivative used is very large, on the other hand, problems arise, such as the possibility of the occurrence of a side reaction and deterioration of the economic efficiency.

The quantity of the hydrogen halide represented by the general formula [IX] to be used in the method for producing the biguanidinium salt represented by the general formula [IV] may be, without any limitation, any quantity typically employed in the field, and, for example, the quantity is typically 0.8 to 10 equivalents, preferably 0.9 to 5 equivalents, and more preferably 1 to 2 equivalents, with respect to the number of moles of the compound represented by the general formula [VIII] or [XI]. If the quantity of the hydrogen halide used is extremely small, the yield of the compound represented by the general formula $[IV_a]$ or $[IV_b]$ may be lower. If the quantity of the hydrogen halide used is very large, on the other hand, problems arise, such as the possibility of the occurrence of a side reaction and deterioration of the economic efficiency.

The quantity of the alkyl halide represented by the general formula [X] to be used in the method for producing the biguanidinium salt represented by the general formula [IV] may be, without any limitation, any quantity typically employed in the field, and, for example, the quantity is typically 0.8 to 10 equivalents, preferably 0.9 to 5 equivalents, and more preferably 1 to 2 equivalents, with respect to the number of moles of the compound represented by the general formula [VIII]. If the quantity of the alkyl halide used is extremely small, the yield of the compound represented by the general formula [XI] may be lower. If the quantity of the alkyl halide used is very large, on the other hand, problems arise, such as the possibility of the occurrence of a side reaction and deterioration of the economic efficiency.

The quantity of the base to be used in the reaction to obtain the compound represented by the general formula [XI] in the method for producing the biguanidinium salt represented by the general formula [IV] may be, without any limitation, any quantity typically employed in the field, and, for example, the quantity is typically 0.8 to 10 equivalents, preferably 0.9 to 5 equivalents, and more preferably 1 to 2 equivalents, with respect to the number of moles of the compound represented by the general formula [VIII]. If the quantity of the base used is extremely small, the yield of the compound represented by the general formula [XI] may be lower. If the quantity of the base used is very large, on the other hand, problems arise, such as the possibility of the occurrence of a side reaction and deterioration of the economic efficiency.

The quantity of the compound represented by the general formula [XII] to be used in the method for producing the biguanidinium salt represented by the general formula [IV] may be, without any limitation, any quantity typically employed in the field, and, for example, the quantity is typically 0.8 to 10 equivalents, preferably 0.9 to 5 equivalents, and more preferably 1 to 2 equivalents, with respect to the number of moles of the guanidine derivative or imidazolidine derivative represented by the general formula [VI]. If the quantity of the compound represented by the general formula [XII] used is extremely small, the yield of the compound represented by the general formula $[IV_c]$ may be lower. If the quantity of the compound represented by the general formula [XII] used is very large, on the other hand, problems arise, such as the possibility of the occurrence of a side reaction and deterioration of the economic efficiency.

A series of the reactions represented by the scheme [S-2] may be performed without a solvent or in an organic solvent. The organic solvent may be, without any limitation, any organic solvent which does not react with any of the guanidine derivative or imidazolidine derivative represented by the general formula [VI], the carbodiimide derivative represented by the general formula [VII], the hydrogen halide represented by the general formula [IX], the alkyl halide represented by the general formula [X], the compounds represented by the general formulae [VIII], [XI], and [XII], and the base, and specific examples of the organic solvent include aliphatic hydrocarbon solvents such as hexane, heptane, and octane; aromatic hydrocarbon solvents such as benzene, toluene, ethynyltoluene, and xylene; halogen-containing solvents such as dichloromethane, trichloromethane (chloroform), and tetrachloromethane (carbon tetrachloride); ether solvents such as diethyl ether, diisopropyl ether, tert-butyl methyl ether, cyclopentyl methyl ether, tetrahydrofuran, 2-methyltetrahydrofuran, and 1,4-dioxane; glycol ether solvents such as ethylene glycol dimethyl ether, propylene glycol dimethyl ether, ethylene glycol diethyl ether, propylene glycol diethyl ether, diethylene glycol dimethyl ether, dipropylene glycol dimethyl ether, and dipropylene glycol diethyl ether; glycol ether acetate solvents such as ethylene glycol monoethyl ether acetate, diethylene glycol monoethyl ether acetate, diethylene glycol monobutyl ether acetate, propylene glycol monomethyl ether acetate, propylene glycol monoethyl ether acetate, dipropylene glycol monomethyl ether acetate, and dipropylene glycol monoethyl ether acetate; amide solvents such as N,N-dimethylformamide, N,N-dimethylacetamide, 1-methyl-2-pyrrolidinone (N-methylpyrrolidone), and 1,3-dimethyl-2-imidazolidinone (dimethylethyleneurea); sulfoxide solvents such as dimethylsulfoxide and diethylsulfoxide; and nitrile solvents such as acetonitrile. The organic solvents may be used singly or in combinations of two or more. It should be noted that a commercially available product can be suitably used for the organic solvent.

The quantity of the organic solvent to be used may be, without any limitation, any quantity typically employed in the field, and, for example, the quantity is typically 0.01 to 500 L, and preferably 0.1 to 100 L, with respect to 1 mol of the guanidine derivative or imidazolidine derivative represented by the general formula [VI], or 1 mol of the compound represented by the general formula [VIII] or [XI].

It is desirable to perform a series of the reactions represented by the scheme [S-2] under conditions (reaction temperature, pressure, reaction time) as shown below.

It is desirable to set the temperature (reaction temperature) in the reaction of the guanidine derivative or imidazolidine derivative represented by the general formula [VI] and the carbodiimide derivative represented by the general formula [VII] to a temperature such that the guanidine derivative or imidazolidine derivative and the carbodiimide derivative efficiently react together and the compound represented by the general formula [VIII] can be obtained in a favorable yield. Specifically, the temperature is, for example, typically 0 to 200° C., and preferably 20 to 150° C.

It is desirable to set the temperature (reaction temperature) in the reaction of the compound represented by the general formula [VIII] or [XI] and the hydrogen halide represented by the general formula [IX] to a temperature such that the compound represented by the general formula [VIII] or [XI] and the hydrogen halide efficiently react together and the compound represented by the general formula [IV$_a$] or [IV$_b$] can be obtained in a favorable yield. Specifically, the temperature is, for example, typically −20 to 150° C., and preferably 0 to 80° C.

It is desirable to set the temperature (reaction temperature) in the reaction of the compound represented by the general formula [VIII] and the alkyl halide represented by the general formula [X] to a temperature such that the compound represented by the general formula [VIII] and the alkyl halide efficiently react together and the compound represented by the general formula [XI] can be obtained in a favorable yield. Specifically, the temperature is, for example, typically −20 to 150° C., and preferably 0 to 80° C.

It is desirable to set the temperature (reaction temperature) in the reaction of the guanidine derivative or imidazolidine derivative represented by the general formula [VI] and the compound represented by the general formula [XII] to a temperature such that the guanidine derivative or imidazolidine derivative and the compound represented by the general formula [XII] efficiently react together and the compound represented by the general formula [IV$_c$] can be obtained in a favorable yield. Specifically, the temperature is, for example, typically 0 to 200° C., and preferably 20 to 150° C.

The pressure in a series of the reactions represented by the scheme [S-2] may be, without any limitation, any pressure allowing smooth progression of a series of the reactions, and, for example, a series of the reactions can be suitably performed under normal pressure.

The reaction time in a series of the reactions represented by the scheme [S-2] may be affected by the kinds of the guanidine derivative or imidazolidine derivative represented by the general formula [VI], the carbodiimide derivative represented by the general formula [VII], the hydrogen halide represented by the general formula [IX], the alkyl halide represented by the general formula [X], the compounds represented by the general formulae [VIII], [XI], and [XII], and the base, the quantities of these compounds and the base or the like to be used, the presence or absence of the organic solvent and the kind thereof, the reaction temperature, the pressure in reaction, and so on. Although desirable reaction time thus depends on the situation, the reaction time is, for example, typically 1 minute to 72 hours, and preferably 3 minutes to 48 hours.

The product in a series of the reactions represented by the scheme [S-2] can be isolated by using a post-treatment operation and purification operation typically performed in the field. Specific examples of the method for isolating each of the compounds represented by the general formulae [VIII] and [XI] include a method in which a non-polar solvent such as hexane is added to the reaction solution after the completion of the reactions, the reaction solution is cooled, and a solid (crystal) resulting from the cooling is collected by filtration. In addition, specific examples of the method for isolating each of the compounds represented by the general formulae [IV$_a$], [IV$_b$], and [IV$_c$] include a method in which a polar solvent such as acetone is added to the reaction solution after the completion of the reactions, a solid precipitated is removed by filtration or the like, and the filtrate is concentrated. It should be noted that, as necessary, the reaction solution after the completion of the reactions may be filtered or washed with water or the like, or the residue obtained by the concentration of the reaction solution may be subjected to recrystallization, distillation, column chromatography, etc., to isolate the product.

The biguanidinium salt represented by the general formula [V] corresponding to the biguanidinium salt represented by any of the general formulae [IV$_a$] and [IV$_b$] (carbonate: the compound represented by the general formula [V]) can be produced by using carbon dioxide such as dry ice in place of the hydrogen halide represented by the general formula [IX] in the reactions represented by the scheme [S-2].

—Base-Generating Agent of the Present Invention—

The base-generating agent of the present invention comprises the compound of the present invention (the compound represented by the general formula (A)), and generates a base through irradiation with light (an active energy ray) such as ultraviolet rays, visible rays, infrared rays, and X-rays, or heating.

For allowing the base-generating agent of the present invention to generate a base therefrom through irradiation with light (an active energy ray), irradiation with light (an active energy ray), typically at wavelengths of 100 to 780 nm, preferably at wavelengths of 200 to 450 nm, can be suitably performed. The base-generating agent of the present invention has a high molar absorption coefficient in an absorption wavelength region of 200 to 450 nm, and hence can efficiently generate a base. In addition, it is preferred for the base-generating agent of the present invention to exhibit absorption to at least one or more lights (active energy rays) of the i-ray, the h-ray, and the g-ray, within the wavelength region, from the viewpoint of versatility.

For allowing the base-generating agent of the present invention to generate a base therefrom through heating, the base-generating agent of the present invention can generate a base through thermal energy in heating typically at 150 to 400° C., preferably at 250 to 350° C.

The temperature of the base-generating agent of the present invention when the weight after heating decreases by 5% by weight from the initial weight (hereinafter, occasionally abbreviated as "5% weight loss temperature") is preferably 1500° C. or higher. In production of a cured film by using the base-generating agent of the present invention, baking or the like is performed in some cases to cure a coating film. In a case where the 5% weight loss temperature of the base-generating agent is high, the baking temperature can be set high, and hence, for example, the amount of residues of an organic solvent contained in the base-curable resin composition of the present invention, which will be described later, can be as small as possible after baking. Thereby, deterioration of the contrast ratio between an exposed portion (a portion irradiated with light) and an unexposed portion (a portion not irradiated with light) by such a residual organic solvent can be reduced.

The base-generating agent of the present invention may comprise an additive such as a sensitizer and an organic solvent in addition to the compound of the present invention (the compound represented by the general formula (A)), in a range that does not interfere the purpose and advantageous effects of the present invention. The additives may be used singly or in combinations of two or more. It should be noted that a commercially available product or a product appropriately synthesized by using a known method can be suitably used for the additive.

—Base-Curable Resin Composition of the Present Invention—

The base-curable resin composition of the present invention comprises the compound of the present invention (the compound represented by the general formula (A)) and a base-curable resin raw material, and has a property to cure through polymerization reaction, crosslinking reaction, or the like caused by the action of a base generated from the compound of the present invention (the base-generating agent).

"Base-curable resin raw material" comprised in the base-curable resin composition of the present invention is a collective term for compounds which react by the action of a strong base (biguanide) generated from the compound of the present invention (the base-generating agent) and cause polymerization reaction, crosslinking reaction, or the like. That is, the base-curable resin raw material serves as a resin raw material having a property to cure by the action of a base, and can include various raw materials including those capable of becoming a polymer through polymerization of only one resin raw material (monomer, oligomer, or polymer), for example, by the action of a base, and those capable of becoming a polymer through polymerization or crosslinking of a plurality of resin raw materials (monomer, oligomer, or polymer), for example, by the action of a base. Specific examples of such base-curable resin raw materials include epoxy compounds (epoxy resins) having at least one epoxy group, silicone compounds (silicone resins) having at least one alkoxysilyl group or silanol group, isocyanate compounds (isocyanate resins) having at least one isocyanate group, and polyamic acid compounds (polyamic acid resins) having at least one amide bond. The base-curable resin raw materials may be used singly or in combinations of two or more, as long as they can be polymerized by the action of a base.

The epoxy compounds (the epoxy resins) may be any of a monomer, an oligomer, or a polymer, and specific examples thereof include diglycidyl ether, spiroglycol diglycidyl ether, ethylene glycol diglycidyl ether, diethylene glycol diglycidyl ether, propylene glycol diglycidyl ether, tripropylene glycol diglycidyl ether, butanediol diglycidyl ether, glycerin diglycidyl ether, glycidylpropoxytrimethoxysilane, allyl glycidyl ether, butyl glycidyl ether, neopentyl glycol diglycidyl ether, 1,6-hexanediol diglycidyl ether, phenyl glycidyl ether, cresyl glycidyl ether, alkylphenol glycidyl ether, bisphenol A-type diglycidyl ether, bisphenol F-type diglycidyl ether, bisphenol AD-type diglycidyl ether, biphenyl-type diglycidyl ether, 3,4-epoxycyclohexylmethyl-3',4'-epoxycyclohexane carboxylate, tertiary fatty acid monoglycidyl ether, polyfunctional glycidyl ether, polyethylene glycol diglycidyl ether, polypropylene glycol diglycidyl ether, polyglycidyl methacrylate, glycerin polyglycidyl ether, diglycerin polyglycidyl ether, trimethylolpropane polyglycidyl ether, and sorbitol polyglycidyl ether. The epoxy compounds (the epoxy resins) may have been halogenated or hydrogenated. In addition, derivatives of the specific examples are also included in examples of the epoxy compounds (the epoxy resins). The epoxy compounds (the epoxy resins) may be used singly or in combinations of two or more. It should be noted that a commercially available product or a product appropriately synthesized by using a known method can be suitably used for the epoxy compounds (the epoxy resins).

The weight-average molecular weight of the epoxy compounds (the epoxy resins) in a case where it is an oligomer or a polymer is preferably 100 to 30,000, and more preferably 200 to 20,000, from the viewpoint of the thermal resistance, coating property, solubility in organic solvents, solubility in developing solutions, and so on, of the base-curable resin composition of the present invention. If the weight-average molecular weight is lower than 100, then the strength of a cured film or a shaped product obtained from the base-curable resin composition of the present invention may be insufficient. If the weight-average molecular weight is higher than 30,000, on the other hand, not only the viscosity of the epoxy compounds (the epoxy resins) itself may increase to degrade the solubility, but also it may be difficult to obtain a cured film with a homogeneous surface and constant thickness. It should be noted that the weight-average molecular weight is a value obtained through measurement with gel permeation chromatography followed by conversion of the measurement in terms of standard polystyrene.

The silicone compounds (the silicone resins) may be any of a monomer, an oligomer, or a polymer, and specific examples thereof include alkoxysilane compounds and silane coupling agents. Specific examples of the alkoxysilane compounds include trimethylmethoxysilane, dimethyldimethoxysilane, methyltrimethoxysilane, tetramethoxysilane, trimethylethoxysilane, dimethyldiethoxysilane, methyltriethoxysilane, tetraethoxysilane, diphenyldimethoxysilane, phenyltrimethoxysilane, diphenyldiethoxysilane, phenyltriethoxysilane, hexyltrimethoxysilane, tetrapropoxysilane, tetrabutoxysilane, poly-3-(methyldimethoxysilyl)propyl methacrylate, poly-3-(methyldiethoxysilyl)propyl methacrylate, poly-3-(trimethoxysilyl)propyl methacrylate, and poly-3-(triethoxysilyl)propyl methacrylate. The alkoxysilane compounds may be used singly or in combinations of two or more. It should be noted that a commercially available product or a product appropriately synthesized by using a known method can be suitably used for the alkoxysilane compounds.

Specific examples of the silane coupling agents include vinylsilane, acrylsilane, epoxysilane, and aminosilane. Specific examples of the vinylsilane include vinyltrichlorosilane, vinyltrimethoxysilane, vinyltriethoxysilane, and vinyltris(β-methoxyethoxy)silane. Specific examples of the acrylsilane include γ-methacryloxypropyltrimethoxysilane and γ-methacryloxypropylmethyldimethoxysilane. Specific examples of the epoxysilane include β-(3,4-epoxycyclohexyl)ethyltrimethoxysilane, γ-glycidoxypropyltrimethoxysilane, and γ-glycidoxypropylmethyldiethoxysilane. Specific examples of the aminosilane include γ-aminopropyltrimethoxysilane, N-β-(aminoethyl)-γ-aminopropyltrimethoxysilane, N-β-(aminoethyl)-γ-aminopropylmethyldimethoxysilane, and N-phenyl-γ-aminopropyltrimethoxysilane. Specific examples of the silane coupling agents other than the above include γ-mercaptopropyltrimethoxysilane, γ-chloropropylmethyldimethoxysilane, and γ-chloropropylmethyldiethoxysilane. The silane coupling agents may be used singly or in combinations of two or more. It should be noted that a commercially available product or a product appropriately synthesized by using a known method can be suitably used for the silane coupling agents.

The weight-average molecular weight of the silicone compounds (the silicone resins) in a case where it is an oligomer or a polymer is preferably 100 to 30,000, and more preferably 200 to 20,000, from the viewpoint of the thermal resistance, coating property, solubility in organic solvents, solubility in developing solutions, and so on, of the base-curable resin composition of the present invention. If the weight-average molecular weight is lower than 100, then the strength of a cured film or a shaped product obtained from the base-curable resin composition of the present invention may be insufficient. If the weight-average molecular weight is higher than 30,000, on the other hand, not only the viscosity of the silicone compounds (the silicone resins) itself may increase to degrade the solubility, but also it may be difficult to obtain a cured film with a homogeneous surface and constant thickness. It should be noted that the weight-average molecular weight is a value obtained through measurement with gel permeation chromatography followed by conversion of the measurement in terms of standard polystyrene.

The isocyanate compounds (the isocyanate resins) may be any of a monomer, an oligomer, or a polymer, and specific examples thereof include monomeric isocyanate compounds and dimeric isocyanate compounds. Preferred specific examples of the isocyanate compounds include toluene-2,4-diisocyanate, toluene-2,6-diisocyanate, m-xylylene diisocyanate, hexahydro-m-xylylene diisocyanate, hexamethylene diisocyanate, isophorone diisocyanate, methylenediphenyl-4,4'-diisocyanate, and polymethylene polyphenyl polyisocyanate. The isocyanate compounds (the isocyanate resins) may be used singly or in combinations of two or more. It should be noted that a commercially available product or a product appropriately synthesized by using a known method can be suitably used for the isocyanate compounds (the isocyanate resins).

The weight-average molecular weight of the isocyanate compounds (the isocyanate resins) in a case where it is an oligomer or a polymer is preferably 100 to 30,000, and more preferably 200 to 20,000, from the viewpoint of the thermal resistance, coating property, solubility in organic solvents, solubility in developing solutions, and so on, of the base-curable resin composition of the present invention. If the weight-average molecular weight is lower than 100, then the strength of a cured film or a shaped product obtained from the base-curable resin composition of the present invention may be insufficient. If the weight-average molecular weight is higher than 30,000, on the other hand, not only the viscosity of the isocyanate compounds (the isocyanate resins) itself may increase to degrade the solubility, but also it may be difficult to obtain a cured film with a homogeneous surface and constant thickness. It should be noted that the weight-average molecular weight is a value obtained through measurement with gel permeation chromatography followed by conversion of the measurement in terms of standard polystyrene.

The polyamic acid compounds (the polyamic acid resins) may be any of known polyamic acid compounds (polyamic acid resins) obtained by reaction of an acid anhydride and a diamine, and specific examples thereof include polyamic acid compounds (polyamic acid resins) obtained by reaction of a tetracarboxylic dianhydride such as pyromellitic dianhydride, naphthalenetetracarboxylic dianhydride, biphenyl ether tetracarboxylic dianhydride, benzophenone tetracarboxylic dianhydride, cyclopentane tetracarboxylic dianhydride, cyclohexane tetracarboxylic dianhydride, 4-(1,2-dicarboxyethyl)-1,2,3,4-tetrahydronaphthalene-1,2-dicarboxylic dianhydride, and 5-(1,2-dicarboxyethyl)-3-methylcyclohexane-1,2-dicarboxylic dianhydride, and a diamine such as phenylenediamine, diaminobiphenyl ether, and diaminobenzophenone. The polyamic acid compounds (the polyamic acid resins) may have been halogenated or hydrogenated. In addition, derivatives of the specific examples are also included in examples of the polyamic acid compounds (the polyamic acid resins). The polyamic acid compounds (the polyamic acid resins) may be used singly or in combinations of two or more. It should be noted that a commercially available product or a product appropriately synthesized by using a known method can be suitably used for the polyamic acid compounds (the polyamic acid resins).

The weight-average molecular weight of the polyamic acid compounds (the polyamic acid resins) is preferably 100 to 30,000, and more preferably 200 to 20,000, from the viewpoint of the thermal resistance, coating property, solubility in organic solvents, solubility in developing solutions, and so on, of the base-curable resin composition of the present invention. If the weight-average molecular weight is lower than 100, then the strength of a cured film or a shaped product obtained from the base-curable resin composition of the present invention may be insufficient. If the weight-average molecular weight is higher than 30,000, on the other hand, not only the viscosity of the polyamic acid compounds (the polyamic acid resins) itself may increase to degrade the solubility, but also it may be difficult to obtain a cured film with a homogeneous surface and constant thickness. It should be noted that the weight-average molecular weight is a value obtained through measurement with gel permeation chromatography followed by conversion of the measurement in terms of standard polystyrene.

The content of the compound of the present invention (the base-generating agent) comprised in the base-curable resin composition of the present invention may be, without any limitation, any content typically employed in the field, and, for example, the content is typically 0.1 to 100% by weight, preferably 1 to 50% by weight, and more preferably 5 to 30% by weight, with respect to the weight of the base-curable resin raw material. If the content of the compound of the present invention (the base-generating agent) is extremely low, the base-curable resin composition of the present invention may be insufficiently cured. If the content of the compound of the present invention (the base-generating agent) is very high, on the other hand, problems arise, such as deterioration of the economic efficiency.

In a case where the base-curable resin composition of the present invention is used as a photosensitive resin composition, a sensitizer may be added to the composition to widen the photosensitive wavelength region for enhancement of the sensitivity. The sensitizer may be, without any limitation, any sensitizer typically used in the field, and preferred specific examples of the sensitizer include benzophenone, 4,4'-bis(dimethylamino)benzophenone, 4,4'-bis(diethylamino)benzophenone, ketoprofen, 2-(9-oxoxanthen-2-yl) propionic acid, 2-chlorothioxanthone, 2-isopropylthioxanthone, 2,4-diethylthioxanthone, anthrone, benzanthrone, 3-methyl-1,3-diaza-1,9-benzanthrone, anthracene, 9-ethoxyanthracene, 9,10-diphenylanthracene, 1,2-benzanthracene, pyrene, perylene, phenothiazine, benzophenoxazine, benzil, acridine, acridine orange, acridine yellow, acridone, oxazine, benzoflavin, riboflavin, setoflavin-T, 9-fluorenone, 2-nitrofluorene, 2,3-benzofluorene, acenaphthene, 5-nitroacenaphthene, acetophenone, phenanthrene, 3,4,5,6-dibenzophenanthrene, 1,2-naphthoquinone, phylloquinone, anthraquinone, 2-ethylanthraquinone, 2-tert-butylanthraquinone, 1,2-benzanthraquinone, benzoquinone, methylbenzoquinone, 4-nitroaniline, 2-chloro-4-nitroaniline, 2,6-dichloro-4-nitroaniline, N-acetyl-4-nitroaniline, N-acetyl-4-nitro-1-naphthylamine, picramide, dibenzalacetone, coumarin, 3,3'-carbonyl-bis(5,7-dimethoxycarbonyl-coumarin), N-methylnifedipine, fluorescein, rhodamine, eosin, erythrosine, coronene, rose bengal, malachite green, basic blue 7, toluidine blue (basic blue 17), indigo, chlorophyll, tetraphenylporphyrin, phthalocyanine, tris(4-dimethylaminophenyl)isopropenyl, 2,4,6-triarylpyrylium, sodium 4-(1-naphthylazo)benzenesulfonate, phenylbis(2,4,6-trimethylbenzoyl)phosphine oxide, 1-[(4-phenylthio)phenyl]octan-1,2-dione 2-(O-benzyloxime), 1-[9-ethyl-6-(2-m ethylbenzoyl)-9H-carbazol-3-yl]ethanone O-acetyloxime, 9-anthrylmethyl N,N-diethylcarbamate, 1-(9,10-dibutoxyanthracen-2-yl)ethyl piperidine-1-carboxylate, 1-(anthraquinon-2-yl)ethyl N,N-diethyl-1-carbamate, and 1,2-diisopropyl-4,4,5,5-tetramethylbiguanidium 2-(3-benzoylphenyl) propionate. Among these preferred sensitizers, the 2-isopropylthioxanthone and 2,4-diethylthioxanthone, which are stable in resins, are more preferred. The sensitizers may be used singly or in combinations of two or more. It should be noted that a commercially available product or a product appropriately synthesized by using a known method can be suitably used for the sensitizer.

The content of the sensitizer contained in the base-curable resin composition of the present invention, as necessary, may be, without any limitation, any content typically employed in the field, and, for example, the content can be appropriately determined in consideration of the kinds and quantities of the compound of the present invention (the base-generating agent) and the base-curable resin raw material to be used, required sensitivity and the like. More specifically, in a case where the sensitizer is contained, the content of the sensitizer is preferably 1 to 30% by weight, and more preferably 1 to 20% by weight, with respect to the total weight of the base-curable resin composition of the present invention. If the content of the sensitizer is less than 1% by weight, enhancement of the sensitivity may be insufficient. If the content of the sensitizer is more than 30% by weight, on the other hand, enhancement of the sensitivity may be excessive.

The base-curable resin composition of the present invention preferably contains a crosslinking agent such as thiol compounds, multivalent carboxylic acids, multivalent carboxylic anhydrides, and polyhydric phenols, as a base-curable resin raw material, in addition to the epoxy compounds (the epoxy resins), the silicone compounds (the silicone resins), the isocyanate compounds (the isocyanate resins), and the polyamic acid compounds (the polyamic acid resins).

The thiol compounds acts as a crosslinking agent to cure the epoxy compounds (the epoxy resins) through reaction with the epoxy group of the epoxy compounds (the epoxy resins) when being used with the epoxy compounds (the epoxy resins). Although such thiol compounds may be any of a monomer, an oligomer, or a polymer, thiol compounds having two or more thiol groups are preferred. Specific examples of the thiol compounds include thiol compounds having two to five thiol groups such as ethylene glycol bis(3-mercaptobutyrate), ethylene glycol bis(3-mercaptoisobutyrate), diethylene glycol bis(3-mercaptopropionate), butanediol bis(3-mercaptobutyrate), butanediol bis(3-mercaptoisobutyrate), pentaerythritol tetrakis(3-mercaptopropionate), pentaerythritol tetrakis(3-mercaptobutyrate), pentaerythritol tetrakis(3-mercaptoisobutyrate), dipentaerythritol hexakis(3-mercaptopropionate), dipentaerythritol hexakis(3-mercaptobutyrate), dipentaerythritol hexakis(3-mercaptoisobutyrate), trimethylolpropane tris(3-mercaptopropionate), trimethylolpropane tris(3-mercaptoisobutyrate), tris[(3-mercaptopropionyloxy)ethyl]isocyanurate, 1,4-bis(3-mercaptobutyryloxy)butane, and 1,3,5-tris (3-mercaptobutyloxyethyl)-1,3,5-triazine-2,4,6-(1H,3H, 5H)-trione; liquid polymercaptan, and polysulfide. Among these thiol compounds, the pentaerythritol tetrakis(3-mercaptopropionate), pentaerythritol tetrakis(3-mercaptobutyrate), tris[(3-mercaptopropionyloxy)ethyl]isocyanurate, and 1,3,5-tris(3-mercaptobutyloxyethyl)-1,3,5-triazine-2,4, 6-(1H,3H,5H)-trione are preferred, from the viewpoint of curing performance, handiness, and so on. The thiol compounds may be used singly or in combinations of two or more. It should be noted that a commercially available product or a product appropriately synthesized by using a known method can be suitably used for the thiol compounds.

The weight-average molecular weight of the thiol compounds in a case where it is an oligomer or a polymer is preferably 100 to 10,000, and more preferably 200 to 5,000, from the viewpoint of the thermal resistance, coating property, solubility in organic solvents, solubility in developing solutions, and so on, of the base-curable resin composition of the present invention. If the weight-average molecular weight is lower than 100, then the strength of a cured film or a shaped product obtained from the base-curable resin composition of the present invention may be insufficient. If the weight-average molecular weight is higher than 10,000, on the other hand, not only the viscosity of the thiol compounds itself may increase to degrade the solubility, but also it may be difficult to obtain a cured film with a homogeneous surface and constant thickness. It should be noted that the weight-average molecular weight is a value obtained through measurement with gel permeation chromatography followed by conversion of the measurement in terms of standard polystyrene.

The content of the thiol compounds is preferably a content such that, with respect to the epoxy compounds (the epoxy resins) in the base-curable resin raw material, the ratio of "equivalent of thiol group (equivalent of SH group)/equivalent of epoxy group" is, for example, 0.3/1.7 to 1.7/0.3, and more preferably a content such that the ratio is 0.8/1.2 to 1.2/0.8.

The multivalent carboxylic acids and multivalent carboxylic anhydrides act as a crosslinking agent to cure the epoxy compounds through reaction with the epoxy group of the epoxy compounds (the epoxy resins) when being used with the epoxy compounds (the epoxy resins). The multivalent carboxylic acids and multivalent carboxylic anhydrides may be any of a monomer, an oligomer, or a polymer. Specific examples of the multivalent carboxylic acids include divalent carboxylic acids such as phthalic acid, tetrahydrophthalic acid, hexahydrophthalic acid, methyltetrahydrophthalic acid, methylhexahydrophthalic acid, methylnadic acid, dodecylsuccinic acid, azelaic acid, and chlorendic acid; trivalent carboxylic acids such as trimellitic acid; tetravalent carboxylic acids such as pyromellitic acid, benzophenone tetracarboxylic acid, and methylcyclohexene tetracarboxylic acid; and multivalent carboxylic acids such as polyazelaic acid, (meth)acrylic acid polymer, and (meth) acrylic acid/(meth)acrylate polymer. Specific examples of the multivalent carboxylic anhydrides include divalent carboxylic anhydrides such as phthalic anhydride, tetrahydrophthalic anhydride, hexahydrophthalic anhydride, methyltetrahydrophthalic anhydride, methylhexahydrophthalic anhydride, methylnadic anhydride, dodecylsuccinic anhydride, azelaic anhydride, and chlorendic anhydride; trivalent carboxylic anhydrides containing a free acid such as trimellitic anhydride; tetravalent carboxylic anhydrides such as pyromellitic anhydride, benzophenone tetracarboxylic anhydride, ethylene glycol bis(anhydrotrimellitate), and methylcyclohexene tetracarboxylic anhydride; and multivalent carboxylic anhydrides such as polyazelaic anhydride. The multivalent carboxylic acids or multivalent carboxylic anhydrides may be used singly or in combinations of two or more. It should be noted that a commercially available product or a product appropriately synthesized by using a known method can be suitably used for the multivalent carboxylic acids and multivalent carboxylic anhydrides.

The weight-average molecular weight of the multivalent carboxylic acids or multivalent carboxylic anhydrides in a case where it is an oligomer or a polymer is preferably 100 to 10,000, and more preferably 200 to 5,000, from the viewpoint of the thermal resistance, coating property, solubility in organic solvents, solubility in developing solutions, and so on, of the base-curable resin composition of the present invention. If the weight-average molecular weight is lower than 100, then the strength of a cured film or a shaped product obtained from the base-curable resin composition of the present invention may be insufficient. If the weight-average molecular weight is higher than 10,000, on the other hand, not only the viscosity of the multivalent carboxylic acids or multivalent carboxylic anhydrides itself may increase to degrade the solubility, but also it may be difficult to obtain a cured film with a homogeneous surface and constant thickness. It should be noted that the weight-average molecular weight is a value obtained through measurement with gel permeation chromatography followed by conversion of the measurement in terms of standard polystyrene.

The content of the multivalent carboxylic acids and multivalent carboxylic anhydrides is preferably a content such that, with respect to the epoxy compounds (the epoxy resins) in the base-curable resin raw material, the ratio of "equivalent of carboxy group (equivalent of —C(=O)O— group)/equivalent of epoxy group" is, for example, 0.5/2.5 to 2.5/0.5, and more preferably a content such that the ratio is 1.0/2.0 to 2.0/1.0.

The polyhydric phenols acts as a crosslinking agent to cure the epoxy compounds through reaction with the epoxy group of the epoxy compounds (the epoxy resins) when being used with the epoxy compounds (the epoxy resins). The polyhydric phenols may be any of a monomer, an oligomer, or a polymer. Specific examples of the polyhydric phenols include compounds (resins) having a phenolic hydroxyl group such as phenol novolac resin, alkylphenol novolac resin, bisphenol A-type novolac resin, dicyclopentadiene-type phenolic resin, Xylok-type phenolic resin, terpene-modified phenolic resin, polyvinylphenolic resin, bisphenol F-type phenolic resin, bisphenol S-type phenolic resin, poly-4-hydroxystyrene, condensates of naphthol and aldehydes, and condensates of dihydroxynaphthalene and aldehydes. The polyhydric phenols may be used singly or in combinations of two or more. It should be noted that a commercially available product or a product appropriately synthesized by using a known method can be suitably used for the polyhydric phenols.

The weight-average molecular weight of the polyhydric phenols in a case where it is an oligomer or a polymer is preferably 100 to 10,000, and more preferably 200 to 5,000, from the viewpoint of the thermal resistance, coating property, solubility in organic solvents, solubility in developing solutions, and so on, of the base-curable resin composition of the present invention. If the weight-average molecular weight is lower than 100, then the strength of a cured film or a shaped product obtained from the base-curable resin composition of the present invention may be insufficient. If the weight-average molecular weight is higher than 10,000, on the other hand, not only the viscosity of the polyhydric phenols itself may increase to degrade the solubility, but also it may be difficult to obtain a cured film with a homogeneous surface and constant thickness. It should be noted that the weight-average molecular weight is a value obtained through measurement with gel permeation chromatography followed by conversion of the measurement in terms of standard polystyrene.

The content of the polyhydric phenols is preferably a content such that, with respect to the epoxy compounds (the epoxy resins) in the base-curable resin raw material, the ratio of "equivalent of phenolic hydroxyl group (equivalent of —OH group)/equivalent of epoxy group" is, for example, 0.5/2.5 to 2.5/0.5, and more preferably a content such that the ratio is 1.0/2.0 to 2.0/1.0.

The crosslinking agent such as the thiol compounds, the multivalent carboxylic acids or multivalent carboxylic anhydrides, and the polyhydric phenols contained in the base-curable resin composition of the present invention reduces the shrinkage of a cured film in curing to enhance the dimensional stability of the cured film, in comparison with the case of a base-curable resin composition not containing these crosslinking agents, and, in addition, can enhance the flexibility, water resistance, chemical resistance, adhesion between the resin and a substrate, resistance to curing inhibition by oxygen, and so on, of the resin obtained from the base-curable resin composition of the present invention.

Especially, combinational use of the epoxy compounds and the thiol compounds or the multivalent carboxylic acids or multivalent carboxylic anhydrides, as a base-curable resin raw material for the base-curable resin composition of the present invention, not only accelerates the progression of crosslinking reaction of the epoxy compounds and the thiol compounds or the multivalent carboxylic acids or multivalent carboxylic anhydrides to allow early initiation of curing, but also can increases the curing rate of the epoxy compounds (the epoxy resins), and thus the combinational use is effective for a curing system for an epoxy compounds (an epoxy resins).

The acid value of the carboxy group-containing resin obtained through reaction of the multivalent carboxylic acids or multivalent carboxylic anhydrides is preferably 40 to 200 mg KOH/g, and more preferably 45 to 120 mg KOH/g. Development with an alkali is properly achieved with the carboxy group-containing resin having an acid value of 40 mg KOH/g or higher, and dissolution of an exposed portion (a portion irradiated with light) caused by a developing solution can be avoided with the carboxy group-containing resin having an acid value of 200 mg KOH/g or lower. Accordingly, a higher contrast ratio between an exposed portion (a portion irradiated with light) and an unexposed portion (a portion not irradiated with light) can be provided without excessive break of lines, and thus normal drawing of a resist pattern can be achieved.

When the base-curable resin composition of the present invention is applied onto a given substrate, for example, it is desirable for the composition to contain an organic solvent in some cases. The organic solvent contained in the base-curable resin composition of the present invention can enhance the coating property, and provides favorable workability. The organic solvent may be, without any limitation, any organic solvent typically used in the field. Specific examples of the organic solvent include saturated or unsaturated aliphatic hydrocarbon solvents such as pentane, hexane, heptane, octane, nonane, decane, tetrahydronaphthalene, menthane, and squalane; aromatic hydrocarbon solvents such as benzene, toluene, ethynyltoluene, ethylbenzene, diethylbenzene, trimethylbenzene, styrene, and xylene; halogen-containing solvents such as dichloromethane, trichloromethane (chloroform), and tetrachloromethane (carbon tetrachloride); ether solvents such as diethyl ether, di-n-propyl ether, diisopropyl ether, tert-butyl methyl ether, di-n-butyl ether, di-tert-butyl ether, cyclopentyl methyl ether, tetrahydrofuran, 2-methyltetrahydrofuran, and 1,4-dioxane; alcohol solvents such as methanol, ethanol, n-propanol, isopropanol, n-butanol, isobutanol, sec-butanol, tert-butanol, and 2-methoxyethanol; glycol ether solvents such as ethylene glycol monomethyl ether, propylene glycol monomethyl ether (PGME), propylene glycol monoethyl ether, diethylene glycol monomethyl ether, dipropylene glycol monomethyl ether, dipropylene glycol monoethyl ether, ethylene glycol dimethyl ether, propylene glycol dimethyl ether, ethylene glycol diethyl ether, propylene glycol diethyl ether, diethylene glycol dimethyl ether, diethylene glycol diethyl ether, dipropylene glycol dimethyl ether, and dipropylene glycol diethyl ether; glycol ether acetate solvents such as ethylene glycol monoethyl ether acetate, diethylene glycol monoethyl ether acetate, diethylene glycol monobutyl ether acetate, propylene glycol monomethyl ether acetate (PGMEA), propylene glycol monoethyl ether acetate, dipropylene glycol monomethyl ether acetate, and dipropylene glycol monoethyl ether acetate; ketone solvents such as 2-propanone (acetone), 2-butanone (ethyl methyl ketone), diethyl ketone, 4-methyl-2-pentanone (methyl isobutyl ketone), cyclopentanone, cyclohexanone, and cycloheptanone; ester solvents such as methyl acetate, ethyl acetate, n-propyl acetate, isopropyl acetate, isobutyl acetate, sec-butyl acetate, tert-butyl acetate, ethyl butyrate, isoamyl butyrate, ethyl lactate (EL), n-propyl lactate, isopropyl lactate, isobutyl lactate, sec-butyl lactate, tert-butyl lactate, isoamyl lactate, γ-butyrolactone, and butyl stearate; amide solvents such as N,N-dimethylformamide, N,N-dimethylacetamide, 1-methyl-2-pyrrolidinone (N-methylpyrrolidone), and 1,3-dimethyl-2-imidazolidinone (dimethylethyleneurea); and nitrile solvents such as acetonitrile. The organic solvents may be used singly or in combinations of two or more. It should be noted that a commercially available product can be suitably used for the organic solvent.

The content of the organic solvent contained in the base-curable resin composition of the present invention, as necessary, may be, without any limitation, any content typically employed in the field, and, for example, the content can be appropriately selected so that homogenous application can be achieved when the base-curable resin composition of the present invention is applied onto a given substrate to form a layer of the base-curable resin composition of the present invention. The content of the organic solvent contained in the base-curable resin composition of the present invention, as necessary, is, for example, typically 0.01 to 50 mL, preferably 0.05 to 30 mL, and more preferably 0.1 to 10 mL, with respect to 1 g of the base-curable resin raw material.

The base-curable resin composition of the present invention may contain an additive in addition to the base-curable resin raw material, in a range that does not interfere the purpose and advantageous effects of the present invention, and examples of the additive include fillers, pigments, dyes, leveling agents, defoamers, antistatic agents, pH adjusters, dispersants, dispersing aids, surface modifiers, plasticizers, plasticizing accelerators, anti-sagging agents, and curing accelerators. The additives may be used singly or in combinations of two or more. It should be noted that a commercially available product or a product appropriately synthesized by using a known method can be suitably used for the additive.

Patterning can be performed by using the base-curable resin composition of the present invention, for example as follows: a coating solution is prepared with the base-curable resin composition of the present invention; the coating solution prepared is applied onto an appropriate solid surface of a substrate or the like, and dried to form a coating film; patterning exposure is then performed for the coating film formed to allow the compound of the present invention (the base-generating agent) to generate a base therefrom; and thereafter heating is performed under given conditions to promote polymerization reaction, crosslinking reaction, or the like of the base-curable resin raw material contained in the base-curable resin composition.

Since the base-curable resin composition of the present invention comprises the compound of the present invention (the base-generating agent), polymerization reaction proceeds through irradiation with light (an active energy ray) even at room temperature. However, it is preferred to perform baking (heating) treatment for efficient progression of polymerization reaction, crosslinking reaction, or the like. Conditions for baking (heating) treatment can be appropriately determined in consideration of the energy of irradiation with (exposure to) light (an active energy ray), the kinds of a strong base (biguanide) generated from the compound of the present invention (the base-generating agent) to be used, the kinds of the base-curable resin raw material, and so on. The baking (heating) temperature is preferably in the range of 50° C. to 250° C., and more preferably in the range of 60° C. to 180° C. In addition, the baking (heating) time is preferably 10 seconds to 60 minutes, and more preferably 60 seconds to 40 minutes. A substrate on which a coating film has been formed through irradiation with light (an active energy ray) followed by heating, as necessary, is soaked for development in a solvent (developing solution) in which an exposed portion (a portion irradiated with light) and an unexposed portion (a portion not irradiated with light) are different in solubility, and thus a pattern can be obtained.

Known methods can be appropriately employed as a method for applying the base-curable resin composition of the present invention onto a substrate, a method for baking, a method for irradiating with light (an active energy ray), a method for developing, and so on, each to be performed in the patterning.

The base-curable resin composition of the present invention comprises the compound of the present invention (the base-generating agent) and the base-curable resin raw material, and thereby polymerization reaction, crosslinking reaction, or the like of the base-curable resin raw material takes place by the action of a strong base (biguanide) as an initiator generated from the compound of the present invention (the base-generating agent) through an operation of, for example, irradiation with light (an active energy ray) or heating, and thus curing (polymerization) of the base-curable resin raw material can effectively proceed. The base-curable resin composition of the present invention, which has such an advantageous effect, can be suitably used for curable materials, resist materials (patterning materials), and so on.

In a case where the base-curable resin composition of the present invention is used for a curable material, a shaped product formed therefrom after curing reaction can be used for members in fields for which properties including thermal resistance, dimensional stability, and insulation properties are deemed effective, such as coating materials, printing inks, color filters, films for flexible displays, semiconductor devices, electronic parts, interlayer dielectrics, wiring-covering films, optical circuits, parts for optical circuits, antireflection films, and holograms. In addition, in a case where the base-curable resin composition of the present invention is used for a resist material (patterning material), a cured film (pattern) or the like formed therefrom after patterning reaction has thermal resistance and insulating properties, and can be effectively used for, for example, color filters, films for flexible displays, electronic parts, semiconductor devices, interlayer dielectrics, wiring-covering films, optical circuits, parts for optical circuits, antireflection films, and other optical members or electronic members.

—Radical-Generating Agent of the Present Invention—

The radical-generating agent of the present invention comprises the compound of the present invention (the compound represented by the general formula (A)), and generates a radical through irradiation with light (an active energy ray) such as ultraviolet rays, visible rays, infrared rays, and X-rays, or heating.

For allowing the radical-generating agent of the present invention to generate a radical therefrom through irradiation with light (an active energy ray), irradiation with light (an active energy ray), typically at wavelengths of 100 to 780 nm, preferably at wavelengths of 200 to 450 nm, can be suitably performed. The radical-generating agent of the present invention has a high molar absorption coefficient in an absorption wavelength region of 200 to 450 nm, and hence can efficiently generate a radical. In addition, it is preferred for the radical-generating agent of the present invention to exhibit absorption to at least one or more lights (active energy rays) of the i-ray, the h-ray, and the g-ray, within the wavelength region, from the viewpoint of versatility.

For allowing the radical-generating agent of the present invention to generate a radical therefrom through heating, the radical-generating agent of the present invention can generate a radical through thermal energy in heating typically at 150 to 400° C., preferably at 250 to 350° C.

The 5% weight loss temperature of the radical-generating agent of the present invention is preferably 150° C. or higher. In production of a cured film by using the radical-generating agent of the present invention, baking or the like is performed in some cases to cure a coating film. In a case where the 5% weight loss temperature of the radical-generating agent is high, the baking temperature can be set high, and hence, for example, the amount of residues of an organic solvent contained in the radical-curable resin composition of the present invention, which will be described later, can be as small as possible after baking. Thereby, deterioration of the contrast ratio between an exposed portion (a portion irradiated with light) and an unexposed portion (a portion not irradiated with light) by such a residual organic solvent can be reduced.

The radical-generating agent of the present invention may comprise an additive such as a sensitizer and an organic solvent in addition to the compound of the present invention (the compound represented by the general formula (A)), in a range that does not interfere the purpose and advantageous effects of the present invention. The additives may be used singly or in combinations of two or more. It should be noted that a commercially available product or a product appropriately synthesized by using a known method can be suitably used for the additive.

In addition, the radical-generating agent of the present invention can be used as a radical-generating agent in a resist removing agent in a surface treatment process for semiconductors, and use of a composition comprising the radical-generating agent of the present invention allows efficient removal of residues of a resist layer and residues of an antireflection film layer remaining after surface treatment of a semiconductor provided with an antireflection film layer or the like.

The radical-generating agent of the present invention can be suitably used for such a purpose, for example, according to contents described in any of International Publication Nos. WO 2009/110582, WO 2011/027772, and WO 2011/027773, and the quantity of the radical-generating agent of the present invention to be used, an additional substance to coexist therewith and the quantity thereof to be used, and so on, can be appropriately selected according to the contents described in the specification.

Moreover, the radical-generating agent of the present invention can be used as a catalyst for radical reaction in carbon-carbon bond-forming reaction with use of radical reaction.

The radical-generating agent of the present invention can be suitably used for such a purpose, for example, according to contents described in Japanese Patent Application Laid-Open Publication No. 11-5033, and the quantity of the radical-generating agent of the present invention to be used, an additional substance to coexist therewith and the quantity thereof to be used, and so on, can be appropriately selected according to the contents described in the publication.

In addition, the radical-generating agent of the present invention can form a polythioether by the progression of sequential polymerization through irradiation with light (an active energy ray) such as ultraviolet rays, visible rays, infrared rays, and X-rays, or heating, for example, in the presence of a thiol compounds and a compound having a carbon-carbon double bond.

The thiol compounds may be, without any limitation, any of such compounds typically used in the field. Specific examples of the thiol compounds include those exemplified for the thiol compounds to be used for the base-curable resin composition of the present invention. The thiol compounds may be used singly or in combinations of two or more. It should be noted that a commercially available product or a product appropriately synthesized by using a known method can be suitably used for the thiol compounds.

The compound having a carbon-carbon double bond may be, without any limitation, any of such compounds typically used in the field, and specific examples thereof include those described in Japanese Patent Application Laid-Open Publication Nos. 2007-291313 and 2014-28938, and so on, and further include maleimide derivatives such as N,N'-1,3-phenylenedimaleimide, N,N'-1,4-phenylenedimaleimide, N,N',N''-1,3,5-phenylenetrimaleimide, 1,2-bismaleimideethane, 1,6-bismaleimidehexane, 4,4'-bismaleimididediphenylmethane, and bis(3-ethyl-5-methyl-4-maleimidephenyl)methane; olefin compounds having two or more double bonds such as 1,3-butadiene, 1,3-pentadiene, 1,4-pentadiene, isoprene, 1,4-hexadiene, 1,5-hexadiene, 2,4-hexadiene, 2-methyl-1,4-pentadiene, 2,3-dimethyl-1,3-butadiene, 1,4-heptadiene, 1,5-heptadiene, 1,6-heptadiene, 2-methyl-1,5-hexadiene, 1,7-octadiene, 2,5-dimethyl-1,5-hexadiene, 1,5-cyclooctadiene, 1,8-nonadiene, 1,9-decadiene, 1,10-undecadiene, 1,11-dodecadiene, 1,12-tridecadiene, 1,13-tetradecadiene, tetraallyloxyethane, 1,3-divinylbenzene, 1,4-divinylbenzene, 1,3,5-trivinylbenzene, 1,3-diisopropenylbenzene, 1,4-diisopropenylbenzene, 1,3,5-triisopropenylbenzene, 3,3'-divinylbiphenyl, 3,4'-divinylbiphenyl, 4,4'-divinylbiphenyl, 4,4'-diisopropenylbiphenyl, 2,6-diisopropenylnaphthalene, and 1,2-bis(vinylphenyl)ethane; compounds having two allyl groups such as diethylene glycol diallyl ether, diallyl hexahydrophthalate, and diallyl chlorendate; compounds having three allyl groups such as triallyl trimellitate, 2,4,6-tris(allyloxy)-1,3,5-triazine, triallyl phosphate, triallyl isocyanurate, and 2,4,6-tris(allylthio)-1,3,5-triazine; and compounds having four or more allyl groups such as tetraallyl pyromellitate.

The content of the compound having a carbon-carbon double bond is preferably a content such that, with respect to the thiol compounds, the ratio of "equivalent of thiol group (equivalent of SH group)/equivalent of carbon-carbon double bond" is, for example, 0.3/1.7 to 1.7/0.3, and more preferably a content such that the ratio is 0.8/1.2 to 1.2/0.8.

—Radical-Curable Resin Composition of the Present Invention—

The radical-curable resin composition of the present invention comprises the compound of the present invention (the compound represented by the general formula (A)) and a radical-reactive compound, and has a property to cure through polymerization reaction, crosslinking reaction, or the like caused by the action of a radical generated from the compound of the present invention (the radical-generating agent).

"Radical-reactive compound" comprised in the radical-curable resin composition of the present invention is a collective term for compounds which react by the action of a radical generated from the compound of the present invention (the radical-generating agent) and cause polymerization reaction, crosslinking reaction, or the like. That is, the radical-reactive compound serves as a resin raw material having a property to cure by the action of a radical, and include various raw materials including those capable of becoming a polymer through polymerization of only one resin raw material (monomer, oligomer, or polymer), for example, by the action of a radical, and those capable of becoming a polymer through polymerization or crosslinking of a plurality of resin raw materials (monomer, oligomer, or polymer), for example, by the action of a radical. The radical-reactive compound may be any compound having at least one radical-polymerizable ethylenic unsaturated bond, and specific examples of the radical-reactive compound include acrylates; methacrylates; allylates; unsaturated carboxylic acids such as crotonic acid, isocrotonic acid, itaconic acid, and maleic acid; esters; urethanes; amides; amide anhydrides; acid amides; acrylonitrile; styrenic compounds; unsaturated polyesters; unsaturated polyethers; unsaturated polyamides; and unsaturated polyurethanes. The radical-reactive compounds may be used singly or in combinations of two or more.

The acrylates may be any of a monomer, an oligomer, or a polymer, and specific examples thereof include monofunctional alkyl acrylates, monofunctional ether group-containing acrylates, monofunctional carboxy-containing acrylates, bifunctional acrylates, and trifunctional or higher-functional acrylates. The acrylates may have been halogenated or hydrogenated. In addition, derivatives of the specific examples are included in examples of the acrylates. The acrylates may be used singly or in combinations of two or more. It should be noted that a commercially available product or a product appropriately synthesized by using a known method can be suitably used for the acrylates.

Specific examples of the monofunctional alkyl acrylates include methyl acrylate, ethyl acrylate, propyl acrylate, isopropyl acrylate, butyl acrylate, dicyclopentenyl acrylate, dicyclopentenyloxyethyl acrylate, hexyl acrylate, 2-ethylhexyl acrylate, cyclohexyl acrylate, octyl acrylate, decyl acrylate, lauryl acrylate, stearyl acrylate, isobornyl acrylate, benzyl acrylate, and isoamyl acrylate.

Specific examples of the monofunctional ether group-containing acrylates include 2-methoxyethyl acrylate, 1,3-butylene glycol methyl ether acrylate, butoxyethyl acrylate, methoxytriethylene glycol acrylate, methoxypolyethylene glycol #400 acrylate, methoxydipropylene glycol acrylate, methoxytripropylene glycol acrylate, methoxypolypropylene glycol acrylate, ethoxydiethylene glycol acrylate, ethylcarbitol acrylate, 2-ethylhexylcarbitol acrylate, tetrahydrofurfuryl acrylate, phenoxyethyl acrylate, phenoxydiethylene glycol acrylate, phenoxypolyethylene glycol acrylate, cresylpolyethylene glycol acrylate, 4-nonylphenoxyethyl acrylate, 4-nonylphenoxypolyethylene glycol acrylate, and glycidyl acrylate.

Specific examples of the monofunctional carboxy-containing acrylates include β-carboxyethyl acrylate, mono-acryloyloxyethyl succinate, ω-carboxypolycaprolactone monoacrylate, 2-acryloyloxyethyl hydrogenphthalate, 2-acryloyloxypropyl hydrogenphthalate, 2-acryloyloxypropyl tetrahydrohydrogenphthalate, and 2-acryloyloxypropyl hexahydrohydrogenphthalate.

Specific examples of monofunctional acrylates other than the monofunctional alkyl acrylates, the monofunctional ether group-containing acrylates, and the monofunctional carboxy-containing acrylates include N,N-dimethylaminoethyl acrylate, N,N-dimethylaminopropyl acrylate, morpholinoethyl acrylate, trimethylsiloxyethyl acrylate, diphenyl-2-acryloyloxyethyl phosphate, 2-acryloyloxyethyl acid phosphate, and caprolactone-modified 2-acryloyloxyethyl acid phosphate.

Specific examples of the bifunctional acrylates include 1,4-butanediol diacrylate, 1,6-hexanediol diacrylate, ethylene glycol diacrylate, diethylene glycol diacrylate, triethylene glycol diacrylate, tetraethylene glycol diacrylate, polyethylene glycol #200 diacrylate, polyethylene glycol #300 diacrylate, polyethylene glycol #400 diacrylate, polyethylene glycol #600 diacrylate, dipropylene glycol diacrylate, tripropylene glycol diacrylate, tetrapropylene glycol diacrylate, polypropylene glycol #400 diacrylate, polypropylene glycol #700 diacrylate, neopentyl glycol diacrylate, neopentyl glycol PO-modified diacrylate, neopentyl glycol hydroxypivalate diacrylate, caprolactone adduct diacrylate of neopentyl glycol hydroxypivalate, 1,6-hexanediol bis(2-hydroxy-3-acryloyloxypropyl)ether, 2,2-bis(4-acryloxypolyethoxyphenyl)propane, 1,9-nonanediol diacrylate, pentaerythritol diacrylate, pentaerythritol diacrylate monostearate, pentaerythritol diacrylate monobenzoate, bisphenol A-type diacrylate, EO-modified bisphenol A-type diacrylate, PO-modified bisphenol A-type diacrylate, hydrogenated bisphenol A-type diacrylate, EO-modified hydrogenated bisphenol A-type diacrylate, PO-modified hydrogenated bisphenol A-type diacrylate, bisphenol F-type diacrylate, EO-modified bisphenol F-type diacrylate, PO-modified bisphenol F-type diacrylate, EO-modified tetrabromobisphenol A-type diacrylate, tricyclodecanedimethylol diacrylate, and isocyanuric acid EO-modified diacrylate.

Specific examples of the trifunctional or higher-functional acrylates include glycerin PO-modified triacrylate, trimethylolethane triacrylate, trimethylolpropane triacrylate, trimethylolpropane EO-modified triacrylate, trimethylolpropane PO-modified triacrylate, isocyanuric acid EO-modified triacrylate, isocyanuric acid EO-modified ε-caprolactone-modified triacrylate, 1,3,5-triacryloylhexahydro-s-triazine, pentaerythritol triacrylate, dipentaerythritol triacrylate tripropionate, pentaerythritol tetraacrylate, dipentaerythritol tetraacrylate, dipentaerythritol pentaacrylate monopropionate, dipentaerythritol hexaacrylate, tetramethylolmethane tetraacrylate, oligoester tetraacrylate, and tris(acryloyloxy) phosphate.

The weight-average molecular weight of the acrylates in a case where it is an oligomer or a polymer is preferably 100 to 30,000, and more preferably 200 to 20,000 from the viewpoint of the thermal resistance, coating property, solubility in organic solvents, solubility in developing solutions, and so on, of the radical-curable resin composition of the present invention. If the weight-average molecular weight is lower than 100, then the strength of a cured film or a shaped product obtained from the radical-curable resin composition of the present invention may be insufficient. If the weight-average molecular weight is higher than 30,000, on the other hand, not only the viscosity of the acrylates itself may increase to degrade the solubility, but also it may be difficult to obtain a cured film with a homogeneous surface and constant thickness. It should be noted that the weight-average molecular weight is a value obtained through measurement with gel permeation chromatography followed by conversion of the measurement in terms of standard polystyrene.

The methacrylates may be any of a monomer, an oligomer, or a polymer, and specific examples thereof include monofunctional alkyl methacrylates, monofunctional ether group-containing methacrylates, monofunctional carboxy-containing methacrylates, bifunctional methacrylates, and trifunctional or higher-functional methacrylates. The methacrylates may have been halogenated or hydrogenated. In addition, derivatives of the specific examples are included in examples of the methacrylates. The methacrylates may be used singly or in combinations of two or more. It should be noted that a commercially available product or a product appropriately synthesized by using a known method can be suitably used for the methacrylates.

Specific examples of the monofunctional alkyl methacrylates include methyl methacrylate, ethyl methacrylate, propyl methacrylate, isopropyl methacrylate, butyl methacrylate, dicyclopentenyl methacrylate, dicyclopentenyloxyethyl methacrylate, hexyl methacrylate, 2-ethylhexyl methacrylate, cyclohexyl methacrylate, octyl methacrylate, decyl methacrylate, lauryl methacrylate, stearyl methacrylate, isobornyl methacrylate, benzyl methacrylate, and isoamyl methacrylate.

Specific examples of the monofunctional ether group-containing methacrylates include 2-methoxyethyl methacrylate, 1,3-butylene glycol methyl ether methacrylate, butoxyethyl methacrylate, methoxytriethylene glycol methacrylate, methoxypolyethylene glycol #400 methacrylate, methoxydipropylene glycol methacrylate, methoxytripropylene glycol methacrylate, methoxypolypropylene glycol methacrylate, ethoxydiethylene glycol methacrylate, ethylcarbitol methacrylate, 2-ethylhexylcarbitol methacrylate, tetrahydrofurfuryl methacrylate, phenoxyethyl methacrylate, phenoxydiethylene glycol methacrylate, phenoxypolyethylene glycol methacrylate, cresylpolyethylene glycol methacrylate, 4-nonylphenoxyethyl methacrylate, 4-nonylphenoxypolyethylene glycol methacrylate, and glycidyl methacrylate.

Specific examples of the monofunctional carboxy-containing methacrylates include β-carboxyethyl methacrylate, monomethacryloyloxyethyl succinate, ω-carboxypolycaprolactone monomethacrylate, 2-methacryloyloxyethyl hydrogenphthalate, 2-methacryloyloxypropyl hydrogenphthalate, 2-methacryloyloxypropyl tetrahydrohydrogenphthalate, and 2-methacryloyloxypropyl hexahydrohydrogenphthalate.

Specific examples of monofunctional methacrylates other than the monofunctional alkyl methacrylates, the monofunctional ether group-containing methacrylates, and the monofunctional carboxy-containing methacrylates include N,N-dimethylaminoethyl methacrylate, N,N-dimethylaminopropyl methacrylate, morpholinoethyl methacrylate, trimethylsiloxyethyl methacrylate, diphenyl-2-methacryloyloxyethyl phosphate, 2-methacryloyloxyethyl acid phosphate, and caprolactone-modified 2-methacryloyloxyethyl acid phosphate.

Specific examples of the bifunctional methacrylates include 1,4-butanediol dimethacrylate, 1,6-hexanediol dimethacrylate, ethylene glycol dimethacrylate, diethylene glycol dimethacrylate, triethylene glycol dimethacrylate, tetraethylene glycol dimethacrylate, polyethylene glycol #200 dimethacrylate, polyethylene glycol #300 dimethacrylate, polyethylene glycol #400 dimethacrylate, polyethylene glycol #600 dimethacrylate, dipropylene glycol dimethacrylate, tripropylene glycol dimethacrylate, tetrapropylene glycol dimethacrylate, polypropylene glycol #400 dimethacrylate, polypropylene glycol #700 dimethacrylate, neopentyl glycol dimethacrylate, neopentyl glycol PO-modified dimethacrylate, neopentyl glycol hydroxypivalate dimethacrylate, caprolactone adduct dimethacrylate of neopentyl glycol hydroxypivalate, 1,6-hexanediol bis(2-hydroxy-3-methacryloyloxypropyl)ether, 2,2-bis(4-methacryloxypolyethoxyphenyl)propane, 1,9-nonanediol dimethacrylate, pentaerythritol dimethacrylate, pentaerythritol dimethacrylate monostearate, pentaerythritol dimethacrylate monobenzoate, bisphenol A-type dimethacrylate, EO-modified bisphenol A-type dimethacrylate, PO-modified bisphenol A-type dimethacrylate, hydrogenated bisphenol A-type dimethacrylate, EO-modified hydrogenated bisphenol A-type dimethacrylate, PO-modified hydrogenated bisphenol A-type dimethacrylate, bisphenol F-type dimethacrylate, EO-modified bisphenol F-type dimethacrylate, PO-modified bisphenol F-type dimethacrylate, EO-modified tetrabromobisphenol A-type dimethacrylate, tricyclodecanedimethylol dimethacrylate, and isocyanuric acid EO-modified dimethacrylate.

Specific examples of the trifunctional or higher-functional methacrylates include glycerin PO-modified trimethacrylate, trimethylolethane trimethacrylate, trimethylolpropane trimethacrylate, trimethylolpropane EO-modified trimethacrylate, trimethylolpropane PO-modified trimethacrylate, isocyanuric acid EO-modified trimethacrylate, isocyanuric acid EO-modified ε-caprolactone-modified trimethacrylate, 1,3,5-trimethacryloylhexahydro-s-triazine, pentaerythritol trimethacrylate, dipentaerythritol trimethacrylate tripropionate, pentaerythritol tetramethacrylate, dipentaerythritol tetramethacrylate, dipentaerythritol pentamethacrylate monopropionate, dipentaerythritol hexamethacrylate, tetramethylolmethane tetramethacrylate, oligoester tetramethacrylate, and tris(methacryloyloxy)phosphate.

The weight-average molecular weight of the methacrylates in a case where it is an oligomer or a polymer is preferably 100 to 30,000, and more preferably 200 to 20,000 from the viewpoint of the thermal resistance, coating property, solubility in organic solvents, solubility in developing solutions, and so on, of the radical-curable resin composition of the present invention. If the weight-average molecular weight is lower than 100, then the strength of a cured film or a shaped product obtained from the radical-curable resin composition of the present invention may be insufficient. If the weight-average molecular weight is higher than 30,000, on the other hand, not only the viscosity of the methacrylates itself may increase to degrade the solubility, but also it may be difficult to obtain a cured film with a homogeneous surface and constant thickness. It should be noted that the weight-average molecular weight is a value obtained through measurement with gel permeation chromatography followed by conversion of the measurement in terms of standard polystyrene.

The allylates may be any of a monomer, an oligomer, or a polymer, and specific examples thereof include allyl glycidyl ether, diallyl phthalate, triallyl trimellitate, and triallyl isocyanurate. The allylates may have been halogenated or hydrogenated. In addition, derivatives of the specific examples are included in examples of the allylates. The allylates may be used singly or in combinations of two or more. It should be noted that a commercially available product or a product appropriately synthesized by using a known method can be suitably used for the allylates.

The weight-average molecular weight of the allylates in a case where it is an oligomer or a polymer is preferably 100 to 30,000, and more preferably 200 to 20,000 from the viewpoint of the thermal resistance, coating property, solubility in organic solvents, solubility in developing solutions, and so on, of the radical-curable resin composition of the present invention. If the weight-average molecular weight is lower than 100, then the strength of a cured film or a shaped product obtained from the radical-curable resin composition of the present invention may be insufficient. If the weight-average molecular weight is higher than 30,000, on the other hand, not only the viscosity of the allylates itself may increase to degrade the solubility, but also it may be difficult to obtain a cured film with a homogeneous surface and constant thickness. It should be noted that the weight-average molecular weight is a value obtained through measurement with gel permeation chromatography followed by conversion of the measurement in terms of standard polystyrene.

The acid amides may be any of a monomer, an oligomer, or a polymer, and specific examples thereof include acrylamide, N-methylolacrylamide, diacetone acrylamide, N,N-dimethylacrylamide, N,N-diethylacrylamide, N-isopropylacrylamide, acryloylmorpholine, methacrylamide, N-methylolmethacrylamide, diacetone methacrylamide, N,N-dimethylmethacrylamide, N,N-diethylmethacrylamide, N-isopropylmethacrylamide, and methacryloylmorpholine. The acid amides may have been halogenated or hydrogenated. In addition, derivatives of the specific examples are included in examples of the acid amides. The acid amides may be used singly or in combinations of two or more. It should be noted that a commercially available product or a product appropriately synthesized by using a known method can be suitably used for the acid amides.

The weight-average molecular weight of the acid amides in a case where it is an oligomer or a polymer is preferably 100 to 30,000, and more preferably 200 to 20,000 from the viewpoint of the thermal resistance, coating property, solubility in organic solvents, solubility in developing solutions, and so on, of the radical-curable resin composition of the present invention. If the weight-average molecular weight is lower than 100, then the strength of a cured film or a shaped product obtained from the radical-curable resin composition of the present invention may be insufficient. If the weight-average molecular weight is higher than 30,000, on the other hand, not only the viscosity of the acid amides itself may increase to degrade the solubility, but also it may be difficult to obtain a cured film with a homogeneous surface and constant thickness. It should be noted that the weight-average molecular weight is a value obtained through measurement with gel permeation chromatography followed by conversion of the measurement in terms of standard polystyrene.

The styrenic compounds may be any of a monomer, an oligomer, or a polymer, and specific examples thereof include styrene, 4-methylstyrene, 4-methoxystyrene, 4-tert-butoxystyrene, 4-tert-butoxycarbonylstyrene, 4-tert-butoxycarbonyloxystyrene, and 2,4-diphenyl-4-methyl-1-pentene. The styrenic compounds may have been halogenated or hydrogenated. In addition, derivatives of the specific examples are included in examples of the styrenic compounds. The styrenic compounds may be used singly or in combinations of two or more. It should be noted that a commercially available product or a product appropriately synthesized by using a known method can be suitably used for the styrenic compounds.

The weight-average molecular weight of the styrenic compounds in a case where it is an oligomer or a polymer is preferably 100 to 30,000, and more preferably 200 to 20,000 from the viewpoint of the thermal resistance, coating property, solubility in organic solvents, solubility in developing solutions, and so on, of the radical-curable resin composition of the present invention. If the weight-average molecular weight is lower than 100, then the strength of a cured film or a shaped product obtained from the radical-curable resin composition of the present invention may be insufficient. If the weight-average molecular weight is higher than 30,000, on the other hand, not only the viscosity of the styrenic compounds itself may increase to degrade the solubility, but also it may be difficult to obtain a cured film with a homogeneous surface and constant thickness. It should be noted that the weight-average molecular weight is a value obtained through measurement with gel permeation chromatography followed by conversion of the measurement in terms of standard polystyrene.

Specific examples of vinyl compounds other than the unsaturated carboxylic acids, the acid amides, and the styrenic compounds include vinyl acetate, vinyl monochloroacetate, vinyl benzoate, vinyl pivalate, vinyl butyrate, vinyl laurate, divinyl adipate, vinyl methacrylate, vinyl crotonate, vinyl 2-ethylhexanoate, N-vinylcarbazole, and N-vinylpyrrolidone.

The weight-average molecular weight of the vinyl compounds in a case where it is an oligomer or a polymer is preferably 100 to 30,000, and more preferably 200 to 20,000 from the viewpoint of the thermal resistance, coating property, solubility in organic solvents, solubility in developing solutions, and so on, of the radical-curable resin composition of the present invention. If the weight-average molecular weight is lower than 100, then the strength of a cured film or a shaped product obtained from the radical-curable resin composition of the present invention may be insufficient. If the weight-average molecular weight is higher than 30,000, on the other hand, not only the viscosity of the vinyl compounds itself may increase to degrade the solubility, but also it may be difficult to obtain a cured film with a homogeneous surface and constant thickness. It should be noted that the weight-average molecular weight is a value obtained through measurement with gel permeation chromatography followed by conversion of the measurement in terms of standard polystyrene.

The content of the compound of the present invention (the radical-generating agent) comprised in the radical-curable resin composition of the present invention may be, without any limitation, any content typically employed in the field, and, for example, the content is typically 0.1 to 100% by weight, preferably 1 to 50% by weight, and more preferably 5 to 30% by weight, with respect to the weight of the radical-reactive compound. If the content of the compound of the present invention (the radical-generating agent) is extremely low, the radical-curable resin composition of the present invention may be insufficiently cured. If the content of the compound of the present invention (the radical-generating agent) is very high, on the other hand, problems arise, such as deterioration of the economic efficiency.

In a case where the radical-curable resin composition of the present invention is used as a photosensitive resin composition, a sensitizer may be added to the composition to widen the photosensitive wavelength region for enhancement of the sensitivity. The sensitizer may be, without any limitation, any sensitizer typically used in the field, and specific examples of the sensitizer include those exemplified for the sensitizers to be used for the base-curable resin composition of the present invention. The sensitizers may be used singly or in combinations of two or more. It should be noted that a commercially available product or a product appropriately synthesized by using a known method can be suitably used for the sensitizer.

The content of the sensitizer contained in the radical-curable resin composition of the present invention, as necessary, may be, without any limitation, any content typically employed in the field, and, for example, the content can be appropriately determined in consideration of the kinds and quantities of the compound of the present invention (the radical-generating agent) and the radical-reactive compound to be used, required sensitivity and the like. More specifically, in a case where the sensitizer is contained, the content of the sensitizer is preferably 1 to 30% by weight, and more preferably 1 to 20% by weight, with respect to the total weight of the radical-curable resin composition of the present invention. If the content of the sensitizer is less than 1% by weight, enhancement of the sensitivity may be insufficient. If the content of the sensitizer is more than 30% by weight, on the other hand, enhancement of the sensitivity may be excessive.

When the radical-curable resin composition of the present invention is applied onto a given substrate, for example, it is desirable for the composition to contain an organic solvent in some cases. The organic solvent contained in the radical-curable resin composition of the present invention can enhance the coating property, and provides favorable workability. The organic solvent may be, without any limitation, any organic solvent typically used in the field. Specific examples of the organic solvent include those exemplified for the organic solvents to be used for the base-curable resin composition of the present invention. The organic solvents may be used singly or in combinations of two or more. It should be noted that a commercially available product can be suitably used for the organic solvent.

The content of the organic solvent contained in the radical-curable resin composition of the present invention, as necessary, may be, without any limitation, any content typically employed in the field, and, for example, the content can be appropriately determined so that homogenous application can be achieved when the radical-curable resin composition of the present invention is applied onto a given substrate to form a layer of the radical-curable resin composition of the present invention. The content of the organic solvent contained in the radical-curable resin composition of the present invention is, for example, typically 0.01 to 50 mL, preferably 0.05 to 30 mL, and more preferably 0.1 to 10 mL, with respect to 1 g of the radical-reactive compound.

The radical-curable resin composition of the present invention may contain an additive in addition to the radical-reactive compound, in a range that does not interfere the purpose and advantageous effects of the present invention, and examples of the additive may include pigments; dyes; polymerization inhibitors such as 4-methoxyphenol, hydroquinone, alkyl-substituted hydroquinone, catechol, tert-butyl catechol, phenothiazine, cupferron, and N-nitrosophenylhydroxyamine aluminum salt; curing accelerators or chain transfer catalysts such as amines including triethanolamine, N-phenylglycine, and N,N-diethylaniline, thiols, disulfides, thiones, O-acylthiohydroxamate, and N-alkyloxypyridinethiones; oxygen scavengers or reductants such as phosphine, phosphonate, and phosphite; anti-fogging agents; discoloration inhibitors; halation inhibitors; fluorescent brightening agents; surfactants; colorants; bulking agents; plasticizers; flame retardants; antioxidants; ultraviolet absorbers; foaming agents; fungicides; antistatic agents; magnetic substances; diluting solvents; and other additives to impart various properties. The additives may be used singly or in combinations of two or more. It should be noted that a commercially available product or a product appropriately synthesized by using a known method can be suitably used for the additive.

Patterning can be performed by using the radical-curable resin composition of the present invention, for example as follows: a coating solution is prepared with the radical-curable resin composition of the present invention; the coating solution prepared is applied onto an appropriate solid surface of a substrate or the like, and dried to form a coating film; patterning exposure is then performed for the coating film formed to allow the compound of the present invention (the radical-generating agent) to generate a radical therefrom; and thereafter polymerization reaction, crosslinking reaction, or the like of the radical-reactive compound contained in the radical-curable resin composition is promoted.

Known methods can be appropriately employed as a method for applying the radical-curable resin composition of the present invention onto a substrate, a method for irradiating with light (an active energy ray), a method for developing, and so on, each to be performed in the patterning.

The radical-curable resin composition of the present invention comprises the compound of the present invention (the radical-generating agent) and the radical-reactive compound, and thereby polymerization reaction, crosslinking reaction, or the like of the radical-reactive compound takes place by the action of a radical as an initiator generated from the compound of the present invention (the radical-generating agent) through an operation of, for example, irradiation with light (an active energy ray) or heating, and thus curing (polymerization) of the radical-reactive compound can effectively proceed. The radical-curable resin composition of the present invention, which has such an advantageous effect, for example, can be suitably used for curable materials, resist materials (patterning materials), and so on.

In a case where the radical-curable resin composition of the present invention is used for a curable material, a shaped product formed therefrom after curing reaction can be used for members in fields for which properties including thermal resistance, dimensional stability, and insulation properties are deemed effective, such as coating materials, printing inks, color filters, films for flexible displays, semiconductor devices, electronic parts, interlayer dielectrics, wiring-covering films, optical circuits, parts for optical circuits, antireflection films, and holograms. In addition, in a case where the radical-curable resin composition of the present invention is used for a resist material (patterning material), a cured film (pattern) or the like formed therefrom after patterning reaction has thermal resistance and insulating properties, and can be effectively used for, for example, color filters, films for flexible displays, electronic parts, semiconductor devices, interlayer dielectrics, wiring-covering films, optical circuits, parts for optical circuits, antireflection films, and other optical members or electronic members.

If the base-curable resin composition of the present invention further contains the radical-reactive compound, the composition can be cured through "hybrid curing" as a combination of curing with a base and curing with a radical. Specifically, the compound of the present invention can generate both a base and a radical, for example, through irradiation with light (an active energy ray) or heating, and hence, the composition in which the compound of the present invention is contained together with both the base-curable resin raw material and the radical-reactive compound enables simultaneous progression of two curing reactions, namely, anionic curing reaction of a strong base (biguanide) generated from the compound of the present invention (the base-generating agent) and the base-curable resin raw material, and radical-curing reaction of a radical generated from the compound of the present invention (the radical-generating agent) and the radical-reactive compound.

Patterning can be performed by using the hybrid curing, for example as follows: a coating solution is prepared with a composition containing the compound of the present invention, the base-curable resin raw material, and the radical-reactive compound; the coating solution prepared is applied onto an appropriate solid surface of a substrate or the like, and dried to form a coating film; patterning exposure is then performed for the coating film formed to allow the compound of the present invention to generate a base and a radical therefrom; and thereafter heating is performed under given conditions to promote both anionic curing reaction of the base-curable resin raw material and radical-curing reaction of the radical-reactive compound.

The base-curable resin raw material, the radical-reactive compound, an organic solvent, and an additional substance to coexist therewith for the hybrid curing may be, without any limitation, those typically used in the field, and any substance can be appropriately selected for use from the lists of specific examples of the base-curable resin raw material, the radical-reactive compound, the organic solvent, and the additive.

Known methods can be appropriately employed as a method for applying a composition containing the compound of the present invention, the base-curable resin raw material, and the radical-reactive compound onto a substrate, a method for baking, a method for irradiating with light (an active energy ray), a method for developing, and so on, each to be performed in the patterning.

EXAMPLES

Hereinafter, the present invention is specifically described with reference to Examples and Comparative Examples. However, the present invention is by no means limited to these Examples. It should be noted that % in the following examples is based on weight unless otherwise specified.

Synthetic Example 1: Synthesis of 1,2-dicyclohexyl-4,4,5,5-tetramethylbiguanide Carbonate To 12.2 g of 1,1,3,3-tetramethylguanidine (106 mmol; manufactured by Wako Pure Chemical Industries, Ltd.), 10.9 g of N,N'-dicyclohexylcarbodiimide (53 mmol; manufactured by Wako Pure Chemical Industries, Ltd.) was added, and the resultant was stirred with heating at 100° C. for 2 hours. After the completion of the reaction, the reaction solution was concentrated under reduced pressure to remove 1,1,3,3-tetramethylguanidine, and 20 mL of acetone and 2 mL of water were then added to the resulting residue, and dry ice was charged therein, and the resulting solid was collected by filtration to afford 8.44 g of 1,2-dicyclohexyl-4,4,5,5-tetramethylbiguanide carbonate (white powder, yield: 45%). The results of $^1$H-NMR and $^{13}$C-NMR measurements and the structure of 1,2-dicyclohexyl-4,4,5,5-tetramethylbiguanide carbonate are as follows.

$^1$H-NMR (400 MHz, D$_2$O) δ (ppm): 1.22-1.80 (40H, brm), 2.86 (24H, s), 3.02 (4H, m).

$^{13}$C-NMR (400 MHz, CD$_3$OD) δ (ppm): 26.1, 34.1, 40.1, 52.4, 158.0, 161.2, 164.4.

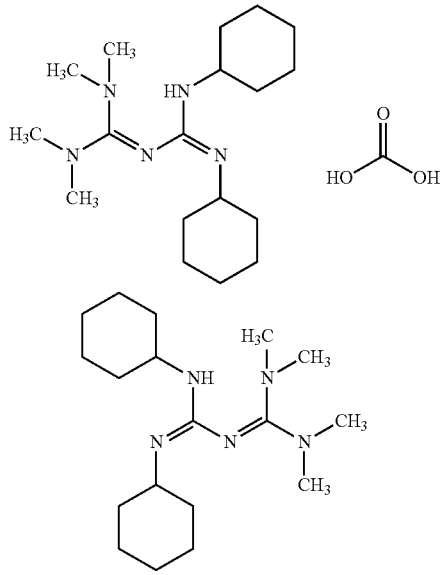

Synthetic Example 2: Synthesis of 1,2-diisopropyl-4,4,5,5-tetramethylbiguanide To 11.9 g of 1,1,3,3-tetramethylguanidine (10.3 mmol; manufactured by Wako Pure Chemical Industries, Ltd.), 13.1 g of N,N'-diisopropylcarbodiimide (10.3 mmol; manufactured by Wako Pure Chemical Industries, Ltd.) was added, and the resultant was stirred with heating at 100° C. for 2 hours. After the completion of the reaction, hexane was added to the reaction solution, and the reaction solution was cooled to 5° C., and the resulting solid was deliquored to afford 9.88 g of 1,2-diisopropyl-4,4,5,5-tetramethylbiguanide (white powder, yield: 39%). The result of $^1$H-NMR measurement and the structure of 1,2-diisopropyl-4,4,5,5-tetramethylbiguanide are as follows.

$^1$H-NMR (400 MHz, CDCl$_3$) δ (ppm): 1.10 (12H, d), 2.78 (13H, s), 3.38 (2H, q).

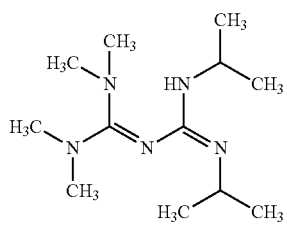

Synthetic Example 3: Synthesis of 1,2-bis(2,6-diisopropylphenyl)-4,4,5,5-tetramethylbiguanide To 3.18 g of 1,1,3,3-tetramethylguanidine (27.6 mmol; manufactured by Wako Pure Chemical Industries, Ltd.), 13.1 g of bis(2,6-diisopropylphenyl)carbodiimide (27.6 mmol; manufactured by Tokyo Chemical Industry Co., Ltd.) was added, and the resultant was stirred at room temperature for 30 minutes. After the completion of the reaction, hexane was added to the reaction solution, and the reaction solution was cooled to 5° C., and the resulting solid was deliquored to afford 10.20 g of 1,2-bis(2,6-diisopropylphenyl)-4,4,5,5-tetramethylbiguanide (white powder, yield: 77%). The result of $^1$H-NMR measurement and the structure of 1,2-bis(2,6-diisopropylphenyl)-4,4,5,5-tetramethylbiguanide are as follows.

$^1$H-NMR (400 MHz, CDCl$_3$) δ (ppm): 1.00-1.29 (24H, m), 2.81 (12H, s), 3.42-3.45 (4H, m), 4.85-4.95 (1H, brs), 7.07-7.26 (6H, m).

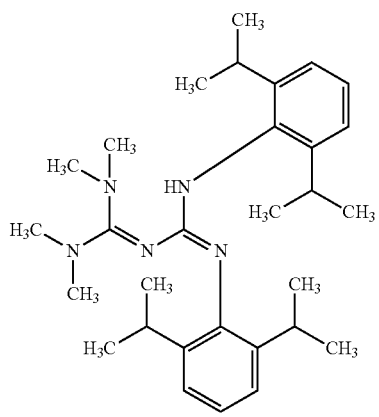 [SMILES: CC(C)c1cccc(C(C)C)c1/N=C(\N=C(N(C)C)N(C)C)Nc1c(C(C)C)cccc1C(C)C]

Synthetic Example 4: Synthesis of tetrakis(tetramethylguanidino)phosphonium Chloride Tetrakis(tetramethylguanidino)phosphonium chloride was synthesized according to a method described in German Patent Application Laid-Open Publication No. 102006010034. The structure of tetrakis(tetramethylguanidino)phosphonium chloride is as follows.

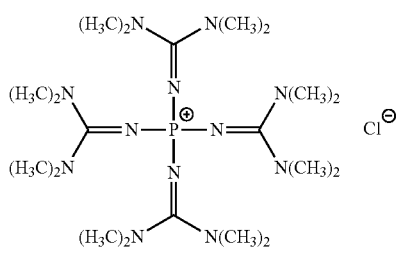

Synthetic Example 5: Synthesis of 1,3-dimethyl-2-(N',N',N'',N''-tetramethylguanidino)-4,5-dihydro-3H-imidazolium Chloride To 3.38 g of 2-chloro-1,3-dimethylimidazolinium chloride (20 mmol; manufactured by Wako Pure Chemical Industries, Ltd.), 20 mL of dichloromethane and 20 mL of tetrahydrofuran (THF) were added, and the resultant was cooled to 5° C., and then 4.6 g of 1,1,3,3-tetramethylguanidine (40 mmol; manufactured by Wako Pure Chemical Industries, Ltd.) was added thereto, and the resultant was stirred at 60° C. for 1.5 hours. After the completion of the reaction, 30 mL of acetone was added to the reaction solution, and a solid precipitated was removed by filtration. The resulting organic layer was concentrated under reduced pressure to afford 4.76 g of 1,3-dimethyl-2-(N',N',N'',N''-tetramethylguanidino)-4,5-dihydro-3H-imidazolium chloride (white powder, yield: 96%). The result of $^1$H-NMR and the structural formula of 1,3-dimethyl-2-(N',N',N'',N''-tetramethylguanidino)-4,5-dihydro-3H-imidazolium chloride are as follows.

$^1$H-NMR (400 MHz, D$_2$O) δ (ppm): 2.86 (6H, s), 3.04 (12H, s), 3.88 (4H, d).

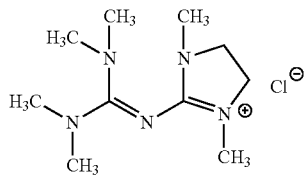

Synthetic Example 6: Synthesis of 2,3,4,6,7,8,9,10-octahydro-1-(phenylmethyl)-pyrimido[1,2-a]azepinium Bromide To 15.1 g of 1,8-diazabicyclo[5.4.0]undec-7-ene (100 mmol; manufactured by Wako Pure Chemical Industries, Ltd.), 30 mL of ethyl acetate was added, and the resultant was cooled to 10° C., and 17.1 g of benzyl bromide (100 mmol; manufactured by Wako Pure Chemical Industries, Ltd.) was then added thereto, and the resultant was stirred at room temperature for 3 hours. After the completion of the reaction, a solid precipitated was collected by filtration to afford 25.2 g of 2,3,4,6,7,8,9,10-octahydro-1-(phenylmethyl)-pyrimido[1,2-a]azepinium bromide (white powder, yield: 78%). The result of $^1$H-NMR measurement and the structural formula of 2,3,4,6,7,8,9,10-octahydro-1-(phenylmethyl)-pyrimido[1,2-a]azepinium bromide are as follows.

$^1$H-NMR (400 MHz, DMSO-d$_6$) δ (ppm): 1.49-1.58 (2H, m), 1.61-1.71 (4H, m), 2.01-2.11 (2H, m), 2.88-2.96 (m, 2H), 3.45-3.60 (4H, m), 3.65-3.75 (2H, m), 4.86 (2H, s), 7.29-7.38 (3H, m), 7.40-7.48 (2H, m).

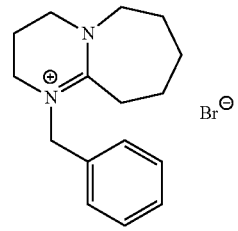 [SMILES: c1ccc(C[N+]2=C3CCCCCN3CCC2)cc1 ; [Br-]]

Synthetic Example 7: Synthesis of 1,2-diisopropyl-1,4,4,5,5-pentamethylbiguanide In 20 mL of anhydrous tetrahydrofuran, 1.00 g of 1,2-diisopropyl-4,4,5,5-tetramethylbiguanide (4.1 mmol ) obtained in Synthetic Example 2 and 0.3 g of 60% sodium hydride (4.1 mmol; manufactured by Wako Pure Chemical Industries, Ltd.) were dissolved, and the resultant was stirred at 50° C. for 1 hour. The reaction solution was then cooled to room temperature, and thereafter 0.63 g of methyl iodide (4.5 mmol; manufactured by Wako Pure Chemical Industries, Ltd.) was added thereto and reacted at room temperature for 1 hour. After the completion of the reaction, hexane was added to the reaction solution, and filtration was then performed with a Celite, and the resulting filtrate was concentrated under reduced pressure to afford 0.82 g of 1,2-diisopropyl-1,4,4,5,5-pentamethylbiguanide (pale yellow oil, yield: 78%). The result of $^1$H-NMR measurement and the structural formula of 1,2-diisopropyl-1,4,4,5,5-pentamethylbiguanide are as follows.

$^1$H-NMR (400 MHz, CDCl$_3$) δ (ppm): 1.04 (12H, s), 2.83 (15H, s), 3.03 (1H, brs), 4.45 (1H, brs).

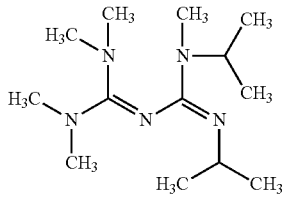

Example 1: Synthesis of 1,2-dicyclohexyl-4,4,5,5-tetramethylbiguanidium tetrakis(3-fluorophenyl)borate (Compound Represented by the Formula (1))

To a solution prepared by dissolving 7.09 g of trifluoroborane-diethyl ether complex (50 mmol; manufactured by Wako Pure Chemical Industries, Ltd.) in 5 mL of tetrahydrofuran, 5.34 g of magnesium powder (200 mmol; manufactured by Wako Pure Chemical Industries, Ltd.) was added, and then a tetrahydrofuran solution (30 mL) containing 38.5 g of 3-bromofluorobenzene (200 mmol; manufactured by Tokyo Chemical Industry Co., Ltd.) was added thereto dropwise, and reacted under reflux for 1 hour. Subsequently, the reaction solution was cooled to room temperature, and then a solution prepared by dissolving 20.14 g of 1,2-dicyclohexyl-4,4,5,5-tetramethylbiguanide carbonate (26 mmol) obtained in Synthetic Example 1 in 3.5% hydrochloric acid (55 mL, 53 mmol) was added thereto dropwise, and the reaction solution was stirred at room temperature for 30 minutes. After the completion of the reaction, ethyl acetate was added to the reaction solution, the reaction solution is extracted, and the organic layer after the extraction was washed with water and then concentrated under reduced pressure, and the resulting residue was purified by using silica gel column chromatography to afford 9.40 g of 1,2-dicyclohexyl-4,4,5,5-tetramethylbiguanidium tetrakis(3-fluorophenyl)borate (white powder, yield: 25%). The result of $^1$H-NMR measurement and the structure of 1,2-dicyclohexyl-4,4,5,5-tetramethylbiguanidium tetrakis(3-fluorophenyl)borate are as follows.

$^1$H-NMR (400 MHz, CDCl$_3$) δ (ppm): 1.06-1.24 (10H, m), 1.58-1.60 (2H, m), 1.70-1.78 (8H, m), 2.72 (12H, s), 3.05-3.15 (2H, m), 4.25-4.35 (2H, brs), 6.59-6.64 (4H, m), 6.95-6.99 (4H, m), 7.04-7.10 (4H, m), 7.11-7.13 (4H, m).

(1)

Example 2: Synthesis of 1,2-dicyclohexyl-4,4,5,5-tetramethylbiguanidium tetrakis(3,5-difluorophenyl)borate (Compound Represented by the Formula (2))

Operations were performed in the same manner as in Example 1 except that 1-bromo-3,5-difluorobenzene (manufactured by Wako Pure Chemical Industries, Ltd.) was used in place of 3-bromofluorobenzene (manufactured by Tokyo Chemical Industry Co., Ltd.), and 1.13 g of 1,2-dicyclohexyl-4,4,5,5-tetramethylbiguanidium tetrakis(3,5-difluorophenyl)borate (white powder, yield: 39%) was obtained. The result of $^1$H-NMR measurement and the structure of 1,2-dicyclohexyl-4,4,5,5-tetramethylbiguanidium tetrakis(3,5-difluorophenyl)borate are as follows.

$^1$H-NMR (400 MHz, CDCl$_3$) δ (ppm): 1.07-1.31 (10H, m), 1.63-1.85 (10H, m), 2.85 (12H, s), 3.20-3.30 (2H, m), 3.35-3.50 (2H, brs), 6.36-6.42 (4H, m), 6.72-6.75 (8H, m).

(2)

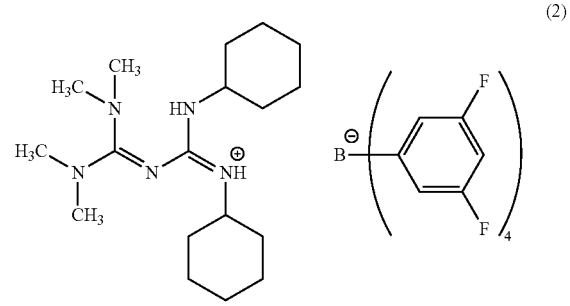

Example 3: Synthesis of 1,2-dicyclohexyl-4,4,5,5-tetramethylbiguanidium tetrakis(3-trifluoromethylphenyl)borate (Compound Represented by the Formula (3))

Operations were performed in the same manner as in Example 1 except that 3-bromotrifluoromethylbenzene (manufactured by Wako Pure Chemical Industries, Ltd.) was used in place of 3-bromofluorobenzene (manufactured by Tokyo Chemical Industry Co., Ltd.), and 0.64 g of 1,2-dicyclohexyl-4,4,5,5-tetramethylbiguanidium tetrakis(3-trifluorophenyl)borate (pale yellow powder, yield: 10%) was obtained. The result of $^1$H-NMR measurement and the structure of 1,2-dicyclohexyl-4,4,5,5-tetramethylbiguanidium tetrakis(3-trifluoromethylphenyl)borate are as follows.

$^1$H-NMR (400 MHz, CDCl$_3$) δ (ppm): 1.07-1.32 (10H, m), 1.55-1.63 (2H, m), 1.70-1.74 (4H, m), 1.82-1.84 (4H, m), 2.59 (12H, s), 3.20-3.35 (2H, brm), 4.45-4.60 (2H, brs), 7.16-7.22 (8H, m), 7.45-7.55 (4H, m), 7.55-7.65 (4H, m).

(3)

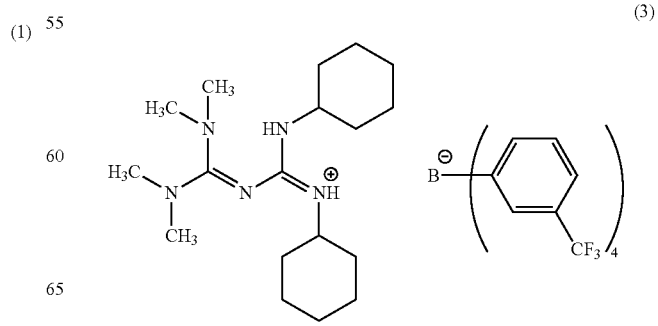

Example 4: Synthesis of 1,2-diisopropyl-4,4,5,5-tetramethylbiguanidium tetrakis(3-fluorophenyl)borate (Compound Represented by the Formula (4))

Operations were performed in the same manner as in Example 1 except that 1,2-diisopropyl-4,4,5,5-tetramethylbiguanide obtained in Synthetic Example 2 was used in place of 1,2-dicyclohexyl-4,4,5,5-tetramethylbiguanide carbonate, and 2.20 g of 1,2-diisopropyl-4,4,5,5-tetramethylbiguanidium tetrakis(3-fluorophenyl)borate (pale yellow oil, yield: 77%) was obtained. The result of $^1$H-NMR measurement and the structure of 1,2-diisopropyl-4,4,5,5-tetramethylbiguanidium tetrakis(3-fluorophenyl)borate are as follows.

$^1$H-NMR (400 MHz, CDCl$_3$) δ (ppm): 1.08 (12H, s), 2.70 (12H, s), 3.40-3.50 (2H, m), 5.05-5.25 (2H, brs), 6.58-6.63 (4H, m), 6.95-7.11 (12H, m).

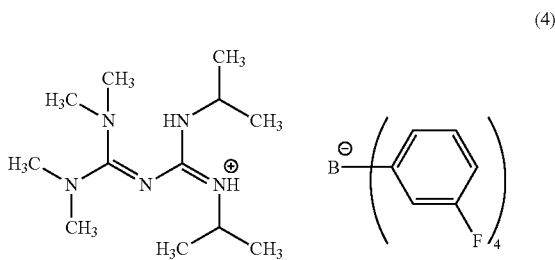

(4)

Example 5: Synthesis of 1,2-bis(2,6-diisopropylphenyl)-4,4,5,5-tetramethylbiguanidium tetrakis(3-fluorophenyl)borate (Compound Represented by the Formula (5))

Operations were performed in the same manner as in Example 1 except that 1,2-bis(2,6-diisopropylphenyl)-4,4,5,5-tetramethylbiguanide obtained in Synthetic Example 3 was used in place of 1,2-dicyclohexyl-4,4,5,5-tetramethylbiguanide carbonate, and 0.18 g of 1,2-bis(2,6-diisopropylphenyl)-4,4,5,5-tetramethylbiguanidium tetrakis(3-fluorophenyl)borate (colorless oil, yield: 8%) was obtained. The result of $^1$H-NMR measurement and the structure of 1,2-bis(2,6-diisopropylphenyl)-4,4,5,5-tetramethylbiguanidium tetrakis(3-fluorophenyl)borate are as follows.

$^1$H-NMR (400 MHz, CDCl$_3$) δ (ppm): 1.00-1.05 (6H, m), 1.14 (6H, d), 1.20-1.30 (6H, m), 1.37-1.39 (6H, d), 2.74 (12H, s), 2.99-3.06 (2H, m), 3.20-3.25 (2H, m), 5.75-5.85 (1H, brs), 6.10-6.20 (1H, brd), 6.41-6.64 (6H, m), 6.91-6.97 (6H, m), 7.14-7.16 (6H, m), 7.29-7.34 (4H, m).

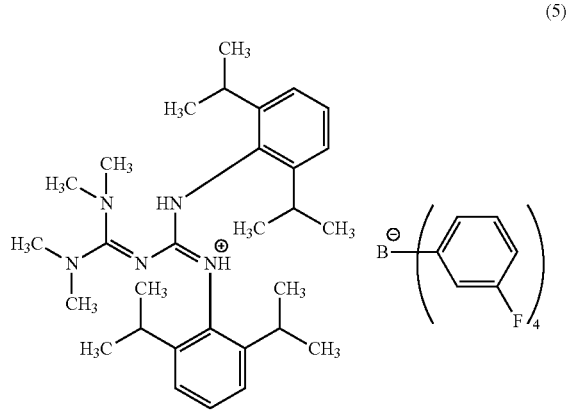

(5)

Comparative Example 1: Synthesis of 1,2-dicyclohexyl-4,4,5,5-tetramethylbiguanidium triphenyl(n-butyl)borate (Compound Represented by the Formula (101))

To a solution prepared by dissolving 1.41 g of 1,2-dicyclohexyl-4,4,5,5-tetramethylbiguanide carbonate (2.0 mmol) obtained in Synthetic Example 1 in 10% hydrochloric acid (1.5 mL, 4.0 mmol), 6.12 g of an aqueous solution of 20% lithium triphenyl(n-butyl)borate (4.0 mmol; manufactured by HOKKO CHEMICAL INDUSTRY CO., LTD.) was added, and the resultant was stirred at room temperature for 30 minutes. After the completion of the reaction, ethyl acetate was added to the reaction solution, the reaction solution is extracted, and the organic layer after the extraction was washed with water and then concentrated under reduced pressure to afford 1.83 g of 1,2-dicyclohexyl-4,4,5,5-tetramethylbiguanidium triphenyl(n-butyl)borate (white powder, yield: 73%). The result of $^1$H-NMR measurement and the structure of 1,2-dicyclohexyl-4,4,5,5-tetramethylbiguanidium triphenyl(n-butyl)borate are as follows.

$^1$H-NMR (400 MHz, CDCl$_3$) δ (ppm): 0.81 (3H, t), 1.02 (2H, m), 1.03-1.14 (12H, brm), 1.27-1.30 (2H, m), 1.50-1.70 (10H, brm), 2.75 (12H, s), 2.76-2.78 (3H, brm), 4.37 (1H, brs), 6.87 (3H, t), 7.04-7.08 (6H, m), 7.44-7.46 (6H, m).

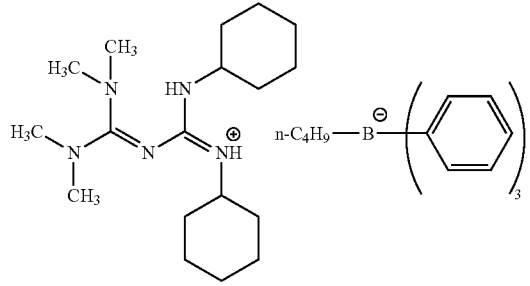

(101)

Comparative Example 2: Synthesis of 1,2-dicyclohexyl-4,4,5,5-tetramethylbiguanidium tris(3-fluorophenyl)(n-butyl)borate (Compound Represented by the Formula (102))

To a solution prepared by dissolving 1.42 g of trifluoroborane-diethyl ether complex (10 mmol; manufactured by Wako Pure Chemical Industries, Ltd.) in 5 mL of tetrahydrofuran, 1.09 g of magnesium powder (45 mmol; manufactured by Wako Pure Chemical Industries, Ltd.) was added, and then a tetrahydrofuran solution (15 mL) containing 5.25 g of 3-bromofluorobenzene (30 mmol; manufactured by Tokyo Chemical Industry Co., Ltd.) was added thereto dropwise, and reacted under reflux for 1 hour. Thereafter, a tetrahydrofuran solution (15 mL) containing 2.05 g of 1-bromobutane (15 mmol, manufactured by Wako Pure Chemical Industries, Ltd.) was added thereto dropwise, and reacted under reflux for 1 hour. Subsequently, the reaction solution was cooled to room temperature, and then a solution prepared by dissolving 5.29 g of 1,2-dicyclohexyl-4,4,5,5-tetramethylbiguanidium carbonate (7.5 mmol) obtained in Synthetic Example 1 in 3.5% hydrochloric acid (16 mL, 15 mmol) was added thereto dropwise, and the reaction solution was stirred at room temperature for 30 minutes. After the completion of the reaction, ethyl acetate was added to the reaction solution, the reaction solution is extracted, and the organic layer after the extraction was washed with water and then concentrated under reduced pressure, and the resulting residue was purified by using silica gel column chromatography to afford 4.03 g of 1,2-dicyclohexyl-4,4,5,5-tetramethylbiguanidium tris(3-fluorophenyl)(n-butyl)borate (pale yellow oil, yield: 59%). The result of $^1$H-NMR measurement and the structure of 1,2-dicyclohexyl-4,4,5,5-tetramethylbiguanidium tris(3-fluorophenyl)(n-butyl)borate are as follows.

$^1$H-NMR (400 MHz, CDCl$_3$) δ (ppm): 0.82-0.94 (4H, m), 1.07-1.29 (16H, m), 1.71-1.77 (9H, m), 2.73 (12H, s), 3.00-3.10 (2H, brm), 4.60-4.70 (2H, brs), 6.59-6.64 (3H, m), 6.90-7.11 (9H, m).

(102)

Comparative Example 3: Synthesis of 1,2-dicyclohexyl-4,4,5,5-tetramethylbiguanidium tetrakis(2-fluorophenyl)borate (Compound Represented by the Formula (103))

Operations were performed in the same manner as in Example 1 except that 2-bromofluorobenzene (manufactured by Wako Pure Chemical Industries, Ltd.) was used in place of 3-bromofluorobenzene (manufactured by Tokyo Chemical Industry Co., Ltd.), and 0.18 g of 1,2-dicyclohexyl-4,4,5,5-tetramethylbiguanidium tetrakis(2-fluorophenyl)borate (white powder, yield: 3%) was obtained. The result of $^1$H-NMR measurement and the structure of 1,2-dicyclohexyl-4,4,5,5-tetramethylbiguanidium tetrakis(2-fluorophenyl)borate are as follows.

$^1$H-NMR (400 MHz, CDCl$_3$) δ (ppm): 0.97-1.15 (10H, m), 1.52-1.71 (10H, m), 2.75 (12H, s), 2.85-2.95 (2H, brs), 4.26-4.28 (2H, brm), 6.65-6.70 (4H, m), 6.89-7.08 (8H, m), 7.35-7.45 (4H, m).

(103)

Comparative Example 4: Synthesis of 1,2-dicyclohexyl-4,4,5,5-tetramethylbiguanidium tetrakis(4-fluorophenyl)borate (Compound Represented by the Formula (104))

Operations were performed in the same manner as in Example 1 except that 4-bromofluorobenzene (manufactured by Wako Pure Chemical Industries, Ltd.) was used in place of 3-bromofluorobenzene (manufactured by Tokyo Chemical Industry Co., Ltd.), and 1.05 g of 1,2-dicyclohexyl-4,4,5,5-tetramethylbiguanidium tetrakis(4-fluorophenyl)borate (white powder, yield: 73%) was obtained. The result of $^1$H-NMR measurement and the structure of 1,2-dicyclohexyl-4,4,5,5-tetramethylbiguanidium tetrakis(4-fluorophenyl)borate are as follows.

$^1$H-NMR (400 MHz, (CD$_3$)$_2$CO) δ (ppm): 1.10-1.14 (6H, m), 1.29-1.34 (8H, m), 1.55-1.65 (2H, m), 1.73-1.75 (4H, m), 2.93 (12H, s), 3.55-3.70 (2H, m), 6.50-6.60 (2H, brs), 6.67-6.72 (8H, m), 7.17-7.21 (8H, m).

(104)

Comparative Example 5: Synthesis of 1,2-dicyclohexyl-4,4,5,5-tetramethylbiguanidium tetrakis(3-chlorophenyl)borate (Compound Represented by the Formula (105))

Operations were performed in the same manner as in Example 1 except that 3-bromochlorobenzene (manufactured by Wako Pure Chemical Industries, Ltd.) was used in place of 3-bromofluorobenzene (manufactured by Tokyo Chemical Industry Co., Ltd.), and 2.66 g of 1,2-dicyclohexyl-4,4,5,5-tetramethylbiguanidium tetrakis(3-chlorophenyl)borate (colorless oil, yield: 48%) was obtained. The result of $^1$H-NMR measurement and the structure of 1,2-dicyclohexyl-4,4,5,5-tetramethylbiguanidium tetrakis(3-chlorophenyl)borate are as follows.

$^1$H-NMR (400 MHz, CDCl$_3$) δ (ppm): 1.05-1.23 (10H, m), 1.60-1.67 (2H, m), 1.69-1.77 (8H, m), 2.67 (12H, s), 3.10-3.20 (2H, brm), 4.50-4.60 (2H, brs), 6.90-6.93 (4H, m), 7.00-7.04 (4H, m), 7.16-7.24 (8H m)).

(105)

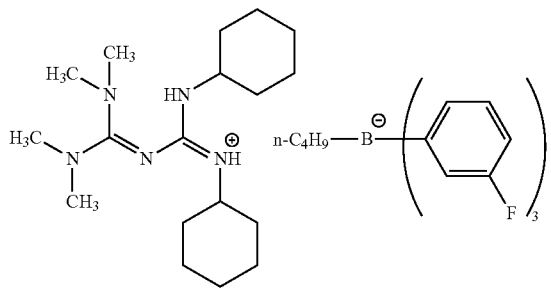

Comparative Example 6: Synthesis of 1,2-dicyclohexyl-4,4,5,5-tetramethylbiguanidium tetrakis[3,5-bis(trifluoromethyl)phenyl]borate (Compound Represented by the Formula (106))

To a methanol solution (2.0 mL) containing 39.8 mg of 1,2-dicyclohexyl-4,4,5,5-tetramethylbiguanide carbonate (0.057 mmol) obtained in Synthetic Example 1, 35% hydrochloric acid (0.01 mL, 0.114 mmol) was added, and then 0.72 g of sodium tetrakis[3,5-bis(trifluoromethyl)phenyl]borate hydrate (0.113 mmol; manufactured by Tokyo Chemical Industry Co., Ltd.) was added thereto, and the resultant was stirred at room temperature for 30 minutes. After the completion of the reaction, ethyl acetate was added to the reaction solution, the reaction solution is extracted, and the organic layer after the extraction was washed with water and then concentrated under reduced pressure to afford 98.2 mg of 1,2-dicyclohexyl-4,4,5,5-tetramethylbiguanidium tetrakis[3,5-bis(trifluoromethyl)phenyl]borate (brown oil, yield: 73%). The result of $^1$H-NMR measurement and the structure of 1,2-dicyclohexyl-4,4,5,5-tetramethylbiguanidium tetrakis[3,5-bis(trifluoromethyl)phenyl]borate are as follows.

$^1$H-NMR (400 MHz, CDCl$_3$) δ (ppm): 1.15-1.31 (10H, m), 1.55-1.73 (6H, m), 1.87-1.90 (4H, d), 2.79 (12H, s), 3.25-3.40 (2H, m), 4.30-4.40 (2H, brs), 7.53 (4H, s), 7.69 (8H, s).

(106)

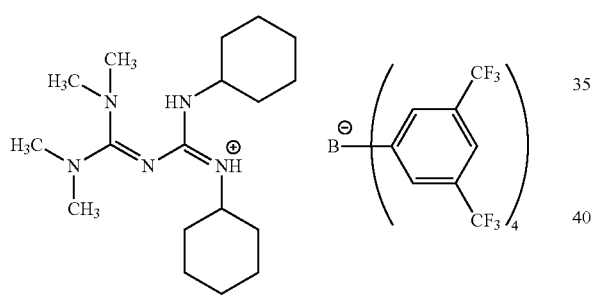

Comparative Example 7: Synthesis of 1,2-dicyclohexyl-4,4,5,5-tetramethylbiguanidium tetrakis(pentafluorobenzene)borate (Compound Represented by the Formula (107))

To a methanol solution (2.0 mL) containing 0.71 mg of 1,2-dicyclohexyl-4,4,5,5-tetramethylbiguanide carbonate (2.0 mmol) obtained in Synthetic Example 1, 35% hydrochloric acid (0.4 mL, 4.0 mmol) was added, and then 1.37 g of lithium tetrakis(pentafluorophenyl)borate (2.0 mmol; manufactured by Tosoh Finechem Corporation) was added thereto, and the resultant was stirred at room temperature for 30 minutes. After the completion of the reaction, ethyl acetate was added to the reaction solution, the reaction solution is extracted, and the organic layer after the extraction was washed with water and then concentrated under reduced pressure to afford 1.89 g of 1,2-dicyclohexyl-4,4,5,5-tetramethylbiguanidium tetrakis(pentafluorobenzene)borate (brown amorphous substance, yield: 94%). The result of $^1$H-NMR measurement and the structure of 1,2-dicyclohexyl-4,4,5,5-tetramethylbiguanidium tetrakis(pentafluorobenzene)borate are as follows.

$^1$H-NMR (400 MHz, CDCl$_3$) δ (ppm): 1.14-1.33 (10H, m), 1.64-1.67 (2H, m), 1.74-1.77 (4H, m), 1.89-1.92 (4H, m), 2.87 (12H, s), 3.22-3.44 (2H, m), 4.40-4.55 (2H, brs).

(107)

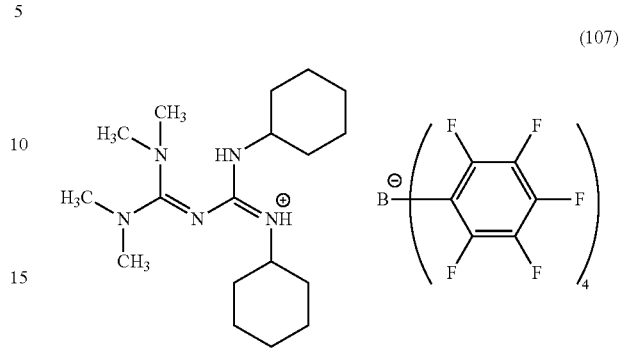

Comparative Example 8: Synthesis of 1,5,7-triazabicyclo[4.4.0]dec-5-enium tetrakis(3-fluorophenyl)borate (Compound Represented by the Formula (108))

Operations were performed in the same manner as in Example 1 except that 1,5,7-triazabicyclo[4.4.0]dec-5-ene (TBD) (manufactured by Tokyo Chemical Industry Co., Ltd.) was used in place of 1,2-dicyclohexyl-4,4,5,5-tetramethylbiguanide carbonate, and 0.80 g of 1,5,7-triazabicyclo[4.4.0]dec-5-enium tetrakis(3-fluorophenyl)borate (white powder, yield: 33%) was obtained. The result of $^1$H-NMR measurement and the structure of 1,5,7-triazabicyclo[4.4.0]dec-5-enium tetrakis(3-fluorophenyl)borate are as follows.

$^1$H-NMR (400 MHz, CDCl$_3$) δ (ppm): 1.75-1.80 (4H, m), 2.76-2.79 (4H, m), 3.06-3.09 (4H, m), 3.30-3.40 (2H, brs), 6.65-6.69 (4H, m), 7.01-7.26 (12H, m).

(108)

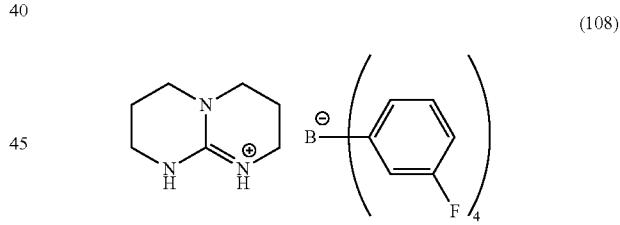

Comparative Example 9: Synthesis of 1,8-diazabicyclo[5.4.0]-7-undecenium tetrakis(3-fluorophenyl)borate (Compound Represented by the Formula (109))

Operations were performed in the same manner as in Example 1 except that 1,8-diazabicyclo[5.4.0]-7-undecene (DBU) (manufactured by Wako Pure Chemical Industries, Ltd.) was used in place of 1,2-dicyclohexyl-4,4,5,5-tetramethylbiguanide carbonate, and 1.56 g of 1,8-diazabicyclo[5.4.0]-7-undecenium tetrakis(3-fluorophenyl)borate (white powder, yield: 63%) was obtained. The result of $^1$H-NMR measurement and the structure of 1,8-diazabicyclo[5.4.0]-7-undecenium tetrakis(3-fluorophenyl)borate are as follows.

$^1$H-NMR (400 MHz, CDCl$_3$) δ (ppm): 1.49-1.67 (8H, m), 2.10-2.30 (2H, m), 2.75-2.95 (2H, m), 3.07-3.19 (5H, m), 6.60-6.63 (4H, m), 6.95-7.20 (12H, m).

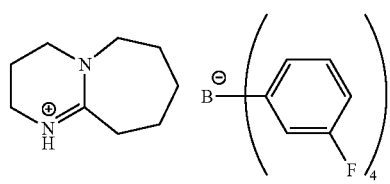

(109)

Comparative Example 10: Synthesis of 8-dimethylamino-1-naphthyldimethylammonium tetrakis(3-fluorophenyl)borate (Compound Represented by the Formula (110))

Operations were performed in the same manner as in Example 1 except that 1,8-bis(dimethylamino)naphthalene (manufactured by Tokyo Chemical Industry Co., Ltd.) was used in place of 1,2-dicyclohexyl-4,4,5,5-tetramethylbiguanide carbonate, and 1.68 g of 8-dimethylamino-1-naphthyldimethylammonium tetrakis(3-fluorophenyl)borate (white powder, yield: 61%) was obtained. The result of $^1$H-NMR measurement and the structure of 8-dimethylamino-1-naphthyldimethylammonium tetrakis(3-fluorophenyl)borate are as follows.

$^1$H-NMR (400 MHz, $(CD_3)_2CO$) δ (ppm): 3.33 (13H, s), 6.50-6.60 (4H, m), 6.94-7.07 (12H, m), 7.76 (2H, t), 8.09-8.14 (4H, m).

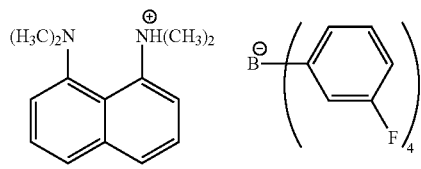

(110)

Comparative Example 11: Synthesis of 7-methyl-1,5,7-triazabicyclo[4.4.0]dec-5-enium tetrakis(3-fluorophenyl)borate (Compound Represented by the Formula (111))

Operations were performed in the same manner as in Example 1 except that 7-methyl-1,5,7-triazabicyclo[4.4.0]dec-5-ene (MTBD) (manufactured by Wako Pure Chemical Industries, Ltd.) was used in place of 1,2-dicyclohexyl-4,4,5,5-tetramethylbiguanide carbonate, and 1.94 g of 7-methyl-1,5,7-triazabicyclo[4.4.0]dec-5-enium tetrakis(3-fluorophenyl)borate (pale yellow powder, yield: 79%) was obtained. The result of $^1$H-NMR measurement and the structure of 7-methyl-1,5,7-triazabicyclo[4.4.0]dec-5-enium tetrakis(3-fluorophenyl)borate are as follows.

$^1$H-NMR (400 MHz, $CDCl_3$) δ (ppm): 1.65-1.68 (2H, m), 1.76-1.79 (2H, m), 2.28 (3H, s), 2.75-2.85 (2H, m), 2.90-3.10 (6H, m), 4.05-4.15 (1H, brs), 6.59-6.63 (4H, m), 6.95-7.26 (12H, m).

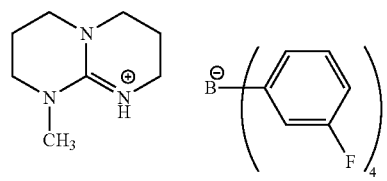

(111)

Comparative Example 12: Synthesis of 2-ethyl-4-methylimidazolium tetrakis(3-fluorophenyl)borate (Compound Represented by the Formula (112))

Operations were performed in the same manner as in Example 1 except that 2-ethyl-4-methylimidazole (manufactured by Wako Pure Chemical Industries, Ltd.) was used in place of 1,2-dicyclohexyl-4,4,5,5-tetramethylbiguanide carbonate, and 0.85 g of 2-ethyl-4-methylimidazolium tetrakis(3-fluorophenyl)borate (white powder, yield: 37%) was obtained. The result of $^1$H-NMR measurement and the structure of 2-ethyl-4-methylimidazolium tetrakis(3-fluorophenyl)borate are as follows.

$^1$H-NMR (400 MHz, $(CD_3)_2CO$) δ (ppm): 1.42 (3H, t), 2.36 (3H, s), 3.11 (2H, q), 6.50-6.60 (4H, m), 6.90-7.10 (12H, m), 7.30 (1H, s), 12.50-13.00 (2H, brs).

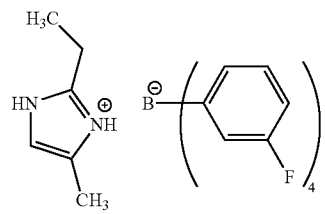

(112)

Comparative Example 13: Synthesis of 1,1,3,3-tetramethylguanidium tetrakis(3-fluorophenyl)borate (Compound Represented by the Formula (113))

Operations were performed in the same manner as in Example 1 except that 1,1,3,3-tetramethylguanidine (manufactured by Wako Pure Chemical Industries, Ltd.) was used in place of 1,2-dicyclohexyl-4,4,5,5-tetramethylbiguanide carbonate, and 0.80 g of 1,1,3,3-tetramethylguanidium tetrakis(3-fluorophenyl)borate (white powder, yield: 35%) was obtained. The result of $^1$H-NMR measurement and the structure of 1,1,3,3-tetramethylguanidium tetrakis(3-fluorophenyl)borate are as follows.

$^1$H-NMR (400 MHz, $(CD_3)_2CO$) δ (ppm): 3.11 (12H, s), 6.55-6.62 (4H, m), 6.92-7.10 (12H, m), 7.30-7.42 (2H, brs).

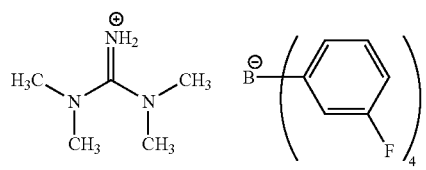

(113)

Comparative Example 14: Synthesis of tetrakis(tetramethylguanidino)phosphonium tetrakis(3-fluorophenyl)borate (Compound Represented by the Formula (114))

Operations were performed in the same manner as in Example 1 except that tetrakis(tetramethylguanidino)phosphonium chloride obtained in Synthetic Example 4 was used in place of 1,2-dicyclohexyl-4,4,5,5-tetramethylbiguanide carbonate and 3.5% hydrochloric acid, and 2.78 g of tetrakis(tetramethylguanidino)phosphonium tetrakis(3-fluorophenyl)borate (yellow oil, yield: 70%) was obtained. The result of $^1$H-NMR measurement and the structure of tetrakis(tetramethylguanidino)phosphonium tetrakis(3-fluorophenyl)borate are as follows.

$^1$H-NMR (400 MHz, CDCl$_3$) δ (ppm): 2.74 (48H, s), 6.56-6.61 (4H, m), 6.97-7.19 (12H, m).

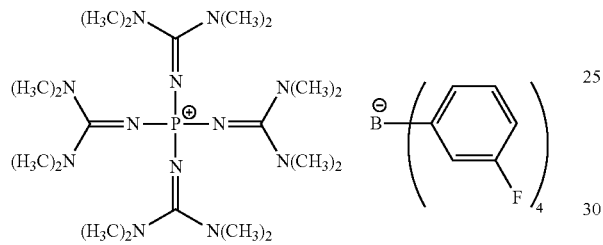

(114)

Comparative Example 15: Synthesis of 1,3-dimethyl-2-(N',N',N'',N''-tetramethylguanidino)-4,5-dihydro-3H-imidazolium tetrakis(3-fluorophenyl)borate (Compound Represented by the Formula (115))

Operations were performed in the same manner as in Example 1 except that 1,3-dimethyl-2-(N',N',N'',N''-tetramethylguanidino)-4,5-dihydro-3H-imidazolium chloride obtained in Synthetic Example 5 was used in place of 1,2-dicyclohexyl-4,4,5,5-tetramethylbiguanide carbonate and 3.5% hydrochloric acid, and 0.04 g of 1,3-dimethyl-2-(N',N',N'',N''-tetramethylguanidino)-4,5-dihydro-3H-imidazolium tetrakis(3-fluorophenyl)borate (white powder, yield: 31%) was obtained. The result of $^1$H-NMR measurement and the structure of 1,3-dimethyl-2-(N',N',N'',N''-tetramethylguanidino)-4,5-dihydro-3H-imidazolium tetrakis(3-fluorophenyl)borate are as follows.

$^1$H-NMR (400 MHz, (CD$_3$)$_2$CO) δ (ppm): 2.86 (12H, s), 2.98 (12H, s), 3.68-3.74 (4H, m), 6.48-6.62 (4H, m), 6.90-7.10 (12H, m).

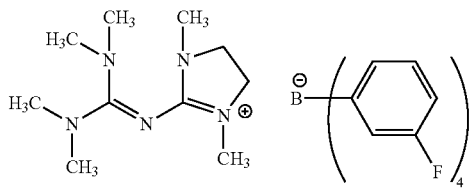

(115)

Comparative Example 16: Synthesis of 2,3,4,6,7,8,9,10-octahydro-1-(phenylmethyl)-pyrimido[1,2-a]azepinium tetrakis(3-fluorophenyl)borate (Compound Represented by the Formula (116))

Operations were performed in the same manner as in Example 1 except that 2,3,4,6,7,8,9,10-octahydro-1-(phenylmethyl)-pyrimido[1,2-a]azepinium bromide obtained in Synthetic Example 6 was used in place of 1,2-dicyclohexyl-4,4,5,5-tetramethylbiguanide carbonate and 3.5% hydrochloric acid, and 2.61 g of 2,3,4,6,7,8,9,10-octahydro-1-(phenylmethyl)-pyrimido[1,2-a]azepinium tetrakis(3-fluorophenyl)borate (white powder, yield: 58%) was obtained. The result of $^1$H-NMR measurement and the structure of 2,3,4,6,7,8,9,10-octahydro-1-(phenylmethyl)-pyrimido[1,2-a]azepinium tetrakis(3-fluorophenyl)borate are as follows.

$^1$H-NMR (400 MHz, CDCl$_3$) δ (ppm): 1.30-1.40 (2H, m), 1.45-1.50 (2H, m), 1.55-1.60 (2H, m), 1.65-1.73 (2H, m), 2.36-2.43 (2H, m), 2.95-3.10 (4H, m), 3.13-3.23 (2H, m), 4.26 (2H, s), 6.55-6.65 (4H, m), 6.88-7.07 (10H, m), 7.09-7.18 (4H, m), 7.30-7.40 (3H, m).

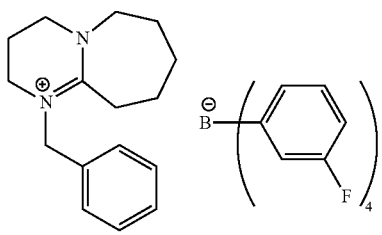

(116)

Comparative Example 17: Synthesis of 1,1-dimethylbiguanidium tetrakis(3-fluorophenyl)borate (Compound Represented by the Formula (117))

Operations were performed in the same manner as in Example 1 except that 1,1-dimethylbiguanidium hydrochloride was used in place of 1,2-dicyclohexyl-4,4,5,5-tetramethylbiguanide carbonate and 3.5% hydrochloric acid, and 1.77 g of 1,1-dimethylbiguanidium tetrakis(3-fluorophenyl)borate (yellow oil, yield: 48%) was obtained. The result of $^1$H-NMR measurement and the structure of 1,1-dimethylbiguanidium tetrakis(3-fluorophenyl)borate are as follows.

$^1$H-NMR (400 MHz, (CD$_3$)$_2$CO) δ (ppm): 3.10 (6H, s), 6.40-6.50 (4H, brs), 6.55-6.60 (4H, m), 6.92-7.10 (14H, m).

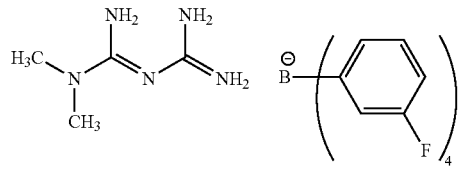

(117)

Comparative Example 18: Synthesis of 1,2-diisopropyl-1,4,4,5,5-pentamethylbiguanidium tetrakis(3-fluorophenyl)borate (Compound Represented by the Formula (118))

Operations were performed in the same manner as in Example 1 except that 1,2-diisopropyl-1,4,4,5,5-pentamethylbiguanide was used in place of 1,2-dicyclohexyl-4,4,5,5-tetramethylbiguanide carbonate, and 0.23 g of 1,2-diisopropyl-1,4,4,5,5-pentamethylbiguanidium tetrakis(3-fluorophenyl)borate (white powder, yield: 13%) was obtained. The result of $^1$H-NMR measurement and the structure of 1,2-diisopropyl-1,4,4,5,5-pentamethylbiguanidium tetrakis(3-fluorophenyl)borate are as follows.

$^1$H-NMR (400 MHz, CDCl$_3$) δ (ppm): 1.06 (6H, d, J=6.4 Hz), 1.09 (6H, d, J=6.4 Hz), 2.48 (3H, s), 2.67 (12H, s), 3.25-3.35 (1H, m), 3.90-4.00 (1H, m), 4.50-4.60 (1H, brs), 6.57-6.62 (4H, m), 6.95-7.06 (8H, m), 7.07-7.13 (4H, m).

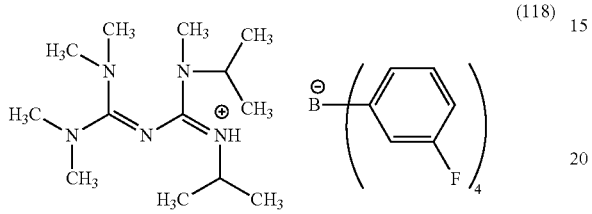

(118)

Experimental Example 1: Stability Test Against Acetic Acid (Acidic Compound)

Weighed was 10 mg of each of the compounds (the base-generating agents) obtained in Examples 1 to 5 and the compounds obtained in Comparative Examples 1 to 13, and 3 mL of acetic acid and 3 mL of 1,2-dichloroethane were added thereto, and the resultant was stirred at room temperature for 3 hours. Thereafter, the solvent was distilled off under reduced pressure, and the resulting residue was subjected to $^1$H-NMR measurement. The measurement results of the intrinsic $^1$H-NMR of each of the compounds in Examples 1 to 5 and Comparative Examples 1 to 13 and the $^1$H-NMR of it after the stability test were compared to determine the presence or absence of the decomposition of the boron unit. The stability was rated as "○" in a case where the decomposition rate of the boron unit after the stability test was less than 25%, as "x" in a case where the decomposition rate of the boron unit was 25% or more, and as "—" in a case where the stability test was not conducted. Table 1 shows the results of the stability test. It should be noted that "tetraphenylborate structure" according to the compound of the present invention refers to a structure in which a boron atom and four substituted phenyl groups are bonded together, and the bond between the boron atom and one phenyl group in the structure is referred to as "boron unit". In addition, since one tetraphenylborate structure has four boron units, the phrase "the decomposition rate of the boron unit is 25%" as the decomposition rate of one tetraphenylborate structure (all of the four boron units) is assumed as 100% means that one boron unit has completely decomposed.

TABLE 1

| Example | Compound | Stability against acetic acid |
|---|---|---|
| Example 1 | Compound represented by the formula (1) | ○ |
| Example 2 | Compound represented by the formula (2) | ○ |
| Example 3 | Compound represented by the formula (3) | ○ |

TABLE 1-continued

| Example | Compound | Stability against acetic acid |
|---|---|---|
| Example 4 | Compound represented by the formula (4) | ○ |
| Example 5 | Compound represented by the formula (5) | ○ |
| Comparative Example 1 | Compound represented by the formula (101) | X |
| Comparative Example 2 | Compound represented by the formula (102) | X |
| Comparative Example 3 | Compound represented by the formula (103) | ○ |
| Comparative Example 4 | Compound represented by the formula (104) | ○ |
| Comparative Example 5 | Compound represented by the formula (105) | ○ |
| Comparative Example 6 | Compound represented by the formula (106) | ○ |
| Comparative Example 7 | Compound represented by the formula (107) | — |
| Comparative Example 8 | Compound represented by the formula (108) | ○ |
| Comparative Example 9 | Compound represented by the formula (109) | ○ |
| Comparative Example 10 | Compound represented by the formula (110) | — |
| Comparative Example 11 | Compound represented by the formula (111) | — |
| Comparative Example 12 | Compound represented by the formula (112) | — |
| Comparative Example 13 | Compound represented by the formula (113) | — |

Experimental Example 2: Radical-Curing Test with Acrylate

Weighed were 10 mg of each of the compounds (the base-generating agents) obtained in Examples 1 to 5 or the compounds obtained in Comparative Examples 1 to 13 and 2 mg of 9-anthrylmethyl N,N-diethylcarbamate (product name: WPBG-018; manufactured by Wako Pure Chemical Industries, Ltd.) as a sensitizer, and the compound and the sensitizer were added to 100 mg of dipentaerythritol hexaacrylate (product name: KAYARAD DPHA; manufactured by Nippon Kayaku Co., Ltd.), and the resultant was warmed to 100° C. to dissolve the compound and the sensitizer. In addition, as Evaluation Example 1, 2 mg of 9-anthrylmethyl N,N-diethylcarbamate (product name: WPBG-018; manufactured by Wako Pure Chemical Industries, Ltd.) as a sensitizer was weighed, and only the sensitizer was added to 100 mg of dipentaerythritol hexaacrylate (product name: KAYARAD DPHA; manufactured by Nippon Kayaku Co., Ltd.), and the resultant was warmed to 100° C. to dissolve the sensitizer. Each solution was applied onto a glass plate to form a film, and the resulting coating film was irradiated with an ultraviolet ray (an active energy ray) by using the ultraviolet light source apparatus REX-250 (manufactured by Asahi Spectra Co., Ltd.), being capable of irradiating with light (an active energy ray) at wavelengths of 240 nm to 440 nm, at room temperature for 10 seconds to cure the coating film. The hardness of the coating film was evaluated according to a pencil hardness test method, and the curing performance was rated as "○" in a case where the coating film was cured and the hardness reached 2H or higher, and as "x" in a case where the coating film was not cured and the hardness was lower than 2H. Table 2 shows the evaluation results.

TABLE 2

| Example | Compound | Curing performance for acrylate |
|---|---|---|
| Example 1 | Compound represented by the formula (1) | ○ |
| Example 2 | Compound represented by the formula (2) | ○ |
| Example 3 | Compound represented by the formula (3) | ○ |
| Example 4 | Compound represented by the formula (4) | ○ |
| Example 5 | Compound represented by the formula (5) | ○ |
| Comparative Example 1 | Compound represented by the formula (101) | ○ |
| Comparative Example 2 | Compound represented by the formula (102) | ○ |
| Comparative Example 3 | Compound represented by the formula (103) | ○ |
| Comparative Example 4 | Compound represented by the formula (104) | ○ |
| Comparative Example 5 | Compound represented by the formula (105) | ○ |
| Comparative Example 6 | Compound represented by the formula (106) | ○ |
| Comparative Example 7 | Compound represented by the formula (107) | X |
| Comparative Example 8 | Compound represented by the formula (108) | ○ |
| Comparative Example 9 | Compound represented by the formula (109) | ○ |
| Comparative Example 10 | Compound represented by the formula (110) | ○ |
| Comparative Example 11 | Compound represented by the formula (111) | ○ |
| Comparative Example 12 | Compound represented by the formula (112) | ○ |
| Comparative Example 13 | Compound represented by the formula (113) | ○ |
| Evaluation Example 1 | WPBG-018 only | X |

Experimental Example 3: Storage Stability Test with Bisphenol A-Type Diglycidyl Ether Oligomer and Multivalent Carboxylic Acids (Acidic Compound)

Weighed were 10 mg of each of the compounds (the base-generating agents) obtained in Examples 1 to 5 or the compounds obtained in Comparative Examples 1 to 13 and 1 mg of 2-isopropylthioxanthone as a sensitizer, and the compound and the sensitizer were added to 100 mg of bisphenol A-type diglycidyl ether oligomer (product name: jER® 828; manufactured by Mitsubishi Chemical Corporation), and the resultant was warmed to dissolve the compound and the sensitizer. Thereafter, 100 mg of multivalent carboxylic acid (product name: CF-1069; 32.4% PGMEA solution, weight-average molecular weight: 14800, degree of dispersion: 1.85, acid value: 115 mg KOH/g; manufactured by Wako Pure Chemical Industries, Ltd.) was mixed therein. Each solution was applied onto a glass plate to form a film, and the resulting coating film was heated to 150° C. to cure the coating film. The hardness of the coating film (the cured film) after a given period from the initiation of heating was measured for evaluation according to a pencil hardness test method. A state where the hardness of the coating film reached 2H or higher was defined as "the coating film was cured", and the time from the initiation of heating to the completion of curing of the coating film was evaluated. Irradiation with light (an active energy ray) was not performed in Experimental Example 3, and, in addition, the compounds (the base-generating agents) obtained in Examples 1 to 5 or the compounds obtained in Comparative Examples 1 to 13 do not generate a base therefrom at the baking temperature (150° C.) in curing the coating film. That is, an operation to allow the compounds (the base-generating agents) obtained in Examples 1 to 5 or the compounds obtained in Comparative Examples 1 to 13 to generate a base therefrom was not performed in Experimental Example 3. Accordingly, as the stability of any of the compounds (the base-generating agents) obtained in Examples 1 to 5 or the compounds obtained in Comparative Examples 1 to 13 against the coexisting multivalent carboxylic acids is higher, in other words, as the acid resistance of any of the compounds (the base-generating agents) obtained in Examples 1 to 5 or the compounds obtained in Comparative Examples 1 to 13 is higher, the compound has a lower tendency to undergo decomposition due to the multivalent carboxylic acids and is less likely to generate a base or activate the multivalent carboxylic acids in association with such decomposition. In addition, a coating film in Experimental Example 3 requires longer time for curing as the corresponding compound has a lower tendency to generate a base. Thus, a longer time from the initiation of heating to the completion of curing of a coating film required for any of the compounds (the base-generating agents) obtained in Examples 1 to 5 or the compounds obtained in Comparative Examples 1 to 13 indicates that the compound has a higher acid resistance to acidic compounds such as multivalent carboxylic acids and higher stability against resin compositions containing an acidic compound. The stability was rated as "x x" in a case where the coating film was cured within 15 minutes from the initiation of heating, as "x" in a case where the coating film was cured in 16 to 30 minutes from the initiation of heating, and as "○" in a case where the coating film was not cured even after a lapse of 31 minutes or longer from the initiation of heating. Table 3 shows the evaluation results.

TABLE 3

| Example | Compound | Stability in epoxy/multivalent carboxylic acids |
|---|---|---|
| Example 1 | Compound represented by the formula (1) | ○ |
| Example 2 | Compound represented by the formula (2) | ○ |
| Example 3 | Compound represented by the formula (3) | ○ |
| Example 4 | Compound represented by the formula (4) | ○ |
| Example 5 | Compound represented by the formula (5) | ○ |
| Comparative Example 1 | Compound represented by the formula (101) | X X |
| Comparative Example 2 | Compound represented by the formula (102) | X X |
| Comparative Example 3 | Compound represented by the formula (103) | X X |
| Comparative Example 4 | Compound represented by the formula (104) | X X |
| Comparative Example 5 | Compound represented by the formula (105) | X X |
| Comparative Example 6 | Compound represented by the formula (106) | ○ |
| Comparative Example 7 | Compound represented by the formula (107) | ○ |
| Comparative Example 8 | Compound represented by the formula (108) | X X |
| Comparative Example 9 | Compound represented by the formula (109) | X |
| Comparative Example 10 | Compound represented by the formula (110) | ○ |

TABLE 3-continued

| Example | Compound | Stability in epoxy/multivalent carboxylic acids |
|---|---|---|
| Comparative Example 11 | Compound represented by the formula (111) | X |
| Comparative Example 12 | Compound represented by the formula (112) | X |
| Comparative Example 13 | Compound represented by the formula (113) | X |

Experimental Example 4: Base-Curing Test with Bisphenol A-Type Diglycidyl Ether Oligomer and Multivalent Carboxylic Acids (Acidic Compound)

Weighed were 10 mg of each of the compounds (the base-generating agents) obtained in Examples 1 to 5 or the compounds obtained in Comparative Examples 1 to 13 and 2 mg of 2-isopropylthioxanthone as a sensitizer, and the compound and the sensitizer were added to 100 mg of bisphenol A-type diglycidyl ether oligomer (product name: jER (R) 828; manufactured by Mitsubishi Chemical Corporation), and the resultant was warmed to dissolve the compound and the sensitizer. Thereafter, 100 mg of multivalent carboxylic acid (product name: CF-1069; 32.4% PGMEA solution, weight-average molecular weight: 14800, degree of dispersion: 1.85, acid value: 115 mg KOH/g; manufactured by Wako Pure Chemical Industries, Ltd.) was mixed therein. Each solution was applied onto a glass plate to form a film, and the resulting coating film was irradiated with an ultraviolet ray (an active energy ray) of 1.0 $J/cm^2$ at a wavelength of 365 nm by using the ultraviolet light source apparatus REX-250 (manufactured by Asahi Spectra Co., Ltd.), being capable of irradiating with light (an active energy ray) at wavelengths of 240 nm to 440 nm, and the coating film was then heated to 150° C. to cure the coating film. The hardness of the coating film after a given period from the initiation of heating was measured for evaluation according to a pencil hardness test method. A state where the hardness of the coating film reached 2H or higher was defined as "the coating film was cured", and the time from the initiation of heating to the completion of curing of the coating film was evaluated. Irradiation with light (an active energy ray) was performed in Experimental Example 4, and the amount of irradiation with light (an active energy ray) was identical for all of the cases. Accordingly, as the sensitivity of any of the compounds (the base-generating agents) obtained in Examples 1 to 5 or the compounds obtained in Comparative Examples 1 to 13 to light (an active energy ray) is higher, the compound has a higher tendency to generate a base therefrom. In addition, as the basicity of the base is higher, the coating film cures more easily. Thus, a shorter time from the initiation of heating to the completion of curing of a coating film required for any of the compounds (the base-generating agents) obtained in Examples 1 to 5 or the compounds obtained in Comparative Examples 1 to 13 indicates that the compound has a higher tendency to generate a base under irradiation with light (an active energy ray) and has higher curing performance for a coating film. The curing performance was rated as "⊚" in a case where the coating film was cured within 5 minutes from the initiation of heating, as "○" in a case where the coating film was cured in 6 to 15 minutes from the initiation of heating, and as "x" in a case where the coating film was cured after a lapse of 40 minutes or longer from the initiation of heating. Table 4 shows the evaluation results.

TABLE 4

| Example | Compound | Curing performance for epoxy/multivalent carboxylic acids |
|---|---|---|
| Example 1 | Compound represented by the formula (1) | ⊚ |
| Example 2 | Compound represented by the formula (2) | ○ |
| Example 3 | Compound represented by the formula (3) | ⊚ |
| Example 4 | Compound represented by the formula (4) | ⊚ |
| Example 5 | Compound represented by the formula (5) | ○ |
| Comparative Example 1 | Compound represented by the formula (101) | ⊚ |
| Comparative Example 2 | Compound represented by the formula (102) | ⊚ |
| Comparative Example 3 | Compound represented by the formula (103) | ⊚ |
| Comparative Example 4 | Compound represented by the formula (104) | ⊚ |
| Comparative Example 5 | Compound represented by the formula (105) | ⊚ |
| Comparative Example 6 | Compound represented by the formula (106) | X |
| Comparative Example 7 | Compound represented by the formula (107) | X |
| Comparative Example 8 | Compound represented by the formula (108) | ⊚ |
| Comparative Example 9 | Compound represented by the formula (109) | ⊚ |
| Comparative Example 10 | Compound represented by the formula (110) | X |
| Comparative Example 11 | Compound represented by the formula (111) | ⊚ |
| Comparative Example 12 | Compound represented by the formula (112) | ○ |
| Comparative Example 13 | Compound represented by the formula (113) | ⊚ |

The results of Experimental Examples 1 to 4 are summarized in Table 5.

TABLE 5

| Example | Compound | Stability against acetic acid | Curing performance for acrylate | Stability in epoxy/multivalent carboxylic acids | Curing performance for epoxy/multivalent carboxylic acids |
|---|---|---|---|---|---|
| Example 1 | Compound represented by the formula (1) | ○ | ○ | ○ | ⊚ |
| Example 2 | Compound represented by the formula (2) | ○ | ○ | ○ | ○ |
| Example 3 | Compound represented by the formula (3) | ○ | ○ | ○ | ⊚ |
| Example 4 | Compound represented by the formula (4) | ○ | ○ | ○ | ⊚ |

TABLE 5-continued

| Example | Compound | Stability against acetic acid | Curing performance for acrylate | Stability in epoxy/multivalent carboxylic acids | Curing performance for epoxy/multivalent carboxylic acids |
|---|---|---|---|---|---|
| Example 5 | Compound represented by the formula (5) | ○ | ○ | ○ | ○ |
| Comparative Example 1 | Compound represented by the formula (101) | X | ○ | X X | ◎ |
| Comparative Example 2 | Compound represented by the formula (102) | X | ○ | X X | ◎ |
| Comparative Example 3 | Compound represented by the formula (103) | ○ | ○ | X X | ◎ |
| Comparative Example 4 | Compound represented by the formula (104) | ○ | ○ | X X | ◎ |
| Comparative Example 5 | Compound represented by the formula (105) | ○ | ○ | X X | ◎ |
| Comparative Example 6 | Compound represented by the formula (106) | ○ | ○ | ○ | X |
| Comparative Example 7 | Compound represented by the formula (107) | — | X | ○ | X |
| Comparative Example 8 | Compound represented by the formula (108) | ○ | ○ | X X | ◎ |
| Comparative Example 9 | Compound represented by the formula (109) | ○ | ○ | X | ◎ |
| Comparative Example 10 | Compound represented by the formula (110) | — | ○ | ○ | X |
| Comparative Example 11 | Compound represented by the formula (111) | — | ○ | X | ◎ |
| Comparative Example 12 | Compound represented by the formula (112) | — | ○ | X | ○ |
| Comparative Example 13 | Compound represented by the formula (113) | — | ○ | X | ◎ |

As is clear from the results shown in Table 5, each of the compounds obtained in Comparative Examples 1 and 2 had low stability in acetic acid (acidic compound), and, in addition, had low stability in the resin composition containing the epoxy compounds and multivalent carboxylic acids. Thus, each of the compounds obtained in Comparative Examples 1 and 2 is understood to be unsuitable for use as a base-generating agent for resin compositions containing an acidic compound, and hence poor in versatility as a base-generating agent. In addition, it is known that borate base-generating agents generate a radical to form an intermediate in association with the decomposition of the borate structure through irradiation with light (an active energy ray) in the presence of a suitable sensitizer, and that the cationic portion (base) of the intermediate is dissociated from the intermediate to generate a base. However, the compound obtained in Comparative Example 7 was incapable of curing the acrylate, and thus is understood to be a compound which does not generate a radical even through irradiation with light (an active energy ray), and in turn does not easily decompose even through irradiation with light (an active energy ray). Further, each of the compounds obtained in Comparative Examples 3 to 5, 8, 9, and 11 to 13 had low stability in the resin composition containing the epoxy compounds and multivalent carboxylic acids, and cured the resin composition regardless of the presence or absence of irradiation with light (an active energy ray). From this result, each of the compounds obtained in Comparative Examples 3 to 5, 8, 9, and 11 to 13 is understood to have difficulty in achieving contrast between an exposed portion (a portion irradiated with light) and an unexposed portion (a portion not irradiated with light) and be unsuitable for application as a photo-base-generating agent. In addition, each of the compounds obtained in Comparative Examples 6, 7, and 10 was incapable of curing the resin composition containing the epoxy compounds and multivalent carboxylic acids. From this result, each of the compounds obtained in Comparative Examples 6, 7, and 10 is understood to be a base-generating agent unsuitable for application to a curing system for an epoxy compounds and poor in versatility.

In contrast, each of the compounds (the base-generating agents) of the present invention obtained in Examples 1 to 5 was good in stability against acetic acid (acidic compound) and stability in the resin composition containing the epoxy compounds and multivalent carboxylic acids. From this result, each of the compounds (the base-generating agents) of the present invention obtained in Examples 1 to 5 is understood to be a base-generating agent which exhibits high stability even when being mixed with an acidic compound. In addition, each of the compounds (the base-generating agents) of the present invention obtained in Examples 1 to 5 was good in curing performance for the acrylate and curing performance for the resin composition containing the epoxy compounds and multivalent carboxylic acids. From this result, each of the compounds (the base-generating agents) of the present invention is understood to be applicable as a base-generating agent for resin compositions which quickly generates a base through irradiation with light (an active energy ray) and provides a high contrast ratio between an exposed portion (a portion irradiated with light) and an unexposed portion (a portion not irradiated with light).

Experimental Example 5: Storage Stability Test with Bisphenol A-Type Diglycidyl Ether Oligomer and Polythiol (Acidic Compound)

Weighed were 10 mg of each of the compound (the base-generating agent) obtained in Example 1 or the compounds obtained in Comparative Examples 8, 9, and 12 to 18 and 2 mg of 2-isopropylthioxanthone as a sensitizer, and the compound and the sensitizer were added to 100 mg of bisphenol A-type diglycidyl ether oligomer (product name: jER® 828; manufactured by Mitsubishi Chemical Corporation), and the resultant was warmed to dissolve the compound and the sensitizer. Thereafter, 70 mg of polythiol (product name: KarenzMT® PE1; manufactured by Showa Denko K.K.) was mixed therein. Each solution was applied onto a glass plate to form a film, and the resulting coating film was heated to 120° C. to cure the coating film. The hardness of the coating film (the cured film) after a given period from the initiation of heating was measured for evaluation according to a pencil hardness test method. A state where the hardness of the coating film reached 2H or higher was defined as "the coating film was cured", and the time from the initiation of heating to the completion of curing of the coating film was evaluated. Irradiation with light (an active energy ray) was not performed in Experimental Example 5, and, in addition, the compound (the base-generating agent) obtained in Example 1 or the compounds obtained in Comparative Examples 8, 9, and 12 to 18 do not generate a base therefrom at the baking temperature (120° C.) in curing the coating film. That is, an operation to allow the compound (the base-generating agent) obtained in Example 1 or the compounds obtained in Comparative Examples 8, 9, and 12 to 18 to generate a base therefrom was not performed in Experimental Example 5. Accordingly, as the stability of any of the compound (the base-generating agent) obtained in Example 1 or the compounds obtained in Comparative Examples 8, 9, and 12 to 18 against the coexisting polythiol is higher, in other words, as the acid resistance of any of the compound (the base-generating agent) obtained in Example 1 or the compounds obtained in Comparative Examples 8, 9, and 12 to 18 is higher, the compound is less likely to generate a base or activate the polythiol in association with decomposition. In addition, a coating film in Experimental Example 5 requires longer time for curing as the corresponding compound has a lower tendency to generate a base. Thus, a longer time from the initiation of heating to the completion of curing of a coating film required for any of the compound (the base-generating agent) obtained in Example 1 or the compounds obtained in Comparative Examples 8, 9, and 12 to 18 indicates that the compound has higher stability against resin compositions containing polythiol. The stability was rated as "x" in a case where the coating film was cured in shorter than 120 minutes from the initiation of heating, and as "○" in a case where the coating film was not cured even after a lapse of 120 minutes or longer from the initiation of heating. Table 6 shows the evaluation results.

TABLE 6

| Example | Compound | Stability in epoxy/polythiol |
| --- | --- | --- |
| Example 1 | Compound represented by the formula (1) | ○ |
| Comparative Example 8 | Compound represented by the formula (108) | X |
| Comparative Example 9 | Compound represented by the formula (109) | X |
| Comparative Example 12 | Compound represented by the formula (112) | X |
| Comparative Example 13 | Compound represented by the formula (113) | ○ |
| Comparative Example 14 | Compound represented by the formula (114) | ○ |
| Comparative Example 15 | Compound represented by the formula (115) | ○ |
| Comparative Example 16 | Compound represented by the formula (116) | ○ |
| Comparative Example 17 | Compound represented by the formula (117) | ○ |

TABLE 6-continued

| Example | Compound | Stability in epoxy/polythiol |
| --- | --- | --- |
| Comparative Example 18 | Compound represented by the formula (118) | X |

Experimental Example 6: Base-Curing Test with Bisphenol A-Type Diglycidyl Ether Oligomer and Polythiol (Acidic Compound)

Weighed were 10 mg of each of the compound (the base-generating agent) obtained in Example 1 or the compounds obtained in Comparative Examples 8, 9, and 12 to 18 and 2 mg of 2-isopropylthioxanthone as a sensitizer, and the compound and the sensitizer were added to 100 mg of bisphenol A-type diglycidyl ether oligomer (product name: jER® 828; manufactured by Mitsubishi Chemical Corporation), and the resultant was warmed to dissolve the compound and the sensitizer. Thereafter, 70 mg of polythiol (product name: KarenzMT® PE1; manufactured by Showa Denko K.K.) was mixed therein. Each solution was applied onto a glass plate to form a film, and the resulting coating film was irradiated with an ultraviolet ray (an active energy ray) of 1.0 J/cm$^2$ at a wavelength of 365 nm by using the ultraviolet light source apparatus REX-250 (manufactured by Asahi Spectra Co., Ltd.), being capable of irradiating with light (an active energy ray) at wavelengths of 240 nm to 440 nm, and the coating film was then heated to 120° C. to cure the coating film. The hardness of the coating film after a given period from the initiation of heating was measured for evaluation according to a pencil hardness test method. A state where the hardness of the coating film reached 2H or higher was defined as "the coating film was cured", and the time from the initiation of heating to the completion of curing of the coating film was evaluated. Irradiation with light (an active energy ray) was performed in Experimental Example 6, and the amount of irradiation with light (an active energy ray) was identical for all of the cases. Accordingly, as the sensitivity of any of the compound (the base-generating agent) obtained in Example 1 or the compounds obtained in Comparative Examples 8, 9, and 12 to 18 to light (an active energy ray) is higher, the compound has a higher tendency to generate a base therefrom. In addition, as the basicity of the base is higher, the coating film cures more easily. Thus, a shorter time from the initiation of heating to the completion of curing of a coating film required for any of the compound (the base-generating agent) obtained in Example 1 or the compounds obtained in Comparative Examples 8, 9, and 12 to 18 indicates that the compound has a higher tendency to generate a base under irradiation with light (an active energy ray) and has higher curing performance for a coating film. The curing performance was rated as "○" in a case where the coating film was cured within 30 minutes from the initiation of heating, and as "x" in a case where the coating film was not cured even after a lapse of 30 minutes or longer from the initiation of heating. Table 7 shows the evaluation results.

TABLE 7

| Example | Compound | Curing performance for epoxy/polythiol |
| --- | --- | --- |
| Example 1 | Compound represented by the formula (1) | ○ |

TABLE 7-continued

| Example | Compound | Curing performance for epoxy/polythiol |
|---|---|---|
| Comparative Example 8 | Compound represented by the formula (108) | ○ |
| Comparative Example 9 | Compound represented by the formula (109) | ○ |
| Comparative Example 12 | Compound represented by the formula (112) | ○ |
| Comparative Example 13 | Compound represented by the formula (113) | X |
| Comparative Example 14 | Compound represented by the formula (114) | X |
| Comparative Example 15 | Compound represented by the formula (115) | X |
| Comparative Example 16 | Compound represented by the formula (116) | X |
| Comparative Example 17 | Compound represented by the formula (117) | X |
| Comparative Example 18 | Compound represented by the formula (118) | ○ |

The results of Experimental Examples 5 and 6 are summarized in Table 8.

TABLE 8

| Example | Compound | Stability in epoxy/polythiol | Curing performance for epoxy/polythiol |
|---|---|---|---|
| Example 1 | Compound represented by the formula (1) | ○ | ○ |
| Comparative Example 8 | Compound represented by the formula (108) | X | ○ |
| Comparative Example 9 | Compound represented by the formula (109) | X | ○ |
| Comparative Example 12 | Compound represented by the formula (112) | X | ○ |
| Comparative Example 13 | Compound represented by the formula (113) | ○ | X |
| Comparative Example 14 | Compound represented by the formula (114) | ○ | X |
| Comparative Example 15 | Compound represented by the formula (115) | ○ | X |
| Comparative Example 16 | Compound represented by the formula (116) | ○ | X |
| Comparative Example 17 | Compound represented by the formula (117) | ○ | X |
| Comparative Example 18 | Compound represented by the formula (118) | X | ○ |

As is clear from the results shown in Table 8, each of the compounds obtained in Comparative Examples 8, 9, 12, and 18 had low stability in the resin composition containing the epoxy compounds and polythiol, and cured the resin composition regardless of the presence or absence of irradiation with light (an active energy ray). From this result, each of the compounds obtained in Comparative Examples 8, 9, 12, and 18 is understood to have difficulty in achieving contrast between an exposed portion (a portion irradiated with light) and an unexposed portion (a portion not irradiated with light) and be unsuitable for application as a photo-base-generating agent. In addition, each of the compounds obtained in Comparative Examples 13 to 17 was incapable of curing the resin composition containing the epoxy compound and polythiol. From this result, each of the compounds obtained in Comparative Examples 13 to 17 is understood to be a base-generating agent unsuitable for application to a curing system for an epoxy compounds and poor in versatility.

In contrast, the compound (the base-generating agent) of the present invention obtained in Example 1 was good in stability in the resin composition containing the epoxy compounds and polythiol. From this result, the compound (the base-generating agent) of the present invention obtained in Example 1 is understood to be a base-generating agent which exhibits high stability even when being mixed with an acidic compound. In addition, the compound (the base-generating agent) of the present invention obtained in Example 1 was good in curing performance for the resin composition containing the epoxy compounds and polythiol. From this result, the compound (the base-generating agent) of the present invention is understood to be applicable as a base-generating agent for resin compositions which quickly generates a base through irradiation with light (an active energy ray) and provides a high contrast ratio between an exposed portion (a portion irradiated with light) and an unexposed portion (a portion not irradiated with light).

Experimental Example 7: Patterning with Bisphenol A-Type Diglycidyl Ether Oligomer and Multivalent Carboxylic Acids (Acidic Compound)

Weighed were 10 mg of each of the compound (the base-generating agent) obtained in Example 1 and 2 mg of 2-isopropylthioxanthone as a sensitizer, and the compound and the sensitizer, 100 mg of bisphenol A-type diglycidyl ether oligomer (product name: jER® 828; manufactured by Mitsubishi Chemical Corporation), and 100 mg of multivalent carboxylic acids (product name: Joncryl® 682; OH equivalent: 138; manufactured by BASF Japan Ltd.) were dissolved in 300 mg of γ-butyrolactone (manufactured by Wako Pure Chemical Industries, Ltd.). This solution was applied onto a polycarbonate sheet to form a film, and a part of the resulting coating film was irradiated with an ultraviolet ray (an active energy ray) of 1.0 J/cm$^2$ at a wavelength of 365 nm by using the ultraviolet light source apparatus REX-250 (manufactured by Asahi Spectra Co., Ltd.), being capable of irradiating with light (an active energy ray) at wavelengths of 240 nm to 440 nm, and the coating film was then heated at 1500° C. for 10 minutes to cure the coating film. The resulting cured film was soaked in an aqueous solution of sodium carbonate having a concentration of 1% by weight for 1 minute, and successful development was visually confirmed.

As is clear from the result of Experimental Example 7, the compound (the base-generating agent) obtained in Example 1 is understood to be applicable to patterning with a resin composition containing an epoxy compounds and a multivalent carboxylic acids.

INDUSTRIAL APPLICABILITY

The compound of the present invention represented by the general formula (A) and the base-generating agent and/or the radical-generating agent of the present invention each generate a strong base (biguanide) and/or a radical through irradiation with light (an active energy ray) or heating, and are each characterized by a low tendency to undergo decomposition by the action of an acid derived from an acidic compound such as a monomer raw material having an acidic proton and a crosslinking agent having an acidic proton, and, in addition, a low tendency to activate acidic compounds (having acid resistance). Accordingly, the compound of the present invention and the base-generating agent and/or the radical-generating agent of the present invention are each useful as a base-generating agent and/or the radical-generating agent for resin compositions containing an acidic compounds.

The base-curable resin composition and/or the radical-curable resin composition of the present invention each comprise or comprises the compound of the present invention. Since the compound of the present invention has acid resistance even when the resin composition contains an acidic compound (e.g., a monomer raw material having an acidic proton, a crosslinking agent having an acidic proton), the base-curable resin composition and/or the radical-curable resin composition of the present invention are/is applicable as a curing system for a resin composition containing an acidic compound. In particular, an acidic compound (a crosslinking agent) such as multivalent carboxylic acid and polythiol can accelerate curing of an epoxy compounds, and hence the base-curable resin composition and/or the radical-curable resin composition of the present invention are each or is a composition particularly effective for a curing system for an epoxy compounds, and thus the base-curable resin composition and/or the radical-curable resin composition of the present invention are each or is useful for curable materials, resist materials (patterning materials), and so on.

The invention claimed is:

1. A compound represented by the general formula (A):

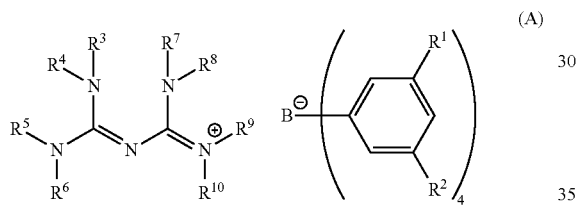

wherein four pieces of $R^1$ each independently represent a hydrogen atom or a fluorine atom; four pieces of $R^2$ each independently represent a fluorine atom or a trifluoromethyl group; $R^3$, $R^6$, $R^7$ and $R^{10}$ each independently represent a hydrogen atom or an alkyl group having 1 to 12 carbon atoms; $R^4$ and $R^5$ each independently represent a hydrogen atom or an alkyl group having 1 to 12 carbon atoms, or $R^4$ and $R^5$ are bonded to each other to represent an alkylene group having 2 to 4 carbon atoms; and $R^8$ and $R^9$ each independently represent a hydrogen atom, an alkyl group having 1 to 12 carbon atoms, or an aryl group having 6 to 14 carbon atoms and optionally having a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group, or $R^8$ and $R^9$ are bonded to each other to represent an alkylene group having 2 to 4 carbon atoms; provided that two or three of the eight groups $R^3$ to $R^{10}$ are each a hydrogen atom, and, in a case where two of the eight groups are each a hydrogen atom, then three to six of the remaining groups are each an alkyl group having 1 to 12 carbon atoms, and, in a case where three of the eight groups are each a hydrogen atom, then four or five of the remaining groups are each an alkyl group having 1 to 12 carbon atoms.

2. The compound according to claim 1, wherein, in the general formula (A), two of the eight groups $R^3$ to $R^{10}$ are each a hydrogen atom, and four to six of the remaining groups are each an alkyl group having 1 to 12 carbon atoms.

3. The compound according to claim 1, wherein, in the general formula (A), $R^3$ to $R^6$ are each an alkyl group having 1 to 6 carbon atoms.

4. The compound according to claim 1, wherein the compound represented by the general formula (A) is a compound represented by the general formula (C-A1), (C-A2) or (C-A3):

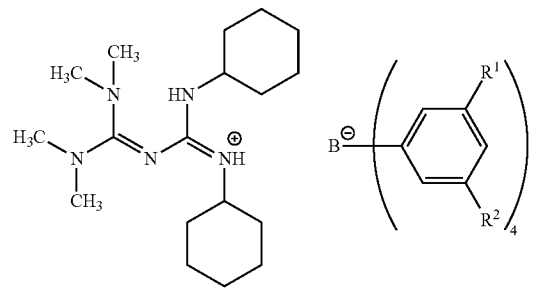

wherein four pieces of $R^1$ and four pieces of $R^2$ are as described above,

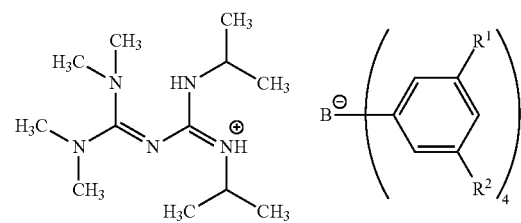

wherein four pieces of $R^1$ and four pieces of $R^2$ are as described above,

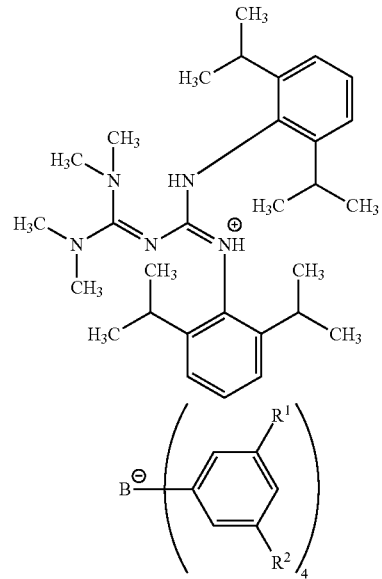

wherein four pieces of $R^1$ and four pieces of $R^2$ are as described above.

5. The compound according to claim 1, wherein, in the general formula (A), the four pieces of $R^1$ are each a hydrogen atom or each a fluorine atom, and the four pieces of $R^2$ are each a fluorine atom.

6. The compound according to claim 1, wherein, in the general formula (A), the four pieces of $R^1$ are each a hydrogen atom, and the four pieces of $R^2$ are each a trifluoromethyl group.

7. The compound according to claim 1, wherein the compound represented by the general formula (A) is a compound represented by the formula (1), (2), (3), (4) or (5):

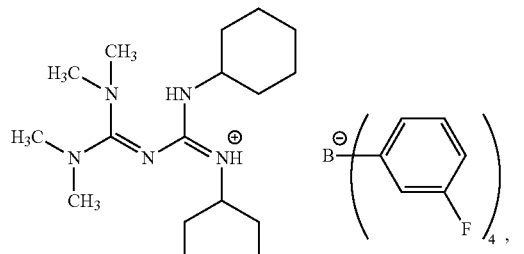
(1)

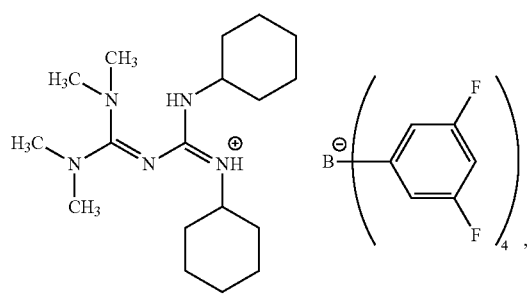
(2)

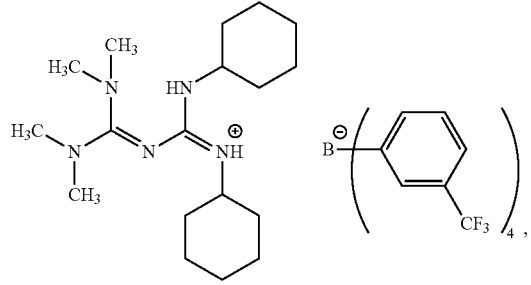
(3)

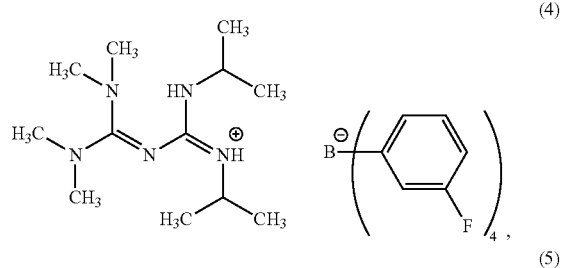
(4)

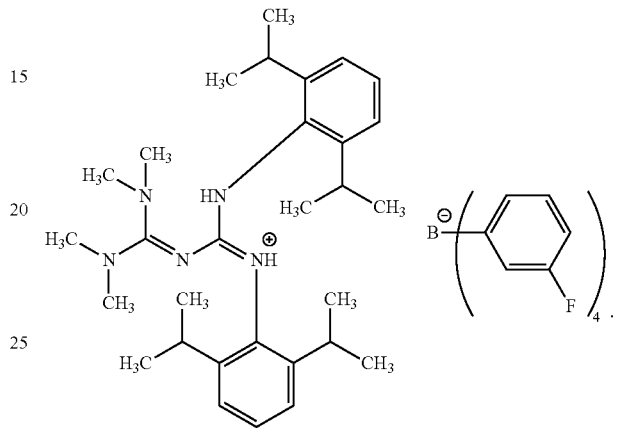
(5)

8. A base- and/or radical-generating agent comprising the compound according to claim 1.

9. The base- and/or radical-generating agent according to claim 8, wherein the base- and/or radical-generating agent generates a base and/or a radical through irradiation with an active energy ray.

10. A base-generating agent comprising the compound according to claim 1.

11. The base-generating agent according to claim 10, wherein the base-generating agent generates a base through irradiation with an active energy ray.

12. A base- and/or radical-curable resin composition comprising the compound according to claim 1, and a base-curable resin raw material and/or a radical-reactive compound.

13. The composition according to claim 12, wherein the base-curable resin raw material is a mixture of an epoxy compound and a multivalent carboxylic acid.

14. The composition according to claim 12, wherein the base-curable resin raw material is a mixture of an epoxy compound and a polythiol.

15. A base-curable resin composition comprising the compound according to claim 1, and a base-curable resin raw material.

\* \* \* \* \*